(12) United States Patent
Chou et al.

(10) Patent No.: US 11,098,329 B2
(45) Date of Patent: *Aug. 24, 2021

(54) EXPRESSION OF RECOMBINANT TETRACYCLINE EFFLUX PUMPS FOR THE PRODUCTION OF LYSINE OR LYSINE-DERIVED PRODUCTS, AND METHODS AND APPLICATIONS THEREOF

(71) Applicants: CATHAY BIOTECH INC., Shanghai (CN); CIBT AMERICA INC., Newark, DE (US)

(72) Inventors: Howard Chou, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,518

(22) Filed: Jul. 17, 2019

(65) Prior Publication Data

US 2019/0338323 A1 Nov. 7, 2019

Related U.S. Application Data

(62) Division of application No. 15/517,633, filed as application No. PCT/CN2014/088237 on Oct. 9, 2014, now Pat. No. 10,400,257.

(51) Int. Cl.
| | |
|---|---|
| *C12P 13/08* | (2006.01) |
| *C07K 14/35* | (2006.01) |
| *C07K 14/36* | (2006.01) |
| *C12N 9/88* | (2006.01) |
| *C07K 14/245* | (2006.01) |
| *C12N 15/70* | (2006.01) |
| *C12N 15/77* | (2006.01) |
| *C12P 13/00* | (2006.01) |

(52) U.S. Cl.
CPC ........... *C12P 13/08* (2013.01); *C07K 14/245* (2013.01); *C07K 14/35* (2013.01); *C07K 14/36* (2013.01); *C12N 9/88* (2013.01); *C12N 15/70* (2013.01); *C12N 15/77* (2013.01); *C12P 13/001* (2013.01)

(58) Field of Classification Search
CPC ...... C07K 14/36; C07K 14/35; C07K 14/245; C12N 15/70; C12N 9/88; C12N 15/77; C12P 13/001; C12P 13/08
See application file for complete search history.

(56) References Cited

U.S. PATENT DOCUMENTS

| | | | |
|---|---|---|---|
| 5,688,936 A | 11/1997 | Edwards | |
| 5,759,807 A * | 6/1998 | Breece | .................. C07K 14/64 435/69.1 |
| 6,670,156 B1 | 12/2003 | Mockel et al. | |
| 6,777,229 B1 | 8/2004 | Tauch et al. | |
| 7,026,152 B2 | 4/2006 | Ingram | |
| 7,189,543 B2 * | 3/2007 | Nishi | ..................... C08G 69/26 435/129 |

(Continued)

FOREIGN PATENT DOCUMENTS

| | | |
|---|---|---|
| CN | 1288055 A | 3/2001 |
| CN | 1295127 A | 5/2001 |
| EP | 1097998 A1 | 5/2001 |

OTHER PUBLICATIONS

Sutcliffe J.G., Complete nucleotide sequence of the *Escherichia coli* plasmid pBR322. Cold Spring Harb. Symp. Quant. Biol., 1979, vol. 43: 77-90 (Year: 1979).*

(Continued)

*Primary Examiner* — Ganapathirama Raghu
(74) *Attorney, Agent, or Firm* — Rothwell, Figg, Ernst & Manbeck, P.C.

(57) ABSTRACT

One aspect of the invention relates to a mutant polypeptide comprising the amino acid sequence of *Escherichia coli* tetracycline efflux pump A (TetA). Another aspect of the invention relates to a polynucleotide encoding a polypeptide of TetA, a fragment thereof, or a mutant thereof. Another aspect of the invention relates to a first expression plasmid vector comprising one or more first polynucleotides encoding a first polypeptide comprising a tetracycline efflux pump polypeptide, a fragment thereof or a mutant thereof, one or more second polynucleotides independently selected from the group consisting of a third polynucleotide encoding a third polypeptide comprising a lysine decarboxylase polypeptide, a fragment thereof or a mutant thereof, and a fourth polynucleotide encoding a fourth polypeptide comprising a lysine biosynthesis polypeptide, a fragment thereof or a mutant thereof. Another aspect of the invention relates to a transformant comprising one or more expression plasmid vectors as described herein in a host cell. Another aspect of the invention relates to a mutant host cell comprising one or more first, third or fourth polynucleotides as described herein integrated into a chromosome of a host cell. Another aspect of the invention relates to a method for producing a lysine comprising obtaining a transformant and/or mutant host cell as disclosed herein, culturing the transformant and/or mutant host cell under conditions effective for the expression of the lysine; and harvesting the lysine. Other aspects of the invention relate to methods for producing biobased cadaverine using the transformants disclosed herein, and biobased cadaverine prepared by the method disclosed herein, and polyamides formed using the biobased cadaverine as disclosed herein and compositions thereof.

11 Claims, 2 Drawing Sheets

Specification includes a Sequence Listing.

(56) References Cited

U.S. PATENT DOCUMENTS

| | | |
|---|---|---|
| 7,335,493 B2 | 2/2008 | Doucette-Stamm et al. |
| 8,017,363 B2 | 9/2011 | Gunji |
| 10,400,257 B2 * | 9/2019 | Chou .................. C07K 14/245 |
| 2011/0039313 A1 | 2/2011 | Verseck |
| 2013/0309733 A1 | 11/2013 | Pang et al. |

OTHER PUBLICATIONS

Chinese Office Action issued in corresponding Chinese Application No. 201480082442.3, dated Mar. 20, 2020, with an English translation, 9 pages.

International Search Report and Written Opinion dated Jul. 10, 2015 in PCT/CN2014/088237 (10 pages).

GenBank Accession No. KM17921.1 (4 pages), Aug. 12, 2014.

European Office Action issued in Application No. 14903578.4 dated Feb. 12, 2019, 6 pages.

The extended European Search Report issued in Application No. 14903578.4-1120 dated Feb. 7, 2018, 9 pages.

Database JPO Proteins [Online] Aug. 24, 2012, "JP 2007014342: Process for Producing Relaxin.", retrieved from EBE accession No. JPOP:BD948992, 1 page.

Database USPTO Proteins [Online] Apr. 3, 1998, "Sequence 7 from U.S. Pat. No. 5,688,936", retrieved from EBI accession No. USPOP:I75874, Database accession No. AAC11463, 1 page.

Broun et al., Catalytic plasticity of fatty acid modification enzymes underlying chemical diversity of plant lipids. Science, 1998, vol. 282: 1315-1317. (Year: 1998).

Devos et al., Practical limits of function prediction. Proteins: Structure, Function, and Genetics. 2000, vol. 41: 98-107. (Year: 2000).

Doyle et al., Characterization of an oxytetracycline-resistance gene, otrA, of Streptomyces rimosus. Mol. Microbial., 1991, vol. 5( 12) : 2923-2933. (Year: 1991).

Furushita et al., Similarity of tetracycline resistance genes isolated from fish farm bacteria to those from clinical isolates. Appl. Environ. Microbial., 2003, vol. 69(9): 5336-5342. (Year: 2003).

Kisselev L., Polypeptide release factors in prokaryotes and eukaryotes: same function, different structure. Structure, 2002, vol. 10: 8-9. (Year: 2002).

Liu et al., Preparation of D-lysine by chemical reaction and microbial asymmetric transformation. Front. Chem. Eng. China 2008, vol. 2(1): 40-43. (Year: 2008).

Seffernick et al., Melamine deaminase and Atrazine chlorohydrolase: 98 percent identical but functionally different. J. Bacterial., 2001, vol. 183 (8): 2405-2410. (Year: 2001).

Whisstock et al., Prediction of protein function from protein sequence. Q. Rev. Biophysics., 2003, vol. 36 (3): 307-340. (Year: 2003).

Witkowski et al., Conversion of b-ketoacyl synthase to a Malonyl Decarboxylase by replacement of the active cysteine with glutamine. Biochemistry, 1999, vol. 38: 11643-11650. (Year: 1999).

Communication pursuant to Article 94(3) EPC in application serial No. EP 14 903 578.4 dated Jul. 19, 2019, 4 pages.

* cited by examiner

FIG. 1

| Primer | Sequence |
|---|---|
| tetA-F | 5'- ggcgagctcacacaggaaacagaccatgaaatctaacaatgcgctcatc -3' (SEQ ID NO: 43) |
| tetA-R | 5'- ggctctagatcaacgacaggagcacgatc -3' (SEQ ID NO: 44) |
| tetA-F2 | 5'- ggctctagaacacaggaaacagaccatga -3' (SEQ ID NO: 45) |
| tetA-R2 | 5'- ggcaagctttcaacgacaggagcacgatc -3' (SEQ ID NO: 46) |
| tetA-F3 | 5' -ggcctcgagagtttattcttgacatgtagtgagg- 3' (SEQ ID NO: 47) |
| tetA-R3 | 5' -ggcgcatgctcaacgacaggagcacgatc- 3' (SEQ ID NO: 48) |
| tetAm1-F | 5' -gagtcgcattaagggagagc- 3' (SEQ ID NO: 49) |
| tetAm1-R | 5' -gctctcccttaatgcgactc- 3' (SEQ ID NO: 50) |
| tetAm2-F | 5' -cgtcctgtaaggatcctcta- 3' (SEQ ID NO: 51) |
| tetAm2-R | 5' -tagaggatccttacaggacg- 3' (SEQ ID NO: 52) |
| cadAm1-F | 5'- ggcctcgagctgtgcgaagaaattag -3' (SEQ ID NO: 53) |
| cadAm1-R | 5'- ggcgcatgctgttttcattcacgcaggttc -3' (SEQ ID NO: 54) |
| lysC-F | 5'- ggcgagctcacacaggaaacagaccatgtctgaaattgttgtctcc -3' (SEQ ID NO: 55) |
| lysC-R | 5'- ggcggatccttactcaaacaaattactatgcag -3' (SEQ ID NO: 56) |
| dapA-F | 5'- ggcggatccacacaggaaacagaccatgttcacgggaagtattgtc -3' (SEQ ID NO: 57) |
| dapA-R | 5'- ggctctagattacagcaaaccggcatgc -3' (SEQ ID NO: 58) |
| lysA-F | 5'- ggctctagaacacaggaaacagaccatgccacattcactgttcagc -3' (SEQ ID NO: 59) |
| lysA-R | 5'- ggcgtcgacttaaaagcaattccagcgccag -3' (SEQ ID NO: 60) |
| asd-F | 5' - ggcgagctcacacaggaaacagaccatgaaaaatgttggttttatcgg - 3' (SEQ ID NO: 61) |
| asd-R | 5' - ggcggatccttacgccagttgacgaagc- 3' (SEQ ID NO: 62) |
| dapB-F | 5' - ggcacacaggaaacagaccatgcatgatgcaaacatccg - 3' (SEQ ID NO: 63) |
| dapB-R | 5' - ggctctagattacaaattattgagatcaagtacatctc- 3' (SEQ ID NO: 64) |
| dapD-F | 5' - ggctctagaacacaggaaacagaccatgcagcagttacagaacat- 3' (SEQ ID NO: 65) |
| dapD-R | 5' - ggcgcatgcttagtcgatggtacgcagca- 3' (SEQ ID NO: 66) |
| aspC-F | 5' - ggctctagaacacaggaaacagaccatgtttgagaacattaccgcc- 3' (SEQ ID NO: 67) |
| aspC-R | 5' - ggcgcatgcgacctcgaggtagtcgacttacagcactgccacaatcg- 3' (SEQ ID NO: 68) |
| 318-F | 5' - cagcctgaatatactgcattctc- 3' (SEQ ID NO: 69) |
| 318-R | 5' - gagaatgcagtatattcaggctg- 3' (SEQ ID NO: 70) |
| 323-F | 5' - gcattctcgcgatttcctcg- 3' (SEQ ID NO: 71) |
| 323-R | 5' - cgaggaaatcgcgagaatgc- 3' (SEQ ID NO: 72) |
| 344-F | 5' - cttaatcaccatgtcagaagtg- 3' (SEQ ID NO: 73) |
| 344-R | 5' - cacttctgacatggtgattaag- 3' (SEQ ID NO: 74) |
| 352-F | 5' - cgtggcattaatccttgatac- 3' (SEQ ID NO: 75) |
| 352-R | 5' - gtatcaaggattaatgccacg- 3' (SEQ ID NO: 76) |
| SlysC-F | 5' - ggcgagctcacacaggaaacagaccatgggcttagttgtgcagaaa - 3' (SEQ ID NO: 77) |
| SlysC-R | 5' - ggcggatccttaacgacctgtgccgccata - 3' (SEQ ID NO: 78) |
| SAL-F | 5' - ggcggtaccagtttattcttgacatgtagtgagg - 3' (SEQ ID NO: 79) |
| SAL-R | 5' - ggcgggcccttaaaagcaattccagcgcca - 3' (SEQ ID NO: 80) |
| ABC-F | 5' - ggcgggccctgctggccttttgctcacat - 3' (SEQ ID NO: 81) |
| ABC-R | 5' - ggcggtaccttacagcactgccacaatcg - 3' (SEQ ID NO: 82) |
| ABCT-R | 5' - ggcggtacctcaacgacaggagcacgatc - 3' (SEQ ID NO: 83) |

FIG. 2

| Plasmid | Strain | Enzyme(s) | Gene(s) |
|---|---|---|---|
| | MG1655 K12 | none | none |
| pBR322 | | none | none |
| pUC18 | | none | none |
| pCIB7 | | LysC | lysC |
| pCIB8 | | LysC, DapA | lysC, dapA |
| pCIB9 | | LysC, DapA, LysA | lysC, dapA, lysA |
| pCIB10 | | none | none |
| pCIB12 | | Asd | asd |
| pCIB13 | | Asd, DapB | asd, dapB |
| pCIB14 | | Asd, DapB, DapD | asd, dapB, dapD |
| pCIB15 | | Asd, DapB, DapD, TetA | asd, dapB, dapD, tetA |
| pCIB17 | CIB17-EC; CIB17-HA | TetA | tetA |
| pCIB20 | CIB20 | TetA | tetA |
| pCIB31 | | Asd, DapB, AspC | asd, dapB, aspC |
| pCIB32 | CIB32 | LysC, DapA, LysA | lysC, dapA, lysA |
| pCIB43 | CIB43 | LysC-1(M318I, G323D), DapA, LysA | lysC-1, dapA, lysA |
| pCIB44 | CIB44 | LysC-2 (T344M, T352I), DapA, LysA | lysC-2, dapA, lysA |
| pCIB55 | CIB55 | S-LysC, DapA, LysA | S-lysC, dapA, lysA |
| pCIB59 | | Asd, DapB, AspC, TetA | asd, dapB, aspC, tetA |
| pCIB60 | CIB60 | CadA | cadA |
| pCIB63 | CIB63-EC; CIB63-HA | CadA (aa1-565) | mutant cadA |
| pCIB77 | CIB77 | TetA, CadA | tetA, cadA |
| pCIB92 | | S-LysC, DapA, LysA, Asd, DapB, AspC | S-lysC, dapA, lysA, asd, dapB, aspC, |
| pCIB97 | CIB97 | TetA (aa1-185), CadA | tetA (nt 1-558), cadA |
| pCIB98 | CIB98 | TetA (aa1-96), CadA | tetA (nt 1-291), cadA |
| pCIB103 | | S-LysC, DapA, LysA, Asd, DapB, AspC, TetA | S-lysC, dapA, lysA, asd, dapB, aspC, tetA |

"S"=*Streptomyces lividans*
"EC"= *E. coli*
"HA"= *Hafnia alvei*
"aa"= amino acids
"nt"= nucleotides

SEQUENCE LISTING

<160> NUMBER OF SEQ ID NOS: 83

<210> SEQ ID NO 1
<211> LENGTH: 1191
<212> TYPE: DNA
<213> ORGANISM: Escherichia coli

<400> SEQUENCE: 1

```
atgaaatcta acaatgcgct catcgtcatc ctcggcaccg tcaccctgga tgctgtaggc      60
ataggcttgg ttatgccggt actgccgggc ctcttgcggg atatcgtcca ttccgacagc     120
atcgccagtc actatggcgt gctgctagcg ctatatgcgt tgatgcaatt tctatgcgca     180
cccgttctcg gagcactgtc cgaccgcttt ggccgccgcc cagtcctgct cgcttcgcta     240
cttggagcca ctatcgacta cgcgatcatg gcgaccacac ccgtcctgtg gatcctctac     300
gccggacgca tcgtggccgg catcaccggc gccacaggtg cggttgctgg cgcctatatc     360
gccgacatca ccgatgggga agatcgggct cgccacttcg ggctcatgag cgcttgtttc     420
ggcgtgggta tggtggcagg ccccgtggcc ggggactgt tgggcgccat ctccttgcat     480
gcaccattcc ttgcggcggc ggtgctcaac ggcctcaacc tactactggg ctgcttccta     540
atgcaggagt cgcataaggg agagcgtcga ccgatgccct tgagagcctt caacccagtc     600
agctccttcc ggtgggcgcg gggcatgact atcgtcgccg cacttatgac tgtcttcttt     660
atcatgcaac tcgtaggaca ggtgccggca gcgctctggg tcattttcgg cgaggaccgc     720
tttcgctgga gcgcgacgat gatcggcctg tcgcttgcgg tattcggaat cttgcacgcc     780
ctcgctcaag ccttcgtcac tggtcccgcc accaaacgtt tcggcgagaa gcaggccatt     840
```

```
atcgccggca tggcggccga cgcgctgggc tacgtcttgc tggcgttcgc gacgcgaggc    900
tggatggcct tccccattat gattcttctc gcttccggcg gcatcgggat gcccgcgttg    960
caggccatgc tgtccaggca ggtagatgac gaccatcagg gacagcttca aggatcgctc   1020
gcggctctta ccagcctaac ttcgatcatt ggaccgctga tcgtcacggc gatttatgcc   1080
gcctcggcga gcacatggaa cgggttggca tggattgtag gcgccgccct ataccttgtc   1140
tgcctccccg cgttgcgtcg cggtgcatgg agccgggcca cctcgacctg a            1191
```

<210> SEQ ID NO 2
<211> LENGTH: 396
<212> TYPE: PRT
<213> ORGANISM: Escherichia coli

<400> SEQUENCE: 2

```
Met Lys Ser Asn Asn Ala Leu Ile Val Ile Leu Gly Thr Val Thr Leu
1               5                   10                  15

Asp Ala Val Gly Ile Gly Leu Val Met Pro Val Leu Pro Gly Leu Leu
            20                  25                  30

Arg Asp Ile Val His Ser Asp Ser Ile Ala Ser His Tyr Gly Val Leu
        35                  40                  45

Leu Ala Leu Tyr Ala Leu Met Gln Phe Leu Cys Ala Pro Val Leu Gly
    50                  55                  60

Ala Leu Ser Asp Arg Phe Gly Arg Arg Pro Val Leu Leu Ala Ser Leu
65                  70                  75                  80

Leu Gly Ala Thr Ile Asp Tyr Ala Ile Met Ala Thr Thr Pro Val Leu
                85                  90                  95

Trp Ile Leu Tyr Ala Gly Arg Ile Val Ala Gly Ile Thr Gly Ala Thr
            100                 105                 110

Gly Ala Val Ala Gly Ala Tyr Ile Ala Asp Ile Thr Asp Gly Glu Asp
        115                 120                 125

Arg Ala Arg His Phe Gly Leu Met Ser Ala Cys Phe Gly Val Gly Met
    130                 135                 140

Val Ala Gly Pro Val Ala Gly Gly Leu Leu Gly Ala Ile Ser Leu His
145                 150                 155                 160

Ala Pro Phe Leu Ala Ala Ala Val Leu Asn Gly Leu Asn Leu Leu Leu
                165                 170                 175

Gly Cys Phe Leu Met Gln Glu Ser His Lys Gly Glu Arg Arg Pro Met
            180                 185                 190

Pro Leu Arg Ala Phe Asn Pro Val Ser Ser Phe Arg Trp Ala Arg Gly
        195                 200                 205

Met Thr Ile Val Ala Ala Leu Met Thr Val Phe Phe Ile Met Gln Leu
    210                 215                 220

Val Gly Gln Val Pro Ala Ala Leu Trp Val Ile Phe Gly Glu Asp Arg
225                 230                 235                 240

Phe Arg Trp Ser Ala Thr Met Ile Gly Leu Ser Leu Ala Val Phe Gly
                245                 250                 255

Ile Leu His Ala Leu Ala Gln Ala Phe Val Thr Gly Pro Ala Thr Lys
            260                 265                 270

Arg Phe Gly Glu Lys Gln Ala Ile Ile Ala Gly Met Ala Ala Asp Ala
        275                 280                 285

Leu Gly Tyr Val Leu Leu Ala Phe Ala Thr Arg Gly Trp Met Ala Phe
    290                 295                 300

Pro Ile Met Ile Leu Leu Ala Ser Gly Gly Ile Gly Met Pro Ala Leu
```

```
                305                 310                 315                 320
Gln Ala Met Leu Ser Arg Gln Val Asp Asp His Gln Gly Gln Leu
                    325                 330                 335
Gln Gly Ser Leu Ala Ala Leu Thr Ser Leu Thr Ser Ile Ile Gly Pro
                340                 345                 350
Leu Ile Val Thr Ala Ile Tyr Ala Ser Ala Ser Thr Trp Asn Gly
                355                 360                 365
Leu Ala Trp Ile Val Gly Ala Ala Leu Tyr Leu Val Cys Leu Pro Ala
                370                 375                 380
Leu Arg Arg Gly Ala Trp Ser Arg Ala Thr Ser Thr
385                 390                 395

<210> SEQ ID NO 3
<211> LENGTH: 449
<212> TYPE: PRT
<213> ORGANISM: Escherichia coli

<400> SEQUENCE: 3

Met Ser Glu Ile Val Val Ser Lys Phe Gly Gly Thr Ser Val Ala Asp
1               5                   10                  15
Phe Asp Ala Met Asn Arg Ser Ala Asp Ile Val Leu Ser Asp Ala Asn
                20                  25                  30
Val Arg Leu Val Val Leu Ser Ala Ser Ala Gly Ile Thr Asn Leu Leu
            35                  40                  45
Val Ala Leu Ala Glu Gly Leu Glu Pro Gly Glu Arg Phe Glu Lys Leu
        50                  55                  60
Asp Ala Ile Arg Asn Ile Gln Phe Ala Ile Leu Glu Arg Leu Arg Tyr
65                  70                  75                  80
Pro Asn Val Ile Arg Glu Glu Ile Glu Arg Leu Leu Glu Asn Ile Thr
                85                  90                  95
Val Leu Ala Glu Ala Ala Ala Leu Ala Thr Ser Pro Ala Leu Thr Asp
                100                 105                 110
Glu Leu Val Ser His Gly Glu Leu Met Ser Thr Leu Leu Phe Val Glu
            115                 120                 125
Ile Leu Arg Glu Arg Asp Val Gln Ala Gln Trp Phe Asp Val Arg Lys
        130                 135                 140
Val Met Arg Thr Asn Asp Arg Phe Gly Arg Ala Glu Pro Asp Ile Ala
145                 150                 155                 160
Ala Leu Ala Glu Leu Ala Ala Leu Gln Leu Leu Pro Arg Leu Asn Glu
                165                 170                 175
Gly Leu Val Ile Thr Gln Gly Phe Ile Gly Ser Glu Asn Lys Gly Arg
                180                 185                 190
Thr Thr Thr Leu Gly Arg Gly Gly Ser Asp Tyr Thr Ala Ala Leu Leu
            195                 200                 205
Ala Glu Ala Leu His Ala Ser Arg Val Asp Ile Trp Thr Asp Val Pro
        210                 215                 220
Gly Ile Tyr Thr Thr Asp Pro Arg Val Val Ser Ala Ala Lys Arg Ile
225                 230                 235                 240
Asp Glu Ile Ala Phe Ala Glu Ala Ala Glu Met Ala Thr Phe Gly Ala
                245                 250                 255
Lys Val Leu His Pro Ala Thr Leu Leu Pro Ala Val Arg Ser Asp Ile
                260                 265                 270
Pro Val Phe Val Gly Ser Ser Lys Asp Pro Arg Ala Gly Gly Thr Leu
            275                 280                 285
```

```
Val Cys Asn Lys Thr Glu Asn Pro Pro Leu Phe Arg Ala Leu Ala Leu
290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu

<210> SEQ ID NO 4
<211> LENGTH: 292
<212> TYPE: PRT
<213> ORGANISM: Escherichia coli

<400> SEQUENCE: 4

Met Phe Thr Gly Ser Ile Val Ala Ile Val Thr Pro Met Asp Glu Lys
1               5                   10                  15

Gly Asn Val Cys Arg Ala Ser Leu Lys Lys Leu Ile Asp Tyr His Val
            20                  25                  30

Ala Ser Gly Thr Ser Ala Ile Val Ser Val Gly Thr Thr Gly Glu Ser
        35                  40                  45

Ala Thr Leu Asn His Asp Glu His Ala Asp Val Val Met Met Thr Leu
    50                  55                  60

Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Ala Asn
        195                 200                 205
```

```
Val Ala Ala Arg Asp Met Ala Gln Met Cys Lys Leu Ala Ala Glu Gly
            210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
            275                 280                 285

Ala Gly Leu Leu
    290

<210> SEQ ID NO 5
<211> LENGTH: 420
<212> TYPE: PRT
<213> ORGANISM: Escherichia coli

<400> SEQUENCE: 5

Met Pro His Ser Leu Phe Ser Thr Asp Thr Asp Leu Thr Ala Glu Asn
1               5                   10                  15

Leu Leu Arg Leu Pro Ala Glu Phe Gly Cys Pro Val Trp Val Tyr Asp
            20                  25                  30

Ala Gln Ile Ile Arg Arg Gln Ile Ala Ala Leu Lys Gln Phe Asp Val
        35                  40                  45

Val Arg Phe Ala Gln Lys Ala Cys Ser Asn Ile His Ile Leu Arg Leu
    50                  55                  60

Met Arg Glu Gln Gly Val Lys Val Asp Ser Val Ser Leu Gly Glu Ile
65                  70                  75                  80

Glu Arg Ala Leu Ala Ala Gly Tyr Asn Pro Gln Thr His Pro Asp Asp
                85                  90                  95

Ile Val Phe Thr Ala Asp Val Ile Asp Gln Ala Thr Leu Glu Arg Val
            100                 105                 110

Ser Glu Leu Gln Ile Pro Val Asn Ala Gly Ser Val Asp Met Leu Asp
        115                 120                 125

Gln Leu Gly Gln Val Ser Pro Gly His Arg Val Trp Leu Arg Val Asn
130                 135                 140

Pro Gly Phe Gly His Gly His Ser Gln Lys Thr Asn Thr Gly Gly Glu
145                 150                 155                 160

Asn Ser Lys His Gly Ile Trp Tyr Thr Asp Leu Pro Ala Ala Leu Asp
                165                 170                 175

Val Ile Gln Arg His His Leu Gln Leu Val Gly Ile His Met His Ile
            180                 185                 190

Gly Ser Gly Val Asp Tyr Ala His Leu Glu Gln Val Cys Gly Ala Met
        195                 200                 205

Val Arg Gln Val Ile Glu Phe Gly Gln Asp Leu Gln Ala Ile Ser Ala
    210                 215                 220

Gly Gly Gly Leu Ser Val Pro Tyr Gln Gln Gly Glu Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
            260                 265                 270

Leu Val Ala Gln Ser Gly Val Leu Ile Thr Gln Val Arg Ser Val Lys
        275                 280                 285
```

```
Gln Met Gly Ser Arg His Phe Val Leu Val Asp Ala Gly Phe Asn Asp
        290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335

Val Ala Gly Pro Leu Cys Glu Ser Gly Asp Val Phe Thr Gln Gln Glu
                340                 345                 350

Gly Gly Asn Val Glu Thr Arg Ala Leu Pro Glu Val Lys Ala Gly Asp
            355                 360                 365

Tyr Leu Val Leu His Asp Thr Gly Ala Tyr Gly Ala Ser Met Ser Ser
370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Gln Thr Ile Glu Glu Leu Leu Ala
                405                 410                 415

Leu Glu Leu Leu
            420

<210> SEQ ID NO 6
<211> LENGTH: 715
<212> TYPE: PRT
<213> ORGANISM: Escherichia coli

<400> SEQUENCE: 6

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
```

```
            225                 230                 235                 240
Asp Arg Asn Cys His Lys Ser Leu Thr His Leu Met Met Ser Asp
                245                 250                 255

Val Thr Pro Ile Tyr Phe Arg Pro Thr Arg Asn Ala Tyr Gly Ile Leu
                260                 265                 270

Gly Gly Ile Pro Gln Ser Glu Phe Gln His Ala Thr Ile Ala Lys Arg
                275                 280                 285

Val Lys Glu Thr Pro Asn Ala Thr Trp Pro Val His Ala Val Ile Thr
                290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
                355                 360                 365

Leu Ala Ala Phe Ser Gln Ala Ser Met Ile His Val Lys Gly Asp Val
                370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
                435                 440                 445

Trp Phe Phe Asp Val Trp Gln Pro Asp His Ile Asp Thr Thr Glu Cys
                450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
                515                 520                 525

Gly Pro Tyr Asn Leu Leu Phe Leu Phe Ser Ile Gly Ile Asp Lys Thr
                530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
                580                 585                 590

Ile His Lys Leu Ile Val His His Asn Leu Pro Asp Leu Met Tyr Arg
                595                 600                 605

Ala Phe Glu Val Leu Pro Thr Met Val Met Thr Pro Tyr Ala Ala Phe
                610                 615                 620

Gln Lys Glu Leu His Gly Met Thr Glu Val Tyr Leu Asp Glu Met
625                 630                 635                 640

Val Gly Arg Ile Asn Ala Asn Met Ile Leu Pro Tyr Pro Pro Gly Val
                645                 650                 655
```

```
Pro Leu Val Met Pro Gly Glu Met Ile Thr Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Ser Lys Lys
705                 710                 715

<210> SEQ ID NO 7
<211> LENGTH: 713
<212> TYPE: PRT
<213> ORGANISM: Escherichia coli

<400> SEQUENCE: 7

Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu
    50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
    130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
            180                 185                 190

His Thr Gly Pro His Leu Glu Ala Glu Glu Tyr Ile Ala Arg Thr Phe
        195                 200                 205

Gly Ala Glu Gln Ser Tyr Ile Val Thr Asn Gly Thr Ser Thr Ser Asn
    210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
            260                 265                 270

Gly Gly Ile Pro Arg Arg Glu Phe Thr Arg Asp Ser Ile Glu Glu Lys
        275                 280                 285

Val Ala Ala Thr Thr Gln Ala Gln Trp Pro Val His Ala Val Ile Thr
    290                 295                 300

Asn Ser Thr Tyr Asp Gly Leu Leu Tyr Asn Thr Asp Trp Ile Lys Gln
```

-continued

```
          305                 310                 315                 320
      Thr Leu Asp Val Pro Ser Ile His Phe Asp Ser Ala Trp Val Pro Tyr
                      325                 330                 335
      Thr His Phe His Pro Ile Tyr Gln Gly Lys Ser Gly Met Ser Gly Glu
                      340                 345                 350
      Arg Val Ala Gly Lys Val Ile Phe Glu Thr Gln Ser Thr His Lys Met
                      355                 360                 365
      Leu Ala Ala Leu Ser Gln Ala Ser Leu Ile His Ile Lys Gly Glu Tyr
                      370                 375                 380
      Asp Glu Glu Ala Phe Asn Glu Ala Phe Met Met His Thr Thr Thr Ser
      385                 390                 395                 400
      Pro Ser Tyr Pro Ile Val Ala Ser Val Glu Thr Ala Ala Ala Met Leu
                      405                 410                 415
      Arg Gly Asn Pro Gly Lys Arg Leu Ile Asn Arg Ser Val Glu Arg Ala
                      420                 425                 430
      Leu His Phe Arg Lys Glu Val Gln Arg Leu Arg Glu Glu Ser Asp Gly
                      435                 440                 445
      Trp Phe Phe Asp Ile Trp Gln Pro Pro Gln Val Asp Glu Ala Glu Cys
                      450                 455                 460
      Trp Pro Val Ala Pro Gly Glu Gln Trp His Gly Phe Asn Asp Ala Asp
      465                 470                 475                 480
      Ala Asp His Met Phe Leu Asp Pro Val Lys Val Thr Ile Leu Thr Pro
                      485                 490                 495
      Gly Met Asp Glu Gln Gly Asn Met Ser Glu Glu Gly Ile Pro Ala Ala
                      500                 505                 510
      Leu Val Ala Lys Phe Leu Asp Glu Arg Gly Ile Val Val Glu Lys Thr
                      515                 520                 525
      Gly Pro Tyr Asn Leu Leu Phe Leu Phe Ser Ile Gly Ile Asp Lys Thr
                      530                 535                 540
      Lys Ala Met Gly Leu Leu Arg Gly Leu Thr Glu Phe Lys Arg Ser Tyr
      545                 550                 555                 560
      Asp Leu Asn Leu Arg Ile Lys Asn Met Leu Pro Asp Leu Tyr Ala Glu
                      565                 570                 575
      Asp Pro Asp Phe Tyr Arg Asn Met Arg Ile Gln Asp Leu Ala Gln Gly
                      580                 585                 590
      Ile His Lys Leu Ile Arg Lys His Asp Leu Pro Gly Leu Met Leu Arg
                      595                 600                 605
      Ala Phe Asp Thr Leu Pro Glu Met Ile Met Thr Pro His Gln Ala Trp
                      610                 615                 620
      Gln Arg Gln Ile Lys Gly Glu Val Glu Thr Ile Ala Leu Glu Gln Leu
      625                 630                 635                 640
      Val Gly Arg Val Ser Ala Asn Met Ile Leu Pro Tyr Pro Pro Gly Val
                      645                 650                 655
      Pro Leu Leu Met Pro Gly Glu Met Leu Thr Lys Glu Ser Arg Thr Val
                      660                 665                 670
      Leu Asp Phe Leu Leu Met Leu Cys Ser Val Gly Gln His Tyr Pro Gly
                      675                 680                 685
      Phe Glu Thr Asp Ile His Gly Ala Lys Gln Asp Glu Asp Gly Val Tyr
                      690                 695                 700
      Arg Val Arg Val Leu Lys Met Ala Gly
      705                 710
```

<210> SEQ ID NO 8

<211> LENGTH: 2256
<212> TYPE: DNA
<213> ORGANISM: Pseudomonas aeruginosa

<400> SEQUENCE: 8

| | | | | | |
|---|---|---|---|---|---|
| atgtataaag | acctcaaatt | tcccgtcctc | atcgtccatc | gcgacatcaa | ggccgacacc | 60 |
| gttgccggcg | aacgcgtgcg | gggcatcgcc | cacgaactgg | agcaggacgg | cttcagcatt | 120 |
| ctctccaccg | ccagctccgc | cgaggggcgc | atcgtcgctt | ccacccacca | cggcctggcc | 180 |
| tgcattctgg | tcgccgccga | aggtgccggg | gaaaaccagc | gcctgctgca | ggatgtggtc | 240 |
| gaactgatcc | gcgtggcccg | cgtgcggcg | ccgcaattgc | cgatcttcgc | cctcggcgag | 300 |
| caggtgacca | tcgagaacgc | gccggccgag | tccatggccg | acctgcacca | gttgcgcggc | 360 |
| atcctctacc | tgttcgaaga | caccgtgccg | ttcctcgccc | gccaggtcgc | ccgggcggcg | 420 |
| cgcaactacc | tggccgggct | gctgccgcca | ttcttccgtg | cgctggtcga | gcacaccgcg | 480 |
| cagtccaact | attcctggca | tacgccgggc | acggcggcg | gtgtcgccta | tcgcaagagt | 540 |
| ccggtgggac | aggcgttcca | ccagttcttc | ggggagaaca | cgctgcgttc | cgacctgtcg | 600 |
| gtctcggtcc | ccgagctggg | atcgctgctc | gaccataccg | gccccctggc | cgaggccgag | 660 |
| gaccgtgccg | cgcgcaattt | cggcgccgac | catacctctc | tcgtgatcaa | tggcacttcc | 720 |
| accgcgaaca | agatcgtctg | gcactccatg | gtcggtcgcg | aagacctggt | gctggtggac | 780 |
| cgcaactgcc | acaagtcgat | cctccactcg | atcatcatga | ccggggcgat | accgctctac | 840 |
| ctgactccgg | aacgcaacga | actggggatc | atcgggccga | tcccgctgag | cgaattcagc | 900 |
| aagcagtcga | tcgccgcgaa | gatcgccgcc | agcccgctgg | cgcgcggccg | cgagccgaag | 960 |
| gtgaagctgg | cggtggtgac | taactccacc | tacgacggcc | tgtgctacaa | cgccgagctg | 1020 |
| atcaagcaga | ccctcggcga | cagcgtcgag | gtgttgcact | cgacgaggc | ttggtacgcc | 1080 |
| tatgccgcgt | tccacgagtt | ctacgacgga | cgctatggca | tgggcacctc | gcgcagcgag | 1140 |
| gagggacccc | tggtgttcgc | cacccactcc | acgcacaaga | tgctcgccgc | cttcagccag | 1200 |
| gcctcgatga | tccacgtgca | ggatggcggg | accggaagc | tggacgtggc | gcgcttcaac | 1260 |
| gaagccttca | tgatgcacat | ctcgacctcg | ccgcagtacg | gcatcatcgc | ttcgctggac | 1320 |
| gtggcttcgg | cgatgatgga | agggcccgcc | gggcgttcgc | tgatccagga | gaccttcgac | 1380 |
| gaggccctca | gcttccgccg | ggccctggcc | aacgtacggc | agaacctgga | ccggaacgac | 1440 |
| tggtggttcg | gcgtctggca | gccggagcag | gtggagggca | ccgaccaggt | cggcacccat | 1500 |
| gactgggtgc | tggagccgag | cgccgactgg | cacggcttcg | gcgatatcgc | cgaagactac | 1560 |
| gtgctgctcg | acccgatcaa | ggtcacccctg | accaccccgg | gcctgagcgc | tggcggcaag | 1620 |
| ctcagcgagc | aggggattcc | ggccgccatc | gtcagccgct | tcctctggga | gcgcgggctg | 1680 |
| gtggtggaga | aaaccggtct | ctactccttc | ctggtgctgt | tctcgatggg | catcaccaag | 1740 |
| ggcaagtgga | gcaccctggt | caccgaactg | ctcgaattca | agcgctgtta | cgacgccaac | 1800 |
| ctgccgctgc | ttgacgtctt | gccctccgtg | gccaggccg | cggcaagcg | ctacaacgga | 1860 |
| gtgggcctgc | gcgacctcag | cgacgccatg | cacgccagct | accgcgacaa | cgccacggcg | 1920 |
| aaggccatga | gcgcgcatgta | cacggtgctg | ccggaggtcg | cgatgcggcc | gtccgaggcc | 1980 |
| tacgacaagc | tggtgcgcgg | cgaggtcgag | gcggtaccga | tcgctcggtt | ggaagggcgc | 2040 |
| atcgcggccg | tcatgctggt | accctatccg | ccgggtatcc | cgctgatcat | gccgggtgag | 2100 |
| cgcttcaccg | aggcgacccg | ctcgatcctc | gactatctcg | agttcgcgcg | gaccttcgag | 2160 |
| cgcgccttcc | ctggtttcga | ctccgatgtg | catggcctgc | agcatcagga | cggaccgtcc | 2220 | gggcgctgct ataccgttga atgcataaag gaatga                    2256

<210> SEQ ID NO 9
<211> LENGTH: 751
<212> TYPE: PRT
<213> ORGANISM: Pseudomonas aeruginosa

<400> SEQUENCE: 9

| | | | | | | | | | | | | | | |
|---|---|---|---|---|---|---|---|---|---|---|---|---|---|---|
| Met | Tyr | Lys | Asp | Leu | Lys | Phe | Pro | Val | Leu | Ile | Val | His | Arg | Asp | Ile |
| 1 | | | | 5 | | | | | 10 | | | | | 15 | |
| Lys | Ala | Asp | Thr | Val | Ala | Gly | Glu | Arg | Val | Arg | Gly | Ile | Ala | His | Glu |
| | | | 20 | | | | | 25 | | | | | 30 | | |
| Leu | Glu | Gln | Asp | Gly | Phe | Ser | Ile | Leu | Ser | Thr | Ala | Ser | Ser | Ala | Glu |
| | | | 35 | | | | 40 | | | | | 45 | | | |
| Gly | Arg | Ile | Val | Ala | Ser | Thr | His | His | Gly | Leu | Ala | Cys | Ile | Leu | Val |
| | 50 | | | | | 55 | | | | | 60 | | | | |
| Ala | Ala | Glu | Gly | Ala | Gly | Glu | Asn | Gln | Arg | Leu | Leu | Gln | Asp | Val | Val |
| 65 | | | | | 70 | | | | | 75 | | | | | 80 |
| Glu | Leu | Ile | Arg | Val | Ala | Arg | Val | Arg | Ala | Pro | Gln | Leu | Pro | Ile | Phe |
| | | | | 85 | | | | | 90 | | | | | 95 | |
| Ala | Leu | Gly | Glu | Gln | Val | Thr | Ile | Glu | Asn | Ala | Pro | Ala | Glu | Ser | Met |
| | | | 100 | | | | | 105 | | | | | 110 | | |
| Ala | Asp | Leu | His | Gln | Leu | Arg | Gly | Ile | Leu | Tyr | Leu | Phe | Glu | Asp | Thr |
| | | | 115 | | | | | 120 | | | | | 125 | | |
| Val | Pro | Phe | Leu | Ala | Arg | Gln | Val | Ala | Arg | Ala | Arg | Asn | Tyr | Leu |
| | 130 | | | | | 135 | | | | | 140 | | | | |
| Ala | Gly | Leu | Leu | Pro | Pro | Phe | Phe | Arg | Ala | Leu | Val | Glu | His | Thr | Ala |
| 145 | | | | | 150 | | | | | 155 | | | | | 160 |
| Gln | Ser | Asn | Tyr | Ser | Trp | His | Thr | Pro | Gly | His | Gly | Gly | Gly | Val | Ala |
| | | | | 165 | | | | | 170 | | | | | 175 | |
| Tyr | Arg | Lys | Ser | Pro | Val | Gly | Gln | Ala | Phe | His | Gln | Phe | Phe | Gly | Glu |
| | | | 180 | | | | | 185 | | | | | 190 | | |
| Asn | Thr | Leu | Arg | Ser | Asp | Leu | Ser | Val | Ser | Val | Pro | Glu | Leu | Gly | Ser |
| | | | 195 | | | | | 200 | | | | | 205 | | |
| Leu | Leu | Asp | His | Thr | Gly | Pro | Leu | Ala | Glu | Ala | Glu | Asp | Arg | Ala | Ala |
| | 210 | | | | | 215 | | | | | 220 | | | | |
| Arg | Asn | Phe | Gly | Ala | Asp | His | Thr | Phe | Phe | Val | Ile | Asn | Gly | Thr | Ser |
| 225 | | | | | 230 | | | | | 235 | | | | | 240 |
| Thr | Ala | Asn | Lys | Ile | Val | Trp | His | Ser | Met | Val | Gly | Arg | Glu | Asp | Leu |
| | | | | 245 | | | | | 250 | | | | | 255 | |
| Val | Leu | Val | Asp | Arg | Asn | Cys | His | Lys | Ser | Ile | Leu | His | Ser | Ile | Ile |
| | | | 260 | | | | | 265 | | | | | 270 | | |
| Met | Thr | Gly | Ala | Ile | Pro | Leu | Tyr | Leu | Thr | Pro | Glu | Arg | Asn | Glu | Leu |
| | | | 275 | | | | | 280 | | | | | 285 | | |
| Gly | Ile | Ile | Gly | Pro | Ile | Pro | Leu | Ser | Glu | Phe | Ser | Lys | Gln | Ser | Ile |
| | | | 290 | | | | | 295 | | | | | 300 | | |
| Ala | Ala | Lys | Ile | Ala | Ala | Ser | Pro | Leu | Ala | Arg | Gly | Arg | Glu | Pro | Lys |
| 305 | | | | | 310 | | | | | 315 | | | | | 320 |
| Val | Lys | Leu | Ala | Val | Val | Thr | Asn | Ser | Thr | Tyr | Asp | Gly | Leu | Cys | Tyr |
| | | | | 325 | | | | | 330 | | | | | 335 | |
| Asn | Ala | Glu | Leu | Ile | Lys | Gln | Thr | Leu | Gly | Asp | Ser | Val | Glu | Val | Leu |
| | | | 340 | | | | | 345 | | | | | 350 | | |
| His | Phe | Asp | Glu | Ala | Trp | Tyr | Ala | Tyr | Ala | Ala | Phe | His | Glu | Phe | Tyr |
| | | | 355 | | | | | 360 | | | | | 365 | | |

```
Asp Gly Arg Tyr Gly Met Gly Thr Ser Arg Ser Glu Glu Gly Pro Leu
    370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
                405                 410                 415

Ala Arg Phe Asn Glu Ala Phe Met Met His Ile Ser Thr Ser Pro Gln
                420                 425                 430

Tyr Gly Ile Ile Ala Ser Leu Asp Val Ala Ser Ala Met Met Glu Gly
            435                 440                 445

Pro Ala Gly Arg Ser Leu Ile Gln Glu Thr Phe Asp Glu Ala Leu Ser
    450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
                485                 490                 495

Val Gly Thr His Asp Trp Val Leu Glu Pro Ser Ala Asp Trp His Gly
                500                 505                 510

Phe Gly Asp Ile Ala Glu Asp Tyr Val Leu Leu Asp Pro Ile Lys Val
            515                 520                 525

Thr Leu Thr Thr Pro Gly Leu Ser Ala Gly Lys Leu Ser Glu Gln
    530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Val Thr Glu Leu Leu Glu
            580                 585                 590

Phe Lys Arg Cys Tyr Asp Ala Asn Leu Pro Leu Leu Asp Val Leu Pro
    595                 600                 605

Ser Val Ala Gln Ala Gly Gly Lys Arg Tyr Asn Gly Val Gly Leu Arg
    610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
                645                 650                 655

Pro Ser Glu Ala Tyr Asp Lys Leu Val Arg Gly Glu Val Glu Ala Val
            660                 665                 670

Pro Ile Ala Arg Leu Glu Gly Arg Ile Ala Ala Val Met Leu Val Pro
    675                 680                 685

Tyr Pro Pro Gly Ile Pro Leu Ile Met Pro Gly Glu Arg Phe Thr Glu
    690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
            740                 745                 750

<210> SEQ ID NO 10
<211> LENGTH: 2256
<212> TYPE: DNA
<213> ORGANISM: Artificial Sequence
<220> FEATURE:
```

<223> OTHER INFORMATION: synthetic

<400> SEQUENCE: 10

```
atgtacaaag atctgaaatt ccctgttctg attgtacacc gcgatatcaa ggcggacacg        60
gtagccggcg agcgtgttcg cggtattgcc cacgaactcg aacaagacgg ctttagcatt       120
ctctctacgg cgtcttctgc ggaaggccgc attgtggcta gcacgcacca cggtctcgcc       180
tgcatcctcg tggcagctga gggtgcgggt gagaatcagc gtctgctcca agacgtggtt       240
gagctgatcc gtgtagctcg cgtccgtgcg ccacagctcc cgatcttcgc gctgggcgaa       300
caggtgacta ttgaaaacgc gcctgccgaa tctatggccg acctgcacca gctccgcggc       360
attctgtatc tcttcgagga tactgtcccg ttcctggcac gtcaggttgc acgcgcagcg       420
cgtaactacc tcgctggcct cctcccgcca ttcttccgtg cactcgtgga gcacacggcc       480
caaagcaatt actcttggca caccccgggt cacggtggtg gtgtcgctta ccgtaaatct       540
ccggtaggtc aagctttcca ccagttcttt ggcgagaata ccctccgctc tgacctgtct       600
gttagcgttc cagagctggg cagcctgctg atcacactg gccctctcgc ggaagcagag       660
gatcgtgccg ctcgcaattt cggtgcggac cacaccttct ttgtcatcaa tggtacctct       720
actgcgaaca aaatcgtttg gcactctatg gttggtcgcg aggacctggt gctggtcgat       780
cgtaactgtc acaaatctat tctgcactcc attatcatga cgggtgctat cccactgtac       840
ctgactccgg aacgcaacga actgggtatt atcggcccta ttccactctc cgagttttct       900
aaacaatcta tcgcagcaaa aattgccgcc tccccactcg cgcgtggtcg tgaaccgaaa       960
gttaaactgg ctgtcgttac caactctacc tatgacggtc tgtgttacaa cgcggaactg      1020
atcaaacaaa ccctcggcga ctctgtcgag gtactgcatt cgacgaggc ttggtatgct      1080
tatgcggcgt tcacgagtt ctacgacggc cgctacggta tgggcacttc tcgttccgaa      1140
gagggtccgc tggtctttgc tacccattct acccacaaga tgctcgcggc ttttccccaa      1200
gctagcatga ttcacgttca ggatggtggt acgcgcaagc tggacgtcgc ccgctttaac      1260
gaagccttta tgatgcacat cagcacctct ccacagtacg gcatcattgc gtctctcgat      1320
gtcgcaagcg ctatgatgga aggtcctgcc ggtcgtagcc tgatccaaga gacgttcgat      1380
gaggcgctgt ccttccgtcg tgctctggcg aatgtccgtc agaacctgga ccgtaatgat      1440
tggtggttcg gtgtctggca accggagcag gttgagggca ccgaccaggt aggtactcac      1500
gactgggttc tcgagcctag cgcggactgg catggttttg gtgacattgc ggaggattac      1560
gttctcctcg atcctatcaa agttaccctg accaccccag gtctgagcgc tggcggtaaa      1620
ctctctgaac aaggcatccc ggcagctatc gttagccgtt cctgtgggga acgtggtctg      1680
gtggtcgaga aaacgggtct gtactctttc ctggttctgt tctccatggg tatcacgaaa      1740
ggcaaatggt ctactctggt taccgagctg ctcgaattca aacgctgtta cgacgcgaat      1800
ctgccactcc tggatgtgct gccttctgta gcgcaggcgg tggtaaacg ctataacggt      1860
gtaggtctgc gtgatctgtc cgatgccatg cacgcttctt atcgtgacaa tgccacggcg      1920
aaggccatga agcgtatgta tacggtgctc ccggaagtag ccatgcgccc gtccgaagct      1980
tatgataagc tcgtacgcgg tgaagtcgaa gctgttccta ttgcacgtct cgagggtcgt      2040
attgcggcgg ttatgctggt tccgtacccg ccaggtatcc cgctcattat gccgggtgaa      2100
cgtttttactg aagctacccg ctccattctg gactatctgg agtttgcccg taccttcgag      2160
cgcgcgttcc cggctttga ctctgatgtt cacggcctcc aacatcaaga tggcccgtct      2220
ggccgttgtt ataccgttga atgcatcaag gaataa                               2256
```

<210> SEQ ID NO 11
<211> LENGTH: 751
<212> TYPE: PRT
<213> ORGANISM: Artificial Sequence
<220> FEATURE:
<223> OTHER INFORMATION: synthetic

<400> SEQUENCE: 11

```
Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
            20                  25                  30

Leu Glu Gln Asp Gly Phe Ser Ile Leu Ser Thr Ala Ser Ser Ala Glu
        35                  40                  45

Gly Arg Ile Val Ala Ser Thr His His Gly Leu Ala Cys Ile Leu Val
    50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Cys Met
            100                 105                 110

Ala Asp Leu His Gln Leu Arg Gly Ile Leu Tyr Leu Phe Glu Asp Thr
        115                 120                 125

Val Pro Phe Leu Ala Arg Gln Val Ala Arg Ala Arg Asn Tyr Leu
    130                 135                 140

Ala Gly Leu Leu Pro Pro Phe Phe Arg Ala Leu Val Glu His Thr Ala
145                 150                 155                 160

Gln Ser Asn Tyr Ser Trp His Thr Pro Gly His Gly Gly Gly Val Ala
                165                 170                 175

Tyr Arg Lys Ser Pro Val Gly Gln Ala Phe His Gln Phe Phe Gly Glu
            180                 185                 190

Asn Thr Leu Arg Ser Asp Leu Ser Val Ser Val Pro Glu Leu Gly Ser
        195                 200                 205

Leu Leu Asp His Thr Gly Pro Leu Ala Glu Ala Glu Asp Arg Ala Ala
    210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
                245                 250                 255

Val Leu Val Asp Arg Asn Cys His Lys Ser Ile Leu His Ser Ile Ile
            260                 265                 270

Met Thr Gly Ala Ile Pro Leu Tyr Leu Thr Pro Glu Arg Asn Glu Leu
        275                 280                 285

Gly Ile Ile Gly Pro Ile Pro Leu Ser Glu Phe Ser Lys Gln Ser Ile
    290                 295                 300

Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Thr Leu Gly Asp Ser Val Glu Val Leu
            340                 345                 350

His Phe Asp Glu Ala Trp Tyr Ala Tyr Ala Ala Phe His Glu Phe Tyr
        355                 360                 365
```

Asp Gly Arg Tyr Gly Met Gly Thr Ser Arg Ser Glu Glu Gly Pro Leu
        370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
                405                 410                 415

Ala Arg Phe Asn Glu Ala Phe Met Met His Ile Ser Thr Ser Pro Gln
                420                 425                 430

Tyr Gly Ile Ile Ala Ser Leu Asp Val Ala Ser Ala Met Met Glu Gly
            435                 440                 445

Pro Ala Gly Arg Ser Leu Ile Gln Glu Thr Phe Asp Glu Ala Leu Ser
450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
                485                 490                 495

Val Gly Thr His Asp Trp Val Leu Glu Pro Ser Ala Asp Trp His Gly
                500                 505                 510

Phe Gly Asp Ile Ala Glu Asp Tyr Val Leu Leu Asp Pro Ile Lys Val
            515                 520                 525

Thr Leu Thr Thr Pro Gly Leu Ser Ala Gly Gly Lys Leu Ser Glu Gln
530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Val Thr Glu Leu Leu Glu
            580                 585                 590

Phe Lys Arg Cys Tyr Asp Ala Asn Leu Pro Leu Leu Asp Val Leu Pro
595                 600                 605

Ser Val Ala Gln Ala Gly Gly Lys Arg Tyr Asn Gly Val Gly Leu Arg
610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
                645                 650                 655

Pro Ser Glu Ala Tyr Asp Lys Leu Val Arg Gly Glu Val Glu Ala Val
                660                 665                 670

Pro Ile Ala Arg Leu Glu Gly Arg Ile Ala Ala Val Met Leu Val Pro
            675                 680                 685

Tyr Pro Pro Gly Ile Pro Leu Ile Met Pro Gly Glu Arg Phe Thr Glu
690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
            740                 745                 750

<210> SEQ ID NO 12
<211> LENGTH: 1333
<212> TYPE: DNA
<213> ORGANISM: Hafnia alvei

<400> SEQUENCE: 12

```
ttgactttgt taaaagtcag gcataagatc aaaatactgt atatataaca atgtatttat      60
atacagtatt ttatactttt tatctaacgt cagagagggc aatattatga gtggtggaga     120
tggcaagggt cacaatagtg gagcacatga ttccggtggc agcattaatg gaacttctgg     180
gaaaggtggg ccatcaagcg gaggagcatc agataattct gggtggagtt cggaaaataa     240
cccgtggggc ggtggtaact cgggaatgat tggtggcagt caaggaggta acggagctaa     300
tcatggtggc gaaaatacat cttctaacta tgggaaagat gtatcacgcc aaatcggtga     360
tgcgatagcc agaaaggaag gcatcaatcc gaaaatattc actgggtact ttatccgttc     420
agatggatat ttgatcggaa taacgccact tgtcagtggt gatgcctttg gcgttaatct     480
tggcctgttc aataacaatc aaaatagtag tagtgaaaat aagggatgga atggaaggaa     540
tggagatggc attaaaaata gtagccaagg tggatggaag attaaaacta atgaacttac     600
ttcaaaccaa gtagctgctg ctaaatccgt tccagaacct aaaaatagta atattataa      660
gtccatgaga gaagctagcg atgaggttat taattctaat ttaaaccaag gcatggagt      720
tggtgaggca gctagagctg aaagagatta cagagaaaaa gtaaagaacg caatcaatga     780
taatagtccc aatgtgctac aggatgctat taaatttaca gcagattttt ataaggaagt     840
tttttaacgct tacggagaaa aagccgaaaa actagccaag ttattagctg atcaagctaa     900
aggtaaaaag atccgcaatg tagaagatgc attgaaatct tatgaaaaac acaaggctaa     960
cattaacaaa aaaatcaatg cgaaagatcg cgaagctatc gccaaggctt tggagtctat    1020
ggatgtagaa aaagccgcaa aaatatatc caagttcagc aaaggactag gttgggttgg    1080
cccagctatc gatataactg attggtttac agaattatac aaagcagtga aaactgataa    1140
ttggagatct ctttatgtta aaactgaaac tattgcagta gggctagctg caacccatgt    1200
caccgcctta gcattcagtg ctgtcttggg tgggcctata ggtattttag gttatggttt    1260
gattatggct ggggttgggg cgttagttaa cgagacaata gttgacgagg caaataaggt    1320
cattgggatt taa                                                      1333
```

<210> SEQ ID NO 13
<211> LENGTH: 336
<212> TYPE: DNA
<213> ORGANISM: Hafnia alvei

<400> SEQUENCE: 13

```
ctatattttta gcggtcacat ttttatttc aaaacaaaca gaaagaacac caataggaat      60
tgatgtcata aaaataaaaa taaaatacaa agtcattaaa tatgttttg gcacaccatc     120
cttaaaaaaa cctgttttcc aaaattcttt tttcgtatat ctaagcgctg ctttctctat     180
tagaaaccga gagaaggaa atagaatagc gctagccaaa ccaaagattc tgagcgcaat     240
tatttttaggt tcgtcatcac cataactggc gtaaagaata caagcagcca taaagtatcc     300
ccaaaacata ttatgtatgt aatatttcct tgtcat                              336
```

<210> SEQ ID NO 14
<211> LENGTH: 1077
<212> TYPE: DNA
<213> ORGANISM: Hafnia alvei

<400> SEQUENCE: 14

```
atgagtggtg gagacggtaa aggtcacaat agtggagcac atgattccgg tgcagcatt       60
aatggaactt cggggaaagg tggacctgat tctggtggcg atattggga caaccatcca     120
```

```
catattacaa tcaccggtgg acgggaagta ggtcaagggg gagctggtat caactggggt      180
ggtggttctg gtcatggtaa cggcggggc tcagttgcca tccaagaata taacacgagt       240
aaatatccta acacgggagg atttcctcct cttggagacg ctagctggct gttaaatcct      300
ccaaaatggt cggttattga agtaaaatca gaaaactcag catggcgctc ttatattact      360
catgttcaag gtcatgttta caattgact tttgatggta cgggtaagct cattgatacc       420
gcgtatgtta attatgaacc cagtgatgat actcgttgga gcccgcttaa aagttttaaa      480
tataataaag gaaccgctga aaaacaggtt agggatgcca ttaacaatga aaagaagca      540 gttaaggacg ctgttaaatt tactgcagac ttctataaag aggttttaa ggtttacgga       600 gaaaaagccg agaagctcgc taagttatta gcagatcaag ctaaaggcaa aaggttcgc      660 aacgtagaag atgccttgaa atcttatgaa aaatataaga ctaacattaa caaaaaatc      720 aatgcgaaag atcgcgaagc tattgctaaa gccttggagt ctatggatgt aggaaagcc      780 gcaaaaata tagccaagtt cagtaaagga ctaggttggg ttggccctgc atcgatata       840 actgattggt ttacagaatt atacaaggca gtggaaactg ataattggag atctttttat      900
gttaaaactg aaactattgc agtagggcta gctgcaaccc atgttgccgc cttggcattc      960
agcgctgtct gggtgggcc tgtaggtatt ttgggttatg gtttgattat ggctggggtt     1020
ggggcgttag ttaatgagac aatagttgac gaggcaaata aggttattgg gctttaa       1077

<210> SEQ ID NO 15
<211> LENGTH: 336
<212> TYPE: DNA
<213> ORGANISM: Hafnia alvei

<400> SEQUENCE: 15
ctataattta gcggtcacat tttttatttc aaaaaaaaca gaaataacac ctataggaat       60
tgatgtcata aaaataaaaa ttaaatacaa agtcattaaa tatgtttttg gcacgccatc      120
cttaaaaaaa ccagtttccc aaaattcttt tttcgtatat ctaagcgcgg ttttctctat      180
taaaaaccga gagaagggga ataggatagc actagccaaa ccaaagattc tgagcgcaat      240
tattttaggt tcgttatccc cataactggc gtaaagaata caaacagcca taagtaccc      300 ccaaaacata ttatgtatat aatatttcct tgtcat                                 336

<210> SEQ ID NO 16
<211> LENGTH: 751
<212> TYPE: PRT
<213> ORGANISM: Artificial Sequence
<220> FEATURE:
<223> OTHER INFORMATION: synthetic

<400> SEQUENCE: 16
```

Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
            20                  25                  30

Leu Glu Gln Asp Gly Phe Ser Ile Leu Ser Thr Ala Ser Ser Ala Glu
        35                  40                  45

Gly Arg Ile Val Ala Ser Thr His His Gly Leu Ala Cys Ile Leu Val
    50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe

```
            85                    90                    95
Ala Leu Gly Glu Gln Val Thr Ile Glu Asn Ala Pro Ala Glu Ser Met
            100                   105                   110

Ala Asp Leu His Gln Leu Arg Gly Ile Leu Tyr Leu Phe Glu Asp Thr
            115                   120                   125

Val Pro Phe Leu Ala Arg Gln Val Ala Arg Ala Arg Asn Tyr Leu
            130                   135                   140

Ala Gly Leu Leu Pro Pro Phe Phe Arg Ala Leu Val Glu His Thr Ala
145                     150                   155                   160

Gln Ser Asn Tyr Ser Trp His Thr Pro Gly His Gly Gly Val Ala
                165                   170                   175

Tyr Arg Lys Ser Pro Val Gly Gln Ala Phe His Gln Phe Phe Gly Glu
                180                   185                   190

Asn Thr Leu Arg Ser Asp Leu Ser Val Ser Val Pro Glu Leu Gly Ser
                195                   200                   205

Leu Leu Asp His Thr Gly Pro Leu Ala Glu Ala Glu Asp Arg Ala Ala
                210                   215                   220

Arg Asn Phe Gly Ala Asp His Thr Phe Phe Val Ile Asn Gly Thr Ser
225                     230                   235                   240

Thr Ala Asn Lys Ile Val Trp His Ser Met Val Gly Arg Glu Asp Leu
                    245                   250                   255

Val Leu Val Asp Arg Thr Cys His Lys Ser Ile Leu His Ser Ile Ile
                260                   265                   270

Met Thr Gly Ala Ile Pro Leu Tyr Leu Thr Pro Glu Arg Asn Glu Leu
                275                   280                   285

Gly Ile Ile Gly Pro Ile Pro Leu Ser Glu Phe Ser Lys Gln Ser Ile
                290                   295                   300

Ala Ala Lys Ile Ala Ala Ser Pro Leu Ala Arg Gly Arg Glu Pro Lys
305                     310                   315                   320

Val Lys Leu Ala Val Val Thr Asn Ser Thr Tyr Asp Gly Leu Cys Tyr
                    325                   330                   335

Asn Ala Glu Leu Ile Lys Gln Thr Leu Gly Asp Ser Val Glu Val Leu
                340                   345                   350

His Phe Asp Glu Ala Trp Tyr Ala Tyr Ala Ala Phe His Glu Phe Tyr
                355                   360                   365

Asp Gly Arg Tyr Gly Met Gly Thr Ser Arg Ser Glu Glu Gly Pro Leu
                370                   375                   380

Val Phe Ala Thr His Ser Thr His Lys Met Leu Ala Ala Phe Ser Gln
385                     390                   395                   400

Ala Ser Met Ile His Val Gln Asp Gly Gly Thr Arg Lys Leu Asp Val
                    405                   410                   415

Ala Arg Phe Asn Glu Ala Phe Met Met His Ile Ser Thr Ser Pro Gln
                420                   425                   430

Tyr Gly Ile Ile Ala Ser Leu Asp Val Ala Ser Ala Met Met Glu Gly
                435                   440                   445

Pro Ala Gly Arg Ser Leu Ile Gln Glu Thr Phe Asp Glu Ala Leu Ser
                450                   455                   460

Phe Arg Arg Ala Leu Ala Asn Val Arg Gln Asn Leu Asp Arg Asn Asp
465                     470                   475                   480

Trp Trp Phe Gly Val Trp Gln Pro Glu Gln Val Glu Gly Thr Asp Gln
                    485                   490                   495

Val Gly Thr His Asp Trp Val Leu Glu Pro Ser Ala Asp Trp His Gly
                500                   505                   510
```

Phe Gly Asp Ile Ala Glu Asp Tyr Val Leu Leu Asp Pro Ile Lys Val
           515                 520                 525

Thr Leu Thr Thr Pro Gly Leu Ser Ala Gly Gly Lys Leu Ser Glu Gln
    530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Val Thr Glu Leu Leu Glu
                580                 585                 590

Phe Lys Arg Cys Tyr Asp Ala Asn Leu Pro Leu Leu Asp Val Leu Pro
            595                 600                 605

Ser Val Ala Gln Ala Gly Gly Lys Arg Tyr Asn Gly Val Gly Leu Arg
        610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
                645                 650                 655

Pro Ser Glu Ala Tyr Asp Lys Leu Val Arg Gly Glu Val Glu Ala Val
            660                 665                 670

Pro Ile Ala Arg Leu Glu Gly Arg Ile Ala Ala Val Met Leu Val Pro
        675                 680                 685

Tyr Pro Pro Gly Ile Pro Leu Ile Met Pro Gly Glu Arg Phe Thr Glu
    690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
            740                 745                 750

<210> SEQ ID NO 17
<211> LENGTH: 751
<212> TYPE: PRT
<213> ORGANISM: Artificial Sequence
<220> FEATURE:
<223> OTHER INFORMATION: synthetic

<400> SEQUENCE: 17

Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
                20                  25                  30

Leu Glu Gln Asp Gly Phe Ser Ile Leu Ser Thr Ala Ser Ser Ala Glu
            35                  40                  45

Gly Arg Ile Val Ala Ser Thr His His Gly Leu Ala Cys Ile Leu Val
        50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Ser Met
            100                 105                 110

Ala Asp Leu His Gln Leu Arg Gly Ile Leu Tyr Leu Phe Glu Asp Thr
        115                 120                 125

```
Val Pro Phe Leu Ala Arg Gln Val Ala Arg Ala Ala Arg Asn Tyr Leu
    130                 135                 140

Ala Gly Leu Leu Pro Pro Phe Phe Arg Ala Leu Val Glu His Thr Ala
145                 150                 155                 160

Gln Ser Asn Tyr Ser Trp His Thr Pro Gly His Gly Gly Gly Val Ala
                165                 170                 175

Tyr Arg Lys Ser Pro Val Gly Gln Ala Phe His Gln Phe Phe Gly Glu
                180                 185                 190

Asn Thr Leu Arg Ser Asp Leu Ser Val Ser Val Pro Glu Leu Gly Ser
                195                 200                 205

Leu Leu Asp His Thr Gly Pro Leu Ala Glu Ala Glu Asp Arg Ala Ala
    210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
                245                 250                 255

Val Leu Val Asp Arg Asn Cys His Asn Ser Ile Leu His Ser Ile Ile
                260                 265                 270

Met Thr Gly Ala Ile Pro Leu Tyr Leu Thr Pro Glu Arg Asn Glu Leu
    275                 280                 285

Gly Ile Ile Gly Pro Ile Pro Leu Ser Glu Phe Ser Lys Gln Ser Ile
    290                 295                 300

Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Thr Leu Gly Asp Ser Val Glu Val Leu
                340                 345                 350

His Phe Asp Glu Ala Trp Tyr Ala Tyr Ala Ala Phe His Glu Phe Tyr
    355                 360                 365

Asp Gly Arg Tyr Gly Met Gly Thr Ser Arg Ser Glu Glu Gly Pro Leu
    370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
                405                 410                 415

Ala Arg Phe Asn Glu Ala Phe Met Met His Ile Ser Thr Ser Pro Gln
                420                 425                 430

Tyr Gly Ile Ile Ala Ser Leu Asp Val Ala Ser Ala Met Met Glu Gly
    435                 440                 445

Pro Ala Gly Arg Ser Leu Ile Gln Glu Thr Phe Asp Glu Ala Leu Ser
450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
                485                 490                 495

Val Gly Thr His Asp Trp Val Leu Glu Pro Ser Ala Asp Trp His Gly
                500                 505                 510

Phe Gly Asp Ile Ala Glu Asp Tyr Val Leu Leu Asp Pro Ile Lys Val
    515                 520                 525

Thr Leu Thr Thr Pro Gly Leu Ser Ala Gly Gly Lys Leu Ser Glu Gln
530                 535                 540
```

```
Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Val Thr Glu Leu Leu Glu
                580                 585                 590

Phe Lys Arg Cys Tyr Asp Ala Asn Leu Pro Leu Leu Asp Val Leu Pro
            595                 600                 605

Ser Val Ala Gln Ala Gly Gly Lys Arg Tyr Asn Gly Val Gly Leu Arg
            610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
                645                 650                 655

Pro Ser Glu Ala Tyr Asp Lys Leu Val Arg Gly Val Glu Ala Val
            660                 665                 670

Pro Ile Ala Arg Leu Glu Gly Arg Ile Ala Ala Val Met Leu Val Pro
            675                 680                 685

Tyr Pro Pro Gly Ile Pro Leu Ile Met Pro Gly Glu Arg Phe Thr Glu
690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
            740                 745                 750

<210> SEQ ID NO 18
<211> LENGTH: 751
<212> TYPE: PRT
<213> ORGANISM: Artificial Sequence
<220> FEATURE:
<223> OTHER INFORMATION: synthetic

<400> SEQUENCE: 18

Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
                20                  25                  30

Leu Glu Gln Asp Gly Phe Ser Ile Leu Ser Thr Ala Ser Ser Ala Glu
            35                  40                  45

Gly Arg Ile Val Ala Ser Thr His Gly Leu Ala Cys Ile Leu Val
        50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Cys Met
                100                 105                 110

Ala Asp Leu His Gln Leu Arg Gly Ile Leu Tyr Leu Phe Glu Asp Thr
            115                 120                 125

Val Pro Phe Leu Ala Arg Gln Val Ala Arg Ala Arg Asn Tyr Leu
        130                 135                 140

Ala Gly Leu Leu Pro Pro Phe Phe Arg Ala Leu Val Glu His Thr Ala
145                 150                 155                 160
```

```
Gln Ser Asn Tyr Ser Trp His Thr Pro Gly His Gly Gly Val Ala
            165                 170                 175

Tyr Arg Lys Ser Pro Val Gly Gln Ala Phe His Gln Phe Phe Gly Glu
        180                 185                 190

Asn Thr Leu Arg Ser Asp Leu Ser Val Ser Val Pro Glu Leu Gly Ser
        195                 200                 205

Leu Leu Asp His Thr Gly Pro Leu Ala Glu Ala Glu Asp Arg Ala Ala
210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
            245                 250                 255

Val Leu Val Asp Arg Thr Cys His Lys Ser Ile Leu His Ser Ile Ile
            260                 265                 270

Met Thr Gly Ala Ile Pro Leu Tyr Leu Thr Pro Glu Arg Asn Glu Leu
        275                 280                 285

Gly Ile Ile Gly Pro Ile Pro Leu Ser Glu Phe Ser Lys Gln Ser Ile
        290                 295                 300

Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
            325                 330                 335

Asn Ala Glu Leu Ile Lys Gln Thr Leu Gly Asp Ser Val Glu Val Leu
            340                 345                 350

His Phe Asp Glu Ala Trp Tyr Ala Tyr Ala Ala Phe His Glu Phe Tyr
        355                 360                 365

Asp Gly Arg Tyr Gly Met Gly Thr Ser Arg Ser Glu Glu Gly Pro Leu
        370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
            405                 410                 415

Ala Arg Phe Asn Glu Ala Phe Met Met His Ile Ser Thr Ser Pro Gln
            420                 425                 430

Tyr Gly Ile Ile Ala Ser Leu Asp Val Ala Ser Ala Met Met Glu Gly
        435                 440                 445

Pro Ala Gly Arg Ser Leu Ile Gln Glu Thr Phe Asp Glu Ala Leu Ser
450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
            485                 490                 495

Val Gly Thr His Asp Trp Val Leu Glu Pro Ser Ala Asp Trp His Gly
        500                 505                 510

Phe Gly Asp Ile Ala Glu Asp Tyr Val Leu Leu Asp Pro Ile Lys Val
        515                 520                 525

Thr Leu Thr Thr Pro Gly Leu Ser Ala Gly Gly Lys Leu Ser Glu Gln
530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
            565                 570                 575

Gly Ile Thr Lys Gly Lys Trp Ser Thr Leu Val Thr Glu Leu Leu Glu
```

```
            580                 585                 590
Phe Lys Arg Cys Tyr Asp Ala Asn Leu Pro Leu Leu Asp Val Leu Pro
            595                 600                 605

Ser Val Ala Gln Ala Gly Gly Lys Arg Tyr Asn Gly Val Gly Leu Arg
    610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
                645                 650                 655

Pro Ser Glu Ala Tyr Asp Lys Leu Val Arg Gly Glu Val Glu Ala Val
            660                 665                 670

Pro Ile Ala Arg Leu Glu Gly Arg Ile Ala Ala Val Met Leu Val Pro
        675                 680                 685

Tyr Pro Pro Gly Ile Pro Leu Ile Met Pro Gly Glu Arg Phe Thr Glu
        690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
            740                 745                 750
```

<210> SEQ ID NO 19
<211> LENGTH: 751
<212> TYPE: PRT
<213> ORGANISM: Artificial Sequence
<220> FEATURE:
<223> OTHER INFORMATION: synthetic

<400> SEQUENCE: 19

```
Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
                20                  25                  30

Leu Glu Gln Asp Gly Phe Ser Ile Leu Ser Thr Ala Ser Ser Ala Glu
            35                  40                  45

Gly Arg Ile Val Ala Ser Thr His His Gly Leu Ala Cys Ile Leu Val
        50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Cys Met
            100                 105                 110

Ala Asp Leu His Gln Leu Arg Gly Ile Leu Tyr Leu Phe Glu Asp Thr
        115                 120                 125

Val Pro Phe Leu Ala Arg Gln Val Ala Arg Ala Arg Asn Tyr Leu
    130                 135                 140

Ala Gly Leu Leu Pro Pro Phe Phe Arg Ala Leu Val Glu His Thr Ala
145                 150                 155                 160

Gln Ser Asn Tyr Ser Trp His Thr Pro Gly His Gly Gly Val Ala
                165                 170                 175

Tyr Arg Lys Ser Pro Val Gly Gln Ala Phe His Gln Phe Phe Gly Glu
            180                 185                 190

Asn Thr Leu Arg Ser Asp Leu Ser Val Ser Val Pro Glu Leu Gly Ser
```

```
              195                 200                 205
Leu Leu Asp His Thr Gly Pro Leu Ala Glu Ala Glu Asp Arg Ala Ala
210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
                245                 250                 255

Val Leu Val Asp Arg Asn Cys His Asn Ser Ile Leu His Ser Ile Ile
                260                 265                 270

Met Thr Gly Ala Ile Pro Leu Tyr Leu Thr Pro Glu Arg Asn Glu Leu
                275                 280                 285

Gly Ile Ile Gly Pro Ile Pro Leu Ser Glu Phe Ser Lys Gln Ser Ile
                290                 295                 300

Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Thr Leu Gly Asp Ser Val Glu Val Leu
                340                 345                 350

His Phe Asp Glu Ala Trp Tyr Ala Tyr Ala Ala Phe His Glu Phe Tyr
                355                 360                 365

Asp Gly Arg Tyr Gly Met Gly Thr Ser Arg Ser Glu Glu Gly Pro Leu
370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
                405                 410                 415

Ala Arg Phe Asn Glu Ala Phe Met Met His Ile Ser Thr Ser Pro Gln
                420                 425                 430

Tyr Gly Ile Ile Ala Ser Leu Asp Val Ala Ser Ala Met Met Glu Gly
                435                 440                 445

Pro Ala Gly Arg Ser Leu Ile Gln Glu Thr Phe Asp Glu Ala Leu Ser
450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
                485                 490                 495

Val Gly Thr His Asp Trp Val Leu Glu Pro Ser Ala Asp Trp His Gly
                500                 505                 510

Phe Gly Asp Ile Ala Glu Asp Tyr Val Leu Leu Asp Pro Ile Lys Val
                515                 520                 525

Thr Leu Thr Thr Pro Gly Leu Ser Ala Gly Gly Lys Leu Ser Glu Gln
                530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Val Thr Glu Leu Leu Glu
                580                 585                 590

Phe Lys Arg Cys Tyr Asp Ala Asn Leu Pro Leu Leu Asp Val Leu Pro
                595                 600                 605

Ser Val Ala Gln Ala Gly Gly Lys Arg Tyr Asn Gly Val Gly Leu Arg
610                 615                 620
```

```
Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
            645                 650                 655

Pro Ser Glu Ala Tyr Asp Lys Leu Val Arg Gly Glu Val Glu Ala Val
        660                 665                 670

Pro Ile Ala Arg Leu Glu Gly Arg Ile Ala Ala Val Met Leu Val Pro
    675                 680                 685

Tyr Pro Pro Gly Ile Pro Leu Ile Met Pro Gly Glu Arg Phe Thr Glu
690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
            725                 730                 735

Asp Gly Pro Ser Gly Arg Cys Tyr Thr Val Glu Cys Ile Lys Glu
        740                 745                 750
```

<210> SEQ ID NO 20
<211> LENGTH: 751
<212> TYPE: PRT
<213> ORGANISM: Artificial Sequence
<220> FEATURE:
<223> OTHER INFORMATION: synthetic

<400> SEQUENCE: 20

```
Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
            20                  25                  30

Leu Glu Gln Asp Gly Phe Ser Ile Leu Ser Thr Ala Ser Ser Ala Glu
        35                  40                  45

Gly Arg Ile Val Ala Ser Thr His His Gly Leu Ala Cys Ile Leu Val
    50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Ser Met
            100                 105                 110

Ala Asp Leu His Gln Leu Arg Gly Ile Leu Tyr Leu Phe Glu Asp Thr
        115                 120                 125

Val Pro Phe Leu Ala Arg Gln Val Ala Arg Ala Ala Arg Asn Tyr Leu
    130                 135                 140

Ala Gly Leu Leu Pro Pro Phe Arg Ala Leu Val Glu His Thr Ala
145                 150                 155                 160

Gln Ser Asn Tyr Ser Trp His Thr Pro Gly His Gly Gly Val Ala
                165                 170                 175

Tyr Arg Lys Ser Pro Val Gly Gln Ala Phe His Gln Phe Gly Glu
            180                 185                 190

Asn Thr Leu Arg Ser Asp Leu Ser Val Ser Pro Glu Leu Gly Ser
        195                 200                 205

Leu Leu Asp His Thr Gly Pro Leu Ala Glu Ala Glu Asp Arg Ala Ala
    210                 215                 220

Arg Asn Phe Gly Ala Asp His Thr Phe Phe Val Ile Asn Gly Thr Ser
225                 230                 235                 240
```

```
Thr Ala Asn Lys Ile Val Trp His Ser Met Val Gly Arg Glu Asp Leu
            245                 250                 255

Val Leu Val Asp Arg Thr Cys His Asn Ser Ile Leu His Ser Ile Ile
            260                 265                 270

Met Thr Gly Ala Ile Pro Leu Tyr Leu Thr Pro Glu Arg Asn Glu Leu
            275                 280                 285

Gly Ile Ile Gly Pro Ile Pro Leu Ser Glu Phe Ser Lys Gln Ser Ile
            290                 295                 300

Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
            325                 330                 335

Asn Ala Glu Leu Ile Lys Gln Thr Leu Gly Asp Ser Val Glu Val Leu
            340                 345                 350

His Phe Asp Glu Ala Trp Tyr Ala Tyr Ala Ala Phe His Glu Phe Tyr
            355                 360                 365

Asp Gly Arg Tyr Gly Met Gly Thr Ser Arg Ser Glu Glu Gly Pro Leu
            370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
            405                 410                 415

Ala Arg Phe Asn Glu Ala Phe Met Met His Ile Ser Thr Ser Pro Gln
            420                 425                 430

Tyr Gly Ile Ile Ala Ser Leu Asp Val Ala Ser Ala Met Met Glu Gly
            435                 440                 445

Pro Ala Gly Arg Ser Leu Ile Gln Glu Thr Phe Asp Glu Ala Leu Ser
450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
            485                 490                 495

Val Gly Thr His Asp Trp Val Leu Glu Pro Ser Ala Asp Trp His Gly
            500                 505                 510

Phe Gly Asp Ile Ala Glu Asp Tyr Val Leu Leu Asp Pro Ile Lys Val
            515                 520                 525

Thr Leu Thr Thr Pro Gly Leu Ser Ala Gly Gly Lys Leu Ser Glu Gln
530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
            565                 570                 575

Gly Ile Thr Lys Gly Lys Trp Ser Thr Leu Val Thr Glu Leu Leu Glu
            580                 585                 590

Phe Lys Arg Cys Tyr Asp Ala Asn Leu Pro Leu Leu Asp Val Leu Pro
            595                 600                 605

Ser Val Ala Gln Ala Gly Gly Lys Arg Tyr Asn Gly Val Gly Leu Arg
            610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
            645                 650                 655
```

```
Pro Ser Glu Ala Tyr Asp Lys Leu Val Arg Gly Glu Val Glu Ala Val
                660                 665                 670

Pro Ile Ala Arg Leu Glu Gly Arg Ile Ala Ala Val Met Leu Val Pro
            675                 680                 685

Tyr Pro Pro Gly Ile Pro Leu Ile Met Pro Gly Glu Arg Phe Thr Glu
        690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
            740                 745                 750

<210> SEQ ID NO 21
<211> LENGTH: 751
<212> TYPE: PRT
<213> ORGANISM: Artificial Sequence
<220> FEATURE:
<223> OTHER INFORMATION: synthetic

<400> SEQUENCE: 21

Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
                20                  25                  30

Leu Glu Gln Asp Gly Phe Ser Ile Leu Ser Thr Ala Ser Ser Ala Glu
            35                  40                  45

Gly Arg Ile Val Ala Ser Thr His His Gly Leu Ala Cys Ile Leu Val
50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Cys Met
            100                 105                 110

Ala Asp Leu His Gln Leu Arg Gly Ile Leu Tyr Leu Phe Glu Asp Thr
        115                 120                 125

Val Pro Phe Leu Ala Arg Gln Val Ala Arg Ala Arg Asn Tyr Leu
130                 135                 140

Ala Gly Leu Leu Pro Pro Phe Phe Arg Ala Leu Val Glu His Thr Ala
145                 150                 155                 160

Gln Ser Asn Tyr Ser Trp His Thr Pro Gly His Gly Gly Gly Val Ala
                165                 170                 175

Tyr Arg Lys Ser Pro Val Gly Gln Ala Phe His Gln Phe Phe Gly Glu
            180                 185                 190

Asn Thr Leu Arg Ser Asp Leu Ser Val Ser Val Pro Glu Leu Gly Ser
        195                 200                 205

Leu Leu Asp His Thr Gly Pro Leu Ala Glu Ala Glu Asp Arg Ala Ala
                210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
                245                 250                 255

Val Leu Val Asp Arg Thr Cys His Asn Ser Ile Leu His Ser Ile Ile
            260                 265                 270
```

```
Met Thr Gly Ala Ile Pro Leu Tyr Leu Thr Pro Glu Arg Asn Glu Leu
            275                 280                 285
Gly Ile Ile Gly Pro Ile Pro Leu Ser Glu Phe Ser Lys Gln Ser Ile
290                 295                 300
Ala Ala Lys Ile Ala Ala Ser Pro Leu Ala Arg Gly Arg Glu Pro Lys
305                 310                 315                 320
Val Lys Leu Ala Val Val Thr Asn Ser Thr Tyr Asp Gly Leu Cys Tyr
            325                 330                 335
Asn Ala Glu Leu Ile Lys Gln Thr Leu Gly Asp Ser Val Glu Val Leu
            340                 345                 350
His Phe Asp Glu Ala Trp Tyr Ala Tyr Ala Ala Phe His Glu Phe Tyr
            355                 360                 365
Asp Gly Arg Tyr Gly Met Gly Thr Ser Arg Ser Glu Glu Gly Pro Leu
            370                 375                 380
Val Phe Ala Thr His Ser Thr His Lys Met Leu Ala Ala Phe Ser Gln
385                 390                 395                 400
Ala Ser Met Ile His Val Gln Asp Gly Gly Thr Arg Lys Leu Asp Val
            405                 410                 415
Ala Arg Phe Asn Glu Ala Phe Met Met His Ile Ser Thr Ser Pro Gln
            420                 425                 430
Tyr Gly Ile Ile Ala Ser Leu Asp Val Ala Ser Ala Met Met Glu Gly
            435                 440                 445
Pro Ala Gly Arg Ser Leu Ile Gln Glu Thr Phe Asp Glu Ala Leu Ser
            450                 455                 460
Phe Arg Arg Ala Leu Ala Asn Val Arg Gln Asn Leu Asp Arg Asn Asp
465                 470                 475                 480
Trp Trp Phe Gly Val Trp Gln Pro Glu Gln Val Glu Gly Thr Asp Gln
            485                 490                 495
Val Gly Thr His Asp Trp Val Leu Glu Pro Ser Ala Asp Trp His Gly
            500                 505                 510
Phe Gly Asp Ile Ala Glu Asp Tyr Val Leu Leu Asp Pro Ile Lys Val
            515                 520                 525
Thr Leu Thr Thr Pro Gly Leu Ser Ala Gly Gly Lys Leu Ser Glu Gln
530                 535                 540
Gly Ile Pro Ala Ala Ile Val Ser Arg Phe Leu Trp Glu Arg Gly Leu
545                 550                 555                 560
Val Val Glu Lys Thr Gly Leu Tyr Ser Phe Leu Val Leu Phe Ser Met
            565                 570                 575
Gly Ile Thr Lys Gly Lys Trp Ser Thr Leu Val Thr Glu Leu Leu Glu
            580                 585                 590
Phe Lys Arg Cys Tyr Asp Ala Asn Leu Pro Leu Leu Asp Val Leu Pro
            595                 600                 605
Ser Val Ala Gln Ala Gly Gly Lys Arg Tyr Asn Gly Val Gly Leu Arg
            610                 615                 620
Asp Leu Ser Asp Ala Met His Ala Ser Tyr Arg Asp Asn Ala Thr Ala
625                 630                 635                 640
Lys Ala Met Lys Arg Met Tyr Thr Val Leu Pro Glu Val Ala Met Arg
            645                 650                 655
Pro Ser Glu Ala Tyr Asp Lys Leu Val Arg Gly Glu Val Glu Ala Val
            660                 665                 670
Pro Ile Ala Arg Leu Glu Gly Arg Ile Ala Ala Val Met Leu Val Pro
            675                 680                 685
Tyr Pro Pro Gly Ile Pro Leu Ile Met Pro Gly Glu Arg Phe Thr Glu
```

```
                690             695             700
Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
                740                 745                 750

<210> SEQ ID NO 22
<211> LENGTH: 367
<212> TYPE: PRT
<213> ORGANISM: Escherichia coli

<400> SEQUENCE: 22

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
                20                  25                  30

Val Phe Phe Ser Thr Ser Gln Leu Gly Gln Ala Ala Pro Ser Phe Gly
            35                  40                  45

Gly Thr Thr Gly Thr Leu Gln Asp Ala Phe Asp Leu Glu Ala Leu Lys
50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
                100                 105                 110

Pro Val Asn Gln Asp Val Ile Thr Asp Gly Leu Asn Asn Gly Ile Arg
            115                 120                 125

Thr Phe Val Gly Gly Asn Cys Thr Val Ser Leu Met Leu Met Ser Leu
130                 135                 140

Gly Gly Leu Phe Ala Asn Asp Leu Val Asp Trp Val Ser Val Ala Thr
145                 150                 155                 160

Tyr Gln Ala Ala Ser Gly Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
            195                 200                 205

Arg Ser Gly Glu Leu Pro Val Asp Asn Phe Gly Val Pro Leu Ala Gly
210                 215                 220

Ser Leu Ile Pro Trp Ile Asp Lys Gln Leu Asp Asn Gly Gln Ser Arg
225                 230                 235                 240

Glu Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
            275                 280                 285

Pro Thr Val Glu Glu Leu Leu Ala Ala His Asn Pro Trp Ala Lys Val
        290                 295                 300

Val Pro Asn Asp Arg Glu Ile Thr Met Arg Glu Leu Thr Pro Ala Ala
305                 310                 315                 320
```

```
Val Thr Gly Thr Leu Thr Thr Pro Val Gly Arg Leu Arg Lys Leu Asn
            325                 330                 335

Met Gly Pro Glu Phe Leu Ser Ala Phe Thr Val Gly Asp Gln Leu Leu
        340                 345                 350

Trp Gly Ala Ala Glu Pro Leu Arg Arg Met Leu Arg Gln Leu Ala
    355                 360                 365

<210> SEQ ID NO 23
<211> LENGTH: 273
<212> TYPE: PRT
<213> ORGANISM: Escherichia coli

<400> SEQUENCE: 23

Met His Asp Ala Asn Ile Arg Val Ala Ile Ala Gly Ala Gly Gly Arg
1               5                   10                  15

Met Gly Arg Gln Leu Ile Gln Ala Ala Leu Ala Leu Glu Gly Val Gln
            20                  25                  30

Leu Gly Ala Ala Leu Glu Arg Glu Gly Ser Ser Leu Leu Gly Ser Asp
        35                  40                  45

Ala Gly Glu Leu Ala Gly Ala Gly Lys Thr Gly Val Thr Val Gln Ser
    50                  55                  60

Ser Leu Asp Ala Val Lys Asp Asp Phe Asp Val Phe Ile Asp Phe Thr
65                  70                  75                  80

Arg Pro Glu Gly Thr Leu Asn His Leu Ala Phe Cys Arg Gln His Gly
                85                  90                  95

Lys Gly Met Val Ile Gly Thr Thr Gly Phe Asp Glu Ala Gly Lys Gln
            100                 105                 110

Ala Ile Arg Asp Ala Ala Ala Asp Ile Ala Ile Val Phe Ala Ala Asn
        115                 120                 125

Phe Ser Val Gly Val Asn Val Met Leu Lys Leu Leu Glu Lys Ala Ala
    130                 135                 140

Lys Val Met Gly Asp Tyr Thr Asp Ile Glu Ile Ile Glu Ala His His
145                 150                 155                 160

Arg His Lys Val Asp Ala Pro Ser Gly Thr Ala Leu Ala Met Gly Glu
                165                 170                 175

Ala Ile Ala His Ala Leu Asp Lys Asp Leu Lys Asp Cys Ala Val Tyr
            180                 185                 190

Ser Arg Glu Gly His Thr Gly Glu Arg Val Pro Gly Thr Ile Gly Phe
        195                 200                 205

Ala Thr Val Arg Ala Gly Asp Ile Val Gly Glu His Thr Ala Met Phe
    210                 215                 220

Ala Asp Ile Gly Glu Arg Leu Glu Ile Thr His Lys Ala Ser Ser Arg
225                 230                 235                 240

Met Thr Phe Ala Asn Gly Ala Val Arg Ser Ala Leu Trp Leu Ser Gly
                245                 250                 255

Lys Glu Ser Gly Leu Phe Asp Met Arg Asp Val Leu Asp Leu Asn Asn
            260                 265                 270

Leu

<210> SEQ ID NO 24
<211> LENGTH: 274
<212> TYPE: PRT
<213> ORGANISM: Escherichia coli

<400> SEQUENCE: 24

Met Gln Gln Leu Gln Asn Ile Ile Glu Thr Ala Phe Glu Arg Arg Ala
```

-continued

```
               1               5                   10                  15
            Glu Ile Thr Pro Ala Asn Ala Asp Thr Val Thr Arg Glu Ala Val Asn
                               20                  25                  30
            Gln Val Ile Ala Leu Leu Asp Ser Gly Ala Leu Arg Val Ala Glu Lys
                               35                  40                  45
            Ile Asp Gly Gln Trp Val Thr His Gln Trp Leu Lys Lys Ala Val Leu
                               50                  55                  60
            Leu Ser Phe Arg Ile Asn Asp Asn Gln Val Ile Glu Gly Ala Glu Ser
            65                  70                  75                  80
            Arg Tyr Phe Asp Lys Val Pro Met Lys Phe Ala Asp Tyr Asp Glu Ala
                               85                  90                  95
            Arg Phe Gln Lys Glu Gly Phe Arg Val Val Pro Ala Ala Val Arg
                               100                 105                 110
            Gln Gly Ala Phe Ile Ala Arg Asn Thr Val Leu Met Pro Ser Tyr Val
                               115                 120                 125
            Asn Ile Gly Ala Tyr Val Asp Glu Gly Thr Met Val Asp Thr Trp Ala
                               130                 135                 140
            Thr Val Gly Ser Cys Ala Gln Ile Gly Lys Asn Val His Leu Ser Gly
            145                 150                 155                 160
            Gly Val Gly Ile Gly Gly Val Leu Glu Pro Leu Gln Ala Asn Pro Thr
                               165                 170                 175
            Ile Ile Glu Asp Asn Cys Phe Ile Gly Ala Arg Ser Glu Val Val Glu
                               180                 185                 190
            Gly Val Ile Val Glu Glu Gly Ser Val Ile Ser Met Gly Val Tyr Ile
                               195                 200                 205
            Gly Gln Ser Thr Arg Ile Tyr Asp Arg Glu Thr Gly Glu Ile His Tyr
                               210                 215                 220
            Gly Arg Val Pro Ala Gly Ser Val Val Ser Gly Asn Leu Pro Ser
            225                 230                 235                 240
            Lys Asp Gly Lys Tyr Ser Leu Tyr Cys Ala Val Ile Val Lys Lys Val
                               245                 250                 255
            Asp Ala Lys Thr Arg Gly Lys Val Gly Ile Asn Glu Leu Leu Arg Thr
                               260                 265                 270
            Ile Asp

<210> SEQ ID NO 25
<211> LENGTH: 396
<212> TYPE: PRT
<213> ORGANISM: Escherichia coli

<400> SEQUENCE: 25

Met Phe Glu Asn Ile Thr Ala Ala Pro Ala Asp Pro Ile Leu Gly Leu
            1                   5                   10                  15
            Ala Asp Leu Phe Arg Ala Asp Glu Arg Pro Gly Lys Ile Asn Leu Gly
                               20                  25                  30
            Ile Gly Val Tyr Lys Asp Glu Thr Gly Lys Thr Pro Val Leu Thr Ser
                               35                  40                  45
            Val Lys Lys Ala Glu Gln Tyr Leu Leu Glu Asn Glu Thr Thr Lys Asn
                               50                  55                  60
            Tyr Leu Gly Ile Asp Gly Ile Pro Glu Phe Gly Arg Cys Thr Gln Glu
            65                  70                  75                  80
            Leu Leu Phe Gly Lys Gly Ser Ala Leu Ile Asn Asp Lys Arg Ala Arg
                               85                  90                  95
            Thr Ala Gln Thr Pro Gly Gly Thr Gly Ala Leu Arg Val Ala Ala Asp
```

-continued

```
               100                 105                 110
Phe Leu Ala Lys Asn Thr Ser Val Lys Arg Val Trp Val Ser Asn Pro
            115                 120                 125

Ser Trp Pro Asn His Lys Ser Val Phe Asn Ser Ala Gly Leu Glu Val
        130                 135                 140

Arg Glu Tyr Ala Tyr Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
            180                 185                 190

Gln Trp Gln Thr Leu Ala Gln Leu Ser Val Glu Lys Gly Trp Leu Pro
        195                 200                 205

Leu Phe Asp Phe Ala Tyr Gln Gly Phe Ala Arg Gly Leu Glu Glu Asp
    210                 215                 220

Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                245                 250                 255

Ala Cys Thr Leu Val Ala Ala Asp Ser Glu Thr Val Asp Arg Ala Phe
            260                 265                 270

Ser Gln Met Lys Ala Ala Ile Arg Ala Asn Tyr Ser Asn Pro Pro Ala
        275                 280                 285

His Gly Ala Ser Val Val Ala Thr Ile Leu Ser Asn Asp Ala Leu Arg
    290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Lys Gly Ala Asn Arg
                325                 330                 335

Asp Phe Ser Phe Ile Ile Lys Gln Asn Gly Met Phe Ser Phe Ser Gly
            340                 345                 350

Leu Thr Lys Glu Gln Val Leu Arg Leu Arg Glu Glu Phe Gly Val Tyr
        355                 360                 365

Ala Val Ala Ser Gly Arg Val Asn Val Ala Gly Met Thr Pro Asp Asn
    370                 375                 380

Met Ala Pro Leu Cys Glu Ala Ile Val Ala Val Leu
385                 390                 395
```

<210> SEQ ID NO 26
<211> LENGTH: 449
<212> TYPE: PRT
<213> ORGANISM: Artificial Sequence
<220> FEATURE:
<223> OTHER INFORMATION: synthetic

<400> SEQUENCE: 26

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
```

```
                65                  70                  75                  80
            Pro Asn Val Ile Arg Glu Glu Ile Glu Arg Leu Leu Glu Asn Ile Thr
                                85                  90                  95
            Val Leu Ala Glu Ala Ala Ala Leu Ala Thr Ser Pro Ala Leu Thr Asp
                            100                 105                 110
            Glu Leu Val Ser His Gly Leu Met Ser Thr Leu Leu Phe Val Glu
                        115                 120                 125
            Ile Leu Arg Glu Arg Asp Val Gln Ala Gln Trp Phe Asp Val Arg Lys
                    130                 135                 140
            Val Met Arg Thr Asn Asp Arg Phe Gly Arg Ala Glu Pro Asp Ile Ala
            145                 150                 155                 160
            Ala Leu Ala Glu Leu Ala Ala Leu Gln Leu Leu Pro Arg Leu Asn Glu
                                165                 170                 175
            Gly Leu Val Ile Thr Gln Gly Phe Ile Gly Ser Glu Asn Lys Gly Arg
                            180                 185                 190
            Thr Thr Thr Leu Gly Arg Gly Gly Ser Asp Tyr Thr Ala Ala Leu Leu
                        195                 200                 205
            Ala Glu Ala Leu His Ala Ser Arg Val Asp Ile Trp Thr Asp Val Pro
                    210                 215                 220
            Gly Ile Tyr Thr Thr Asp Pro Arg Val Val Ser Ala Ala Lys Arg Ile
            225                 230                 235                 240
            Asp Glu Ile Ala Phe Ala Glu Ala Ala Glu Met Ala Thr Phe Gly Ala
                                245                 250                 255
            Lys Val Leu His Pro Ala Thr Leu Leu Pro Ala Val Arg Ser Asp Ile
                            260                 265                 270
            Pro Val Phe Val Gly Ser Ser Lys Asp Pro Arg Ala Gly Gly Thr Leu
                        275                 280                 285
            Val Cys Asn Lys Thr Glu Asn Pro Pro Leu Phe Arg Ala Leu Ala Leu
                    290                 295                 300
            Arg Arg Asn Gln Thr Leu Leu Thr Leu His Ser Leu Asn Ile Leu His
            305                 310                 315                 320
            Ser Arg Asp Phe Leu Ala Glu Val Phe Gly Ile Leu Ala Arg His Asn
                                325                 330                 335
            Ile Ser Val Asp Leu Ile Thr Thr Ser Glu Val Ser Val Ala Leu Thr
                            340                 345                 350
            Leu Asp Thr Thr Gly Ser Thr Ser Thr Gly Asp Thr Leu Leu Thr Gln
                        355                 360                 365
            Ser Leu Leu Met Glu Leu Ser Ala Leu Cys Arg Val Glu Val Glu Glu
                    370                 375                 380
            Gly Leu Ala Leu Val Ala Leu Ile Gly Asn Asp Leu Ser Lys Ala Cys
            385                 390                 395                 400
            Gly Val Gly Lys Glu Val Phe Gly Val Leu Glu Pro Phe Asn Ile Arg
                                405                 410                 415
            Met Ile Cys Tyr Gly Ala Ser Ser His Asn Leu Cys Phe Leu Val Pro
                            420                 425                 430
            Gly Glu Asp Ala Glu Gln Val Val Gln Lys Leu His Ser Asn Leu Phe
                        435                 440                 445
            Glu

<210> SEQ ID NO 27
<211> LENGTH: 449
<212> TYPE: PRT
<213> ORGANISM: Artificial Sequence
<220> FEATURE:
```

<223> OTHER INFORMATION: synthetic

<400> SEQUENCE: 27

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Ile Glu Arg Leu Leu Glu Asn Ile Thr
                85                  90                  95

Val Leu Ala Glu Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Met Ser Glu Val Ser Val Ala Leu Ile
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400
```

```
Gly Val Gly Lys Glu Val Phe Gly Val Leu Glu Pro Phe Asn Ile Arg
            405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
            435                 440                 445

Glu
```

```
<210> SEQ ID NO 28
<211> LENGTH: 425
<212> TYPE: PRT
<213> ORGANISM: Streptomyces lividans

<400> SEQUENCE: 28
```

```
Met Gly Leu Val Val Gln Lys Tyr Gly Gly Ser Ser Val Ala Asp Ala
1               5                   10                  15

Glu Gly Ile Lys Arg Val Ala Lys Arg Ile Val Glu Ala Lys Lys Asn
            20                  25                  30

Gly Asn Gln Val Val Ala Val Ser Ala Met Gly Asp Thr Thr Asp
            35                  40                  45

Glu Leu Ile Asp Leu Ala Glu Gln Val Ser Pro Ile Pro Ala Gly Arg
    50                  55                  60

Glu Leu Asp Met Leu Leu Thr Ala Gly Glu Arg Ile Ser Met Ala Leu
65                  70                  75                  80

Leu Ala Met Ala Ile Lys Asn Leu Gly His Glu Ala Gln Ser Phe Thr
                85                  90                  95

Gly Ser Gln Ala Gly Val Ile Thr Asp Ser Val His Asn Lys Ala Arg
            100                 105                 110

Ile Ile Asp Val Thr Pro Gly Arg Ile Arg Thr Ser Val Asp Glu Gly
            115                 120                 125

Asn Val Ala Ile Val Ala Gly Phe Gln Gly Val Ser Gln Asp Ser Lys
        130                 135                 140

Asp Ile Thr Thr Leu Gly Arg Gly Gly Ser Asp Thr Thr Ala Val Ala
145                 150                 155                 160

Leu Ala Ala Ala Leu Asp Ala Asp Val Cys Glu Ile Tyr Thr Asp Val
                165                 170                 175

Asp Gly Val Phe Thr Ala Asp Pro Arg Val Val Pro Lys Ala Lys Lys
            180                 185                 190

Ile Asp Trp Ile Ser Phe Glu Asp Met Leu Glu Leu Ala Ala Ser Gly
        195                 200                 205

Ser Lys Val Leu Leu His Arg Cys Val Glu Tyr Ala Arg Arg Tyr Asn
    210                 215                 220

Ile Pro Ile His Val Arg Ser Ser Phe Ser Gly Leu Gln Gly Thr Trp
225                 230                 235                 240

Val Ser Ser Glu Pro Ile Lys Gln Gly Glu Lys His Val Glu Gln Ala
                245                 250                 255

Leu Ile Ser Gly Val Ala His Asp Thr Ser Glu Ala Lys Val Thr Val
            260                 265                 270

Val Gly Val Pro Asp Lys Pro Gly Glu Ala Ala Ile Phe Arg Ala
            275                 280                 285

Ile Ala Asp Ala Gln Val Asn Ile Asp Met Val Val Gln Asn Val Ser
        290                 295                 300

Ala Ala Ser Thr Gly Leu Thr Asp Ile Ser Phe Thr Leu Pro Lys Ser
305                 310                 315                 320
```

Glu Gly Arg Lys Ala Ile Asp Ala Leu Glu Lys Asn Arg Pro Gly Ile
            325                 330                 335

Gly Phe Asp Ser Leu Arg Tyr Asp Asp Gln Ile Gly Lys Ile Ser Leu
        340                 345                 350

Val Gly Ala Gly Met Lys Ser Asn Pro Gly Val Thr Ala Asp Phe Phe
355                 360                 365

Thr Ala Leu Ser Asp Ala Gly Val Asn Ile Glu Leu Ile Ser Thr Ser
    370                 375                 380

Glu Ile Arg Ile Ser Val Val Thr Arg Lys Asp Val Asn Glu Ala
385                 390                 395                 400

Val Arg Ala Val His Thr Ala Phe Gly Leu Asp Ser Asp Ser Asp Glu
                405                 410                 415

Ala Val Val Tyr Gly Gly Thr Gly Arg
            420                 425

<210> SEQ ID NO 29
<211> LENGTH: 1192
<212> TYPE: DNA
<213> ORGANISM: Artificial Sequence
<220> FEATURE:
<223> OTHER INFORMATION: synthetic

<400> SEQUENCE: 29

| | | | | | |
|---|---|---|---|---|---|
| atgaaatcta | acaatgcgct | catcgtcatc | ctcggcaccg | tcaccctgga | tgctgtaggc | 60 |
| ataggcttgg | ttatgccggt | actgccgggc | ctcttgcggg | atatcgtcca | ttccgacagc | 120 |
| atcgccagtc | actatggcgt | gctgctagcg | ctatatgcgt | tgatgcaatt | tctatgcgca | 180 |
| cccgttctcg | gagcactgtc | cgaccgcttt | ggccgccgcc | cagtcctgct | cgcttcgcta | 240 |
| cttggagcca | ctatcgacta | cgcgatcatg | gcgaccacac | cgtcctgtg | gatcctctac | 300 |
| gccggacgca | tcgtggccgg | catcaccggc | gccacaggtg | cggttgctgg | cgcctatatc | 360 |
| gccgacatca | ccgatgggga | agatcgggct | cgccacttcg | ggctcatgag | cgcttgtttc | 420 |
| ggcgtgggta | tggtggcagg | ccccgtggcc | ggggactgt | gggcgccat | ctccttgcat | 480 |
| gcaccattcc | ttgcggcggc | ggtgctcaac | ggcctcaacc | tactactggg | ctgcttccta | 540 |
| atgcaggagt | cgcattaagg | gagagcgtcg | accgatgccc | ttgagagcct | tcaacccagt | 600 |
| cagctccttc | cggtgggcgc | ggggcatgac | tatcgtcgcc | gcacttatga | ctgtcttctt | 660 |
| tatcatgcaa | ctcgtaggac | aggtgccggc | agcgctctgg | gtcattttcg | gcaggaccg | 720 |
| cttccgctgg | agcgcgacga | tgatcggcct | gtcgcttgcg | gtattcggaa | tcttgcacgc | 780 |
| cctcgctcaa | gccttcgtca | ctggtcccgc | caccaaacgt | ttcggcgaga | agcaggccat | 840 |
| tatcgccggc | atggcggccg | acgcgctggg | ctacgtcttg | ctggcgttcg | cgacgcgagg | 900 |
| ctggatggcc | ttccccatta | tgattcttct | cgcttccggc | ggcatcggga | tgcccgcgtt | 960 |
| gcaggccatg | ctgtccaggc | aggtagatga | cgaccatcag | ggacagcttc | aaggatcgct | 1020 |
| cgcggctctt | accagcctaa | cttcgatcat | tggaccgctg | atcgtcacgg | cgatttatgc | 1080 |
| cgcctcggcg | agcacatgga | acgggttggc | atggattgta | ggcgccgccc | tataccttgt | 1140 |
| ctgcctcccc | gcgttgcgtc | gcggtgcatg | gagccgggcc | acctcgacct | ga | 1192 |

<210> SEQ ID NO 30
<211> LENGTH: 185
<212> TYPE: PRT
<213> ORGANISM: Artificial Sequence
<220> FEATURE:
<223> OTHER INFORMATION: synthetic

<400> SEQUENCE: 30

Met Lys Ser Asn Asn Ala Leu Ile Val Ile Leu Gly Thr Val Thr Leu
1               5                   10                  15

Asp Ala Val Gly Ile Gly Leu Val Met Pro Val Leu Pro Gly Leu Leu
            20                  25                  30

Arg Asp Ile Val His Ser Asp Ser Ile Ala Ser His Tyr Gly Val Leu
        35                  40                  45

Leu Ala Leu Tyr Ala Leu Met Gln Phe Leu Cys Ala Pro Val Leu Gly
    50                  55                  60

Ala Leu Ser Asp Arg Phe Gly Arg Arg Pro Val Leu Leu Ala Ser Leu
65                  70                  75                  80

Leu Gly Ala Thr Ile Asp Tyr Ala Ile Met Ala Thr Thr Pro Val Leu
                85                  90                  95

Trp Ile Leu Tyr Ala Gly Arg Ile Val Ala Gly Ile Thr Gly Ala Thr
                100                 105                 110

Gly Ala Val Ala Gly Ala Tyr Ile Ala Asp Ile Thr Asp Gly Glu Asp
            115                 120                 125

Arg Ala Arg His Phe Gly Leu Met Ser Ala Cys Phe Gly Val Gly Met
        130                 135                 140

Val Ala Gly Pro Val Ala Gly Gly Leu Leu Gly Ala Ile Ser Leu His
145                 150                 155                 160

Ala Pro Phe Leu Ala Ala Val Leu Asn Gly Leu Asn Leu Leu Leu
                165                 170                 175

Gly Cys Phe Leu Met Gln Glu Ser His
                180                 185

<210> SEQ ID NO 31
<211> LENGTH: 1193
<212> TYPE: DNA
<213> ORGANISM: Artificial Sequence
<220> FEATURE:
<223> OTHER INFORMATION: synthetic

<400> SEQUENCE: 31
atgaaatcta acaatgcgct catcgtcatc ctcggcaccg tcaccctgga tgctgtaggc      60
ataggcttgg ttatgccggt actgccgggc ctcttgcggg atatcgtcca ttccgacagc     120
atcgccagtc actatggcgt gctgctagcg ctatatgcgt tgatgcaatt tctatgcgca     180
cccgttctcg gagcactgtc cgaccgcttt ggccgccgcc cagtcctgct cgcttcgcta     240
cttggagcca ctatcgacta cgcgatcatg gcgaccacac ccgtcctgta aggatcctct     300
acgccggacg catcgtggcc ggcatcaccg gcgccacagg tgcggttgct ggcgcctata     360
tcgccgacat caccgatggg gaagatcggg ctcgccactt cgggctcatg agcgcttgtt     420
tcggcgtggg tatggtggca ggccccgtgg ccgggggact gttgggcgcc atctccttgc     480
atgcaccatt ccttgcggcg gcggtgctca acggcctcaa cctactactg gctgcttcc      540
taatgcagga gtcgcataag ggagagcgtc gaccgatgcc cttgagagcc ttcaacccag     600
tcagctcctt ccggtgggcg cggggcatga ctatcgtcgc cgcacttatg actgtcttct     660
ttatcatgca actcgtagga caggtgccgg cagcgctctg ggtcattttc ggcgaggacc     720
gctttcgctg gagcgcgacg atgatcggcc tgtcgcttgc ggtattcgga atcttgcacg     780
ccctcgctca gccttcgtc actggtcccg ccaccaaacg tttcggcgag aagcaggcca     840
ttatcgccgg catggcggcc gacgcgctgg gctacgtctt gctggcgttc gacgcgag     900
gctggatggc cttccccatt atgattcttc tcgcttccgg cggcatcggg atgcccgcgt     960

-continued

```
tgcaggccat gctgtccagg caggtagatg acgaccatca gggacagctt caaggatcgc    1020
tcgcggctct taccagccta acttcgatca ttggaccgct gatcgtcacg gcgatttatg    1080
ccgcctcggc gagcacatgg aacgggttgg catggattgt aggcgccgcc ctataccttg    1140
tctgcctccc cgcgttgcgt cgcggtgcat ggagccgggc cacctcgacc tga           1193
```

<210> SEQ ID NO 32
<211> LENGTH: 96
<212> TYPE: PRT
<213> ORGANISM: Artificial Sequence
<220> FEATURE:
<223> OTHER INFORMATION: synthetic

<400> SEQUENCE: 32

```
Met Lys Ser Asn Asn Ala Leu Ile Val Ile Leu Gly Thr Val Thr Leu
1               5                   10                  15

Asp Ala Val Gly Ile Gly Leu Val Met Pro Val Leu Pro Gly Leu Leu
            20                  25                  30

Arg Asp Ile Val His Ser Asp Ser Ile Ala Ser His Tyr Gly Val Leu
        35                  40                  45

Leu Ala Leu Tyr Ala Leu Met Gln Phe Leu Cys Ala Pro Val Leu Gly
    50                  55                  60

Ala Leu Ser Asp Arg Phe Gly Arg Arg Pro Val Leu Leu Ala Ser Leu
65                  70                  75                  80

Leu Gly Ala Thr Ile Asp Tyr Ala Ile Met Ala Thr Thr Pro Val Leu
                85                  90                  95
```

<210> SEQ ID NO 33
<211> LENGTH: 565
<212> TYPE: PRT
<213> ORGANISM: Artificial Sequence
<220> FEATURE:
<223> OTHER INFORMATION: synthetic

<400> SEQUENCE: 33

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175
```

```
Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
            195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
            245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
            290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                    325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
            370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                    405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                    485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Asp Phe Lys Arg Ala Phe
545                 550                 555                 560

Asp Leu Asn Leu Arg
            565

<210> SEQ ID NO 34
<211> LENGTH: 2256
```

<212> TYPE: DNA
<213> ORGANISM: Artificial Sequence
<220> FEATURE:
<223> OTHER INFORMATION: synthetic

<400> SEQUENCE: 34

```
atgtacaaag atctgaaatt ccctgttctg attgtacacc gcgatatcaa ggcggacacg      60
gtagccggcg agcgtgttcg cggtattgcc cacgaactcg aacaagacgg ctttagcatt     120
ctctctacgg cgtcttctgc ggaaggccgc attgtggcta gcacgcacca cggtctcgcc     180
tgcatcctcg tggcagctga gggtgcgggt gagaatcagc gtctgctcca agacgtggtt     240
gagctgatcc gtgtagctcg cgtccgtgcg ccacagctcc cgatcttcgc gctgggcgaa     300
caggtgacta ttgaaaacgc gcctgccgaa tgtatggccg acctgcacca gctccgcggc     360
attctgtatc tcttcgagga tactgtcccg ttcctggcac gtcaggttgc acgcgcagcg     420
cgtaactacc tcgctggcct cctcccgcca ttcttccgtg cactcgtgga gcacacggcc     480
caaagcaatt actcttggca caccccgggt cacggtggtg gtgtcgctta ccgtaaatct     540
ccggtaggtc aagctttcca ccagttcttt ggcgagaata ccctccgctc tgacctgtct     600
gttagcgttc cagagctggg cagcctgctg atcacactg gccctctcgc ggaagcagag     660
gatcgtgccg ctcgcaattt cggtgcggac cacaccttct ttgtcatcaa tggtacctct     720
actgcgaaca aaatcgtttg gcactctatg gttggtcgcg aggacctggt gctggtcgat     780
cgtaactgtc acaaatctat tctgcactcc attatcatga cgggtgctat cccactgtac     840
ctgactccgg aacgcaacga actgggtatt atcggcccta ttccactctc cgagttttct     900
aaacaatcta tcgcagcaaa aattgccgcc tccccactcg cgcgtggtcg tgaaccgaaa     960
gttaaactgg ctgtcgttac caactctacc tatgacggtc tgtgttacaa cgcggaactg    1020
atcaaacaaa ccctcggcga ctctgtcgag gtactgcatt tcgacgaggc ttggtatgct    1080
tatgcggcgt tcacgagtt ctacgacggc cgctacggta tgggcacttc tcgttccgaa    1140
gagggtccgc tggtctttgc tacccattct acccacaaga tgctcgcggc ttttttcccaa    1200
gctagcatga ttcacgttca ggatggtggt acgcgcaagc tggacgtcgc ccgctttaac    1260
gaagccttta tgatgcacat cagcacctct ccacagtacg gcatcattgc gtctctcgat    1320
gtcgcaagcg ctatgatgga aggtcctgcc ggtcgtagcc tgatccaaga gacgttcgat    1380
gaggcgctgt ccttccgtcg tgctctggcg aatgtccgtc agaacctgga ccgtaatgat    1440
tggtggttcg gtgtctggca accggagcag gttgagggca ccgaccaggt aggtactcac    1500
gactgggttc tcgagcctag cgcggactgg catggttttg gtgacattgc ggaggattac    1560
gttctcctcg atcctatcaa agttaccctg accaccccag gtctgagcgc tggcggtaaa    1620
ctctctgaac aaggcatccc ggcagctatc gttagccgtt cctgtgggga acgtggtctg    1680
gtggtcgaga aaacgggtct gtactctttc ctggttctgt tctccatggg tatcacgaaa    1740
ggcaaatggt ctactctggt taccgagctg ctcgaattca aacgctgtta cgacgcgaat    1800
ctgccactcc tggatgtgct gccttctgta gcgcaggcgg gtggtaaacg ctataacggt    1860
gtaggtctgc gtgatctgtc cgatgccatg cacgcttctt atcgtgacaa tgccacggcg    1920
aaggccatga agcgtatgta tacggtgctc ccggaagtag ccatgcgccc gtccgaagct    1980
tatgataagc tcgtacgcgg tgaagtcgaa gctgttccta ttgcacgtct cgagggtcgt    2040
attcggcgg ttatgctggt tccgtacccg ccaggtatcc cgctcattat gccgggtgaa    2100
cgttttactg aagctacccg ctccattctg gactatctgg agtttgcccg taccttcgag    2160
```

```
cgcgcgttcc cgggctttga ctctgatgtt cacggcctcc aacatcaaga tggcccgtct    2220
ggccgttgtt ataccgttga atgcatcaag gaataa                              2256

<210> SEQ ID NO 35
<211> LENGTH: 2256
<212> TYPE: DNA
<213> ORGANISM: Artificial Sequence
<220> FEATURE:
<223> OTHER INFORMATION: synthetic

<400> SEQUENCE: 35
atgtacaaag atctgaaatt ccctgttctg attgtacacc gcgatatcaa ggcggacacg      60
gtagccggcg agcgtgttcg cggtattgcc cacgaactcg aacaagacgg ctttagcatt     120
ctctctacgg cgtcttctgc ggaaggccgc attgtggcta gcacgcacca cggtctcgcc     180
tgcatcctcg tggcagctga gggtgcgggt gagaatcagc gtctgctcca agacgtggtt     240
gagctgatcc gtgtagctcg cgtccgtgcg ccacagctcc cgatcttcgc gctgggcgaa     300
caggtgacta ttgaaaacgc gcctgccgaa tctatggccg acctgcacca gctccgcggc     360
attctgtatc tcttcgagga tactgtcccg ttcctggcac gtcaggttgc acgcgcagcg     420
cgtaactacc tcgctggcct cctcccgcca ttcttccgtg cactcgtgga gcacacggcc     480
caaagcaatt actcttggca caccccgggt cacggtggtg gtgtcgctta ccgtaaatct     540
ccggtaggtc aagcttttcca ccagttcttt ggcgagaata ccctccgctc tgacctgtct     600
gttagcgttc agagctggg cagcctgctg gatcacactg ccctctcgc ggaagcagag      660 gatcgtgccg ctcgcaattt cggtgcggac cacaccttct ttgtcatcaa tggtacctct     720
actgcgaaca aaatcgtttg gcactctatg gttggtcgcg aggacctggt gctggtcgat     780
cgtacctgtc acaaatctat tctgcactcc attatcatga cgggtgctat cccactgtac     840
ctgactccgg aacgcaacga actgggtatt atcggcccta ttccactctc gagttttct      900 aaacaatcta tcgcagcaaa aattgccgcc tccccactcg cgcgtggtcg tgaaccgaaa     960
gttaaactgg ctgtcgttac caactctacc tatgacggtc tgtgttacaa cgcggaactg    1020
atcaaacaaa ccctcggcga ctctgtcgag gtactgcatt tcgacgaggc ttggtatgct    1080
tatgcggcgt tcacgagtt ctacgacggc cgctacggta tgggcacttc tcgttccgaa    1140
gagggtccgc tggtctttgc tacccattct acccacaaga tgctcgcggc ttttcccaa     1200 gctagcatga ttcacgttca ggatggtggt acgcgcaagc tggacgtcgc ccgctttaac    1260
gaagccttta tgatgcacat cagcacctct ccacagtacg gcatcattgc gtctctcgat    1320
gtcgcaagcg ctatgatgga aggtcctgcc ggtcgtagcc tgatccaaga gacgttcgat    1380
gaggcgctgt ccttccgtcg tgctctggcg aatgtccgtc agaacctgga ccgtaatgat    1440
tggtggttcg gtgtctggca accggagcag gttgagggca ccgaccaggt aggtactcac    1500
gactgggttc tcgagcctag cgcggactgg catggttttg gtgacattgc ggaggattac    1560
gttctcctcg atcctatcaa gttaccctg accaccccag gtctgagcgc tggcggtaaa    1620
ctctctgaac aaggcatccc ggcagctatc gttagccgtt cctgtggga acgtggtctg    1680 gtggtcgaga aaacgggtct gtactcttc ctggttctgt tctccatggg tatcacgaaa    1740
ggcaaatggt ctactctggt taccgagctg ctcgaattca aacgctgtta cgacgcgaat    1800
ctgccactcc tggatgtgct gccttctgta gcgcaggcgg tggtaaacg ctataacggt    1860 gtaggtctgc gtgatctgtc cgatgccatg cacgcttctt atcgtgacaa tgccacggcg    1920
aaggccatga agcgtatgta tacggtgctc ccggaagtag ccatgcgccc gtccgaagct    1980
```

```
tatgataagc tcgtacgcgg tgaagtcgaa gctgttccta ttgcacgtct cgagggtcgt    2040
attgcggcgg ttatgctggt tccgtacccg ccaggtatcc cgctcattat gccgggtgaa    2100
cgttttactg aagctacccg ctccattctg gactatctgg agtttgcccg taccttcgag    2160
cgcgcgttcc cgggctttga ctctgatgtt cacggcctcc aacatcaaga tggcccgtct    2220
ggccgttgtt ataccgttga atgcatcaag gaataa                              2256
```

<210> SEQ ID NO 36
<211> LENGTH: 2256
<212> TYPE: DNA
<213> ORGANISM: Artificial Sequence
<220> FEATURE:
<223> OTHER INFORMATION: synthetic

<400> SEQUENCE: 36

```
atgtacaaag atctgaaatt ccctgttctg attgtacacc gcgatatcaa ggcggacacg      60
gtagccggcg agcgtgttcg cggtattgcc cacgaactcg aacaagacgg ctttagcatt     120
ctctctacgg cgtcttctgc ggaaggccgc attgtggcta gcacgcacca cggtctcgcc     180
tgcatcctcg tggcagctga gggtgcgggt gagaatcagc gtctgctcca agacgtggtt     240
gagctgatcc gtgtagctcg cgtccgtgcg ccacagctcc cgatcttcgc gctgggcgaa     300
caggtgacta ttgaaaacgc gcctgccgaa tctatggccg acctgcacca gctccgcggc     360
attctgtatc tcttcgagga tactgtcccg ttcctggcac gtcaggttgc acgcgcagcg     420
cgtaactacc tcgctggcct cctcccgcca ttcttccgtg cactcgtgga gcacacggcc     480
caaagcaatt actcttggca caccccgggt cacggtggtg gtgtcgctta ccgtaaatct     540
ccggtaggtc aagcttttcca ccagttcttt ggcgagaata ccctccgctc tgacctgtct     600
gttagcgttc cagagctggg cagcctgctg gatcacactg gccctctcgc ggaagcagag     660
gatcgtgccg ctcgcaattt cggtgcggac cacaccttct ttgtcatcaa tggtacctct     720
actgcgaaca aaatcgtttg gcactctatg gttggtcgcg aggacctggt gctggtcgat     780
cgtaactgtc acaactctat tctgcactcc attatcatga cgggtgctat cccactgtac     840
ctgactccgg aacgcaacga actgggtatt atcggcccta ttccactctc cgagttttct     900
aaacaatcta tcgcagcaaa aattgccgcc tccccactcg cgcgtggtcg tgaaccgaaa     960
gttaaactgg ctgtcgttac caactctacc tatgacggtc tgtgttacaa cgcggaactg    1020
atcaaacaaa ccctcggcga ctctgtcgag gtactgcatt tcgacgaggc ttggtatgct    1080
tatgcggcgt ttcacgagtt ctacgacggc cgctacggta tgggcacttc tcgttccgaa    1140
gagggtccgc tggtctttgc tacccattct acccacaaga tgctcgcggc ttttccccaa    1200
gctagcatga ttcacgttca ggatggtggt acgcgcaagc tggacgtcgc ccgctttaac    1260
gaagccttta tgatgcacat cagcacctct ccacagtacg gcatcattgc gtctctcgat    1320
gtcgcaagcg ctatgatgga aggtcctgcc ggtcgtagcc tgatccaaga gacgttcgat    1380
gaggcgctgt ccttccgtcg tgctctggcg aatgtccgtc agaacctgga ccgtaatgat    1440
tggtggttcg gtgtctggca accggagcag gttgagggca ccgaccaggt aggtactcac    1500
gactgggttc tcgagcctag cgcggactgg catggttttg gtgacattgc ggaggattac    1560
gttctcctcg atcctatcaa agttaccctg accaccccag gtctgagcgc tggcggtaaa    1620
ctctctgaac aaggcatccc ggcagctatc gttagccgtt tcctgtggga acgtggtctg    1680
gtggtcgaga aaacgggtct gtactctttc ctggttctgt tctccatggg tatcacgaaa    1740
```

| | |
|---|---|
| ggcaaatggt ctactctggt taccgagctg ctcgaattca aacgctgtta cgacgcgaat | 1800 |
| ctgccactcc tggatgtgct gccttctgta gcgcaggcgg gtggtaaacg ctataacggt | 1860 |
| gtaggtctgc gtgatctgtc cgatgccatg cacgcttctt atcgtgacaa tgccacggcg | 1920 |
| aaggccatga agcgtatgta tacggtgctc ccggaagtag ccatgcgccc gtccgaagct | 1980 |
| tatgataagc tcgtacgcgg tgaagtcgaa gctgttccta ttgcacgtct cgagggtcgt | 2040 |
| attgcggcgg ttatgctggt tccgtacccg ccaggtatcc cgctcattat gccgggtgaa | 2100 |
| cgttttactg aagctacccg ctccattctg gactatctgg agtttgcccg taccttcgag | 2160 |
| cgcgcgttcc cgggctttga ctctgatgtt cacggcctcc aacatcaaga tggcccgtct | 2220 |
| ggccgttgtt ataccgttga atgcatcaag gaataa | 2256 |

<210> SEQ ID NO 37
<211> LENGTH: 2256
<212> TYPE: DNA
<213> ORGANISM: Artificial Sequence
<220> FEATURE:
<223> OTHER INFORMATION: synthetic

<400> SEQUENCE: 37

| | |
|---|---|
| atgtacaaag atctgaaatt ccctgttctg attgtacacc gcgatatcaa ggcggacacg | 60 |
| gtagccggcg agcgtgttcg cggtattgcc cacgaactcg aacaagacgg ctttagcatt | 120 |
| ctctctacgg cgtcttctgc ggaaggccgc attgtggcta gcacgcacca cggtctcgcc | 180 |
| tgcatcctcg tggcagctga gggtgcgggt gagaatcagc gtctgctcca agacgtggtt | 240 |
| gagctgatcc gtgtagctcg cgtccgtgcg ccacagctcc cgatcttcgc gctgggcgaa | 300 |
| caggtgacta ttgaaaacgc gcctgccgaa tgtatggccg acctgcacca gctccgcggc | 360 |
| attctgtatc tcttcgagga tactgtcccg ttcctggcac gtcaggttgc acgcgcagcg | 420 |
| cgtaactacc tcgctggcct cctcccgcca ttcttccgtg cactcgtgga gcacacggcc | 480 |
| caaagcaatt actcttggca caccccgggt cacggtggtg gtgtcgctta ccgtaaatct | 540 |
| ccggtaggtc aagcttttcca ccagttcttt ggcgagaata ccctccgctc tgacctgtct | 600 |
| gttagcgttc cagagctggg cagcctgctg atcacactg gccctctcgc ggaagcagag | 660 |
| gatcgtgccg ctcgcaattt cggtgcggac cacaccttct tgtcatcaa tggtacctct | 720 |
| actgcgaaca aaatcgtttg gcactctatg gttggtcgcg aggacctggt gctggtcgat | 780 |
| cgtacctgtc acaaatctat tctgcactcc attatcatga cgggtgctat cccactgtac | 840 |
| ctgactccgg aacgcaacga actgggtatt atcggcccta ttccactctc cgagttttct | 900 |
| aaacaatcta tcgcagcaaa aattgccgcc tccccactcg cgcgtggtcg tgaaccgaaa | 960 |
| gttaaactgg ctgtcgttac caactctacc tatgacggtc tgtgttacaa cgcggaactg | 1020 |
| atcaaacaaa ccctcggcga ctctgtcgag gtactgcatt tcgacgaggc ttggtatgct | 1080 |
| tatgcggcgt ttcacgagtt ctacgacggc cgctacggta tgggcacttc tcgttccgaa | 1140 |
| gagggtccgc tggtctttgc tacccattct acccacaaga tgctcgcggc ttttttccaa | 1200 |
| gctagcatga ttcacgttca ggatggtggt acgcgcaagc tggacgtcgc ccgctttaac | 1260 |
| gaagccttta tgatgcacat cagccacctct ccacagtacg gcatcattgc gtctctcgat | 1320 |
| gtcgcaagcg ctatgatgga aggtcctgcc ggtcgtagcc tgatccaaga gacgttcgat | 1380 |
| gaggcgctgt ccttccgtcg tgctctggcg aatgtccgtc agaacctgga ccgtaatgat | 1440 |
| tggtggttcg gtgtctggca accggagcag gttgagggca ccgaccaggt aggtactcac | 1500 |
| gactgggttc tcgagcctag cgcggactgg catggttttg gtgacattgc ggaggattac | 1560 |

```
gttctcctcg atcctatcaa agttaccctg accaccccag gtctgagcgc tggcggtaaa      1620
ctctctgaac aaggcatccc ggcagctatc gttagccgtt tcctgtggga acgtggtctg      1680
gtggtcgaga aaacgggtct gtactctttc ctggttctgt tctccatggg tatcacgaaa      1740
ggcaaatggt ctactctggt taccgagctg ctcgaattca aacgctgtta cgacgcgaat      1800
ctgccactcc tggatgtgct gccttctgta gcgcaggcgg gtggtaaacg ctataacggt      1860
gtaggtctgc gtgatctgtc cgatgccatg cacgcttctt atcgtgacaa tgccacggcg      1920
aaggccatga agcgtatgta tacggtgctc ccggaagtag ccatgcgccc gtccgaagct      1980
tatgataagc tcgtacgcgg tgaagtcgaa gctgttccta ttgcacgtct cgagggtcgt      2040
attgcggcgg ttatgctggt tccgtacccg ccaggtatcc cgctcattat gccgggtgaa      2100
cgttttactg aagctacccg ctccattctg gactatctgg agtttgcccg taccttcgag      2160
cgcgcgttcc cgggctttga ctctgatgtt cacggcctcc aacatcaaga tggcccgtct      2220
ggccgttgtt ataccgttga atgcatcaag gaataa                               2256

<210> SEQ ID NO 38
<211> LENGTH: 2256
<212> TYPE: DNA
<213> ORGANISM: Artificial Sequence
<220> FEATURE:
<223> OTHER INFORMATION: synthetic

<400> SEQUENCE: 38
atgtacaaag atctgaaatt ccctgttctg attgtacacc gcgatatcaa ggcggacacg        60
gtagccggcg agcgtgttcg cggtattgcc cacgaactcg aacaagacgg ctttagcatt       120
ctctctacgg cgtcttctgc ggaaggccgc attgtggcta gcacgcacca cggtctcgcc       180
tgcatcctcg tggcagctga gggtgcgggt gagaatcagc gtctgctcca agacgtggtt       240
gagctgatcc gtgtagctcg cgtccgtgcg ccacagctcc cgatcttcgc gctgggcgaa       300
caggtgacta ttgaaaacgc gcctgccgaa tgtatggccg acctgcacca gctccgcggc       360
attctgtatc tcttcgagga tactgtcccg ttcctggcac gtcaggttgc acgcgcagcg       420
cgtaactacc tcgctggcct cctcccgcca ttcttccgtg cactcgtgga gcacacggcc       480
caaagcaatt actcttggca caccccgggt cacggtggtg gtgtcgctta ccgtaaatct       540
ccggtaggtc aagcttttcca ccagttcttt ggcgagaata ccctccgctc tgacctgtct       600
gttagcgttc cagagctggg cagcctgctg gatcacactg gccctctcgc ggaagcagag       660
gatcgtgccg ctcgcaattt cggtgcggac cacaccttct tgtcatcaa tggtacctct       720 actgcgaaca aaatcgtttg gcactctatg gttggtcgcg aggacctggt gctggtcgat       780
cgtaactgtc acaactctat tctgcactcc attatcatga cgggtgctat cccactgtac       840
ctgactccgg aacgcaacga actgggtatt atcggcccta ttccactctc cgagttttct       900
aaacaatcta tcgcagcaaa aattgccgcc tccccactcg cgcgtggtcg tgaaccgaaa       960
gttaaactgg ctgtcgttac caactctacc tatgacggtc tgtgttacaa cgcggaactg      1020
atcaaacaaa ccctcggcga ctctgtcgag gtactgcatt tcgacgaggc ttggtatgct      1080
tatgcggcgt tcacgagtt ctacgacggc cgctacggta tgggcacttc tcgttccgaa       1140
gagggtccgc tggtctttgc tacccattct acccacaaga tgctcgcggc tttttcccaa      1200
gctagcatga ttcacgttca ggatggtggt acgcgcaagc tggacgtcgc ccgctttaac      1260
gaagccttta tgatgcacat cagcacctct ccacagtacg gcatcattgc gtctctcgat      1320
```

```
gtcgcaagcg ctatgatgga aggtcctgcc ggtcgtagcc tgatccaaga gacgttcgat    1380
gaggcgctgt ccttccgtcg tgctctggcg aatgtccgtc agaacctgga ccgtaatgat    1440
tggtggttcg gtgtctggca accggagcag gttgagggca ccgaccaggt aggtactcac    1500
gactgggttc tcgagcctag cgcggactgg catggttttg gtgacattgc ggaggattac    1560
gttctcctcg atcctatcaa agttaccctg accaccccag gtctgagcgc tggcggtaaa    1620
ctctctgaac aaggcatccc ggcagctatc gttagccgtt cctgtgggaa cgtggtctg     1680 gtggtcgaga aaacgggtct gtactctttc ctggttctgt tctccatggg tatcacgaaa    1740
ggcaaatggt ctactctggt taccgagctg ctcgaattca aacgctgtta cgacgcgaat    1800
ctgccactcc tggatgtgct gccttctgta gcgcaggcgg gtggtaaacg ctataacggt    1860
gtaggtctgc gtgatctgtc cgatgccatg cacgcttctt atcgtgacaa tgccacggcg    1920
aaggccatga agcgtatgta tacggtgctc ccggaagtag ccatgcgccc gtccgaagct    1980
tatgataagc tcgtacgcgg tgaagtcgaa gctgttccta ttgcacgtct cgagggtcgt    2040
attgcggcgg ttatgctggt tccgtacccg ccaggtatcc cgctcattat gccgggtgaa    2100
cgttttactg aagctacccg ctccattctg gactatctgg agtttgcccg taccttcgag    2160
cgcgcgttcc cgggctttga ctctgatgtt cacggcctcc aacatcaaga tggcccgtct    2220
ggccgttgtt ataccgttga atgcatcaag gaataa                              2256
```

<210> SEQ ID NO 39
<211> LENGTH: 2256
<212> TYPE: DNA
<213> ORGANISM: Artificial Sequence
<220> FEATURE:
<223> OTHER INFORMATION: synthetic

<400> SEQUENCE: 39

```
atgtacaaag atctgaaatt ccctgttctg attgtacacc gcgatatcaa ggcggacacg      60
gtagccggcg agcgtgttcg cggtattgcc cacgaactcg aacaagacgg ctttagcatt    120
ctctctacgg cgtcttctgc ggaaggccgc attgtggcta gcacgcacca cggtctcgcc    180
tgcatcctcg tggcagctga gggtgcgggt gagaatcagc gtctgctcca agacgtggtt    240
gagctgatcc gtgtagctcg cgtccgtgcg ccacagctcc cgatcttcgc gctgggcgaa    300
caggtgacta ttgaaaacgc gcctgccgaa tctatggccg acctgcacca gctccgcggc    360
attctgtatc tcttcgagga tactgtcccg ttcctggcac gtcaggttgc acgcgcagcg    420
cgtaactacc tcgctggcct cctcccgcca ttcttccgtg cactcgtgga gcacacggcc    480
caaagcaatt actcttggca caccccgggt cacggtggtg gtgtcgctta ccgtaaatct    540
ccggtaggtc aagctttcca ccagttctttt ggcgagaata ccctccgctc tgacctgtct    600
gttagcgttc cagagctggg cagcctgctg gatcacactg gccctctcgc ggaagcagag    660
gatcgtgccg ctcgcaattt cggtgcggac cacaccttct tgtcatcaa tggtacctct    720 actgcgaaca aaatcgtttg gcactctatg gttggtcgcg aggacctggt gctggtcgat    780
cgtacctgtc acaactctat tctgcactcc attatcatga cgggtgctat cccactgtac    840
ctgactccgg aacgcaacga actgggtatt atcggccta ttccactctc cgagttttct    900
aaacaatcta tcgcagcaaa aattgccgcc tcccactcg cgcgtggtcg tgaaccgaaa    960
gttaaactgg ctgtcgttac caactctacc tatgacggtc tgtgttacaa cgcggaactg    1020
atcaaacaaa ccctcggcga ctctgtcgag gtactgcatt tcgacgaggc ttggtatgct    1080
tatgcggcgt ttcacgagtt ctacgacggc cgctacggta tgggcacttc tcgttccgaa    1140
```

```
gagggtccgc tggtctttgc tacccattct acccacaaga tgctcgcggc ttttttcccaa    1200 gctagcatga ttcacgttca ggatggtggt acgcgcaagc tggacgtcgc ccgctttaac    1260
gaagccttta tgatgcacat cagcacctct ccacagtacg gcatcattgc gtctctcgat    1320
gtcgcaagcg ctatgatgga aggtcctgcc ggtcgtagcc tgatccaaga cgcgttcgat    1380
gaggcgctgt ccttccgtcg tgctctggcg aatgtccgtc agaacctgga ccgtaatgat    1440
tggtggttcg gtgtctggca accggagcag gttgagggca ccgaccaggt aggtactcac    1500
gactgggttc tcgagcctag cgcggactgg catggttttg gtgacattgc ggaggattac    1560
gttctcctcg atcctatcaa agttaccctg accaccccag gtctgagcgc tggcggtaaa    1620
ctctctgaac aaggcatccc ggcagctatc gttagccgtt tcctgtggga acgtggtctg    1680
gtggtcgaga aaacgggtct gtactctttc ctggttctgt tctccatggg tatcacgaaa    1740
ggcaaatggt ctactctggt taccgagctg ctcgaattca aacgctgtta cgacgcgaat    1800
ctgccactcc tggatgtgct gccttctgta gcgcaggcgg tggtaaacg ctataacggt    1860 gtaggtctgc gtgatctgtc cgatgccatg cacgcttctt atcgtgacaa tgccacggcg    1920
aaggccatga agcgtatgta tacggtgctc ccggaagtag ccatgcgccc gtccgaagct    1980
tatgataagc tcgtacgcgg tgaagtcgaa gctgttccta ttgcacgtct cgagggtcgt    2040
attgcggcgg ttatgctggt tccgtacccg ccaggtatcc cgctcattat gccgggtgaa    2100
cgttttactg aagctacccg ctccattctg gactatctgg agtttgcccg taccttcgag    2160
cgcgcgttcc cgggctttga ctctgatgtt cacggcctcc aacatcaaga tggcccgtct    2220
ggccgttgtt ataccgttga atgcatcaag gaataa                             2256
```

<210> SEQ ID NO 40
<211> LENGTH: 2256
<212> TYPE: DNA
<213> ORGANISM: Artificial Sequence
<220> FEATURE:
<223> OTHER INFORMATION: synthetic

<400> SEQUENCE: 40

```
atgtacaaag atctgaaatt ccctgttctg attgtacacc gcgatatcaa ggcggacacg     60
gtagccggcg agcgtgttcg cggtattgcc cacgaactcg aacaagacgg ctttagcatt    120
ctctctacgg cgtcttctgc ggaaggccgc attgtggcta gcacgcacca cggtctcgcc    180
tgcatcctcg tggcagctga gggtgcgggt gagaatcagc gtctgctcca agacgtggtt    240
gagctgatcc gtgtagctcg cgtccgtgcg ccacagctcc cgatcttcgc gctgggcgaa    300
caggtgacta ttgaaaacgc gcctgccgaa tgtatggccg acctgcacca gctccgcggc    360
attctgtatc tcttcgagga tactgtcccg ttcctggcac gtcaggttgc acgcgcagcg    420
cgtaactacc tcgctggcct cctcccgcca ttcttccgtg cactcgtgga gcacacggcc    480
caaagcaatt actcttggca caccccgggt acggtggtg gtgtcgctta ccgtaaatct    540
ccggtaggtc aagctttcca ccagttcttt ggcgagaata ccctccgctc tgacctgtct    600
gttagcgttc cagagctggg cagcctgctg gatcacactg gcctctcgc ggaagcagag    660 gatcgtgccc ctcgcaattt cggtgcggac cacaccttct ttgtcatcaa tggtacctct    720
actgcgaaca aaatcgtttg gcactctatg gttggtcgcg aggacctggt gctggtcgat    780
cgtacctgtc acaactctat tctgcactcc attatcatga cgggtgctat cccactgtac    840
ctgactccgg aacgcaacga actgggtatt atcggcccta ttccactctc cgagttttct    900
```

| | |
|---|---|
| aaacaatcta tcgcagcaaa aattgccgcc tccccactcg cgcgtggtcg tgaaccgaaa | 960 |
| gttaaactgg ctgtcgttac caactctacc tatgacggtc tgtgttacaa cgcggaactg | 1020 |
| atcaaacaaa ccctcggcga ctctgtcgag gtactgcatt tcgacgaggc ttggtatgct | 1080 |
| tatgcggcgt ttcacgagtt ctacgacggc cgctacggta tgggcacttc tcgttccgaa | 1140 |
| gagggtccgc tggtctttgc tacccattct acccacaaga tgctcgcggc ttttttccaa | 1200 |
| gctagcatga ttcacgttca ggatggtggt acgcgcaagc tggacgtcgc ccgctttaac | 1260 |
| gaagccttta tgatgcacat cagcacctct ccacagtacg gcatcattgc gtctctcgat | 1320 |
| gtcgcaagcg ctatgatgga aggtcctgcc ggtcgtagcc tgatccaaga acgttcgat | 1380 |
| gaggcgctgt ccttccgtcg tgctctggcg aatgtccgtc agaacctgga ccgtaatgat | 1440 |
| tggtggttcg gtgtctggca accggagcag gttgagggca ccgaccaggt aggtactcac | 1500 |
| gactgggttc tcgagcctag cgcggactgg catggttttg gtgacattgc ggaggattac | 1560 |
| gttctcctcg atcctatcaa agttaccctg accaccccag gtctgagcgc tggcggtaaa | 1620 |
| ctctctgaac aaggcatccc ggcagctatc gttagccgtt cctgtgggga acgtggtctg | 1680 |
| gtggtcgaga aaacgggtct gtactctttc ctggttctgt tctccatggg tatcacgaaa | 1740 |
| ggcaaatggt ctactctggt taccgagctg ctcgaattca aacgctgtta cgacgcgaat | 1800 |
| ctgccactcc tggatgtgct gccttctgta gcgcaggcgg tggtaaacg ctataacggt | 1860 |
| gtaggtctgc gtgatctgtc cgatgccatg cacgcttctt atcgtgacaa tgccacggcg | 1920 |
| aaggccatga agcgtatgta tacggtgctc ccggaagtag ccatgcgccc gtccgaagct | 1980 |
| tatgataagc tcgtacgcgg tgaagtcgaa gctgttccta ttgcacgtct cgagggtcgt | 2040 |
| attgcggcgg ttatgctggt tccgtacccg ccaggtatcc cgctcattat gccgggtgaa | 2100 |
| cgttttactg aagctacccg ctccattctg gactatctgg agtttgcccg taccttcgag | 2160 |
| cgcgcgttcc cgggctttga ctctgatgtt cacggcctcc aacatcaaga tggcccgtct | 2220 |
| ggccgttgtt ataccgttga atgcatcaag gaataa | 2256 |

<210> SEQ ID NO 41
<211> LENGTH: 2148
<212> TYPE: DNA
<213> ORGANISM: Escherichia coli

<400> SEQUENCE: 41

| | |
|---|---|
| atgaacgtta ttgcaatatt gaatcacatg ggggtttatt ttaaagaaga acccatccgt | 60 |
| gaacttcatc gcgcgcttga acgtctgaac ttccagattg tttacccgaa cgaccgtgac | 120 |
| gacttattaa aactgatcga aaacaatgcg cgtctgtgcg gcgttatttt tgactgggat | 180 |
| aaatataatc tcgagctgtg cgaagaaatt agcaaaatga acgagaacct gccgttgtac | 240 |
| gcgttcgcta atacgtattc cactctcgat gtaagcctga atgacctgcg tttacagatt | 300 |
| agcttctttg aatatgcgct gggtgctgct gaagatattg ctaataagat caagcagacc | 360 |
| actgacgaat atatcaacac tattctgcct ccgctgacta agcactgtt taaatatgtt | 420 |
| cgtgaaggta aatatacttt ctgtactcct ggtcacatgg gcggtactgc attccagaaa | 480 |
| agcccggtag gtagcctgtt ctatgatttc tttggtccga ataccatgaa atctgatatt | 540 |
| tccatttcag tatctgaact gggttctctg ctggatcaca gtggtccaca caaagaagca | 600 |
| gaacagtata tcgctcgcgt ctttaacgca gaccgcagct acatggtgac caacggtact | 660 |
| tccactgcga acaaaattgt tggtatgtac tctgctccag caggcagcac cattctgatt | 720 |
| gaccgtaact gccacaaatc gctgacccac ctgatgatga tgagcgatgt tacgccaatc | 780 |

-continued

```
tatttccgcc cgacccgtaa cgcttacggt attcttggtg gtatcccaca gagtgaattc    840
cagcacgcta ccattgctaa gcgcgtgaaa gaaacaccaa acgcaacctg ccggtacat     900
gctgtaatta ccaactctac ctatgatggt ctgctgtaca acaccgactt catcaagaaa    960
acactggatg tgaaatccat ccactttgac tccgcgtggg tgccttacac caacttctca    1020
ccgatttacg aaggtaaatg cggtatgagc ggtggccgtg tagaagggaa agtgatttac    1080
gaaacccagt ccactcacaa actgctggcg gcgttctctc aggcttccat gatccacgtt    1140
aaaggtgacg taaacgaaga aaccttaaac gaagcctaca tgatgcacac caccacttct    1200
ccgcactacg gtatcgtggc gtccactgaa accgctgcgg cgatgatgaa aggcaatgca    1260
ggtaagcgtc tgatcaacgg ttctattgaa cgtgcgatca aattccgtaa agagatcaaa    1320
cgtctgagaa cggaatctga tggctggttc tttgatgtat ggcagccgga tcatatcgat    1380
acgactgaat gctggccgct gcgttctgac agcacctggc acggcttcaa aaacatcgat    1440
aacgagcaca tgtatcttga cccgatcaaa gtcaccctgc tgactccggg gatggaaaaa    1500
gacggcacca tgagcgactt tggtattccg gccagcatcg tggcgaaata cctcgacgaa    1560
catggcatcg ttgttgagaa aaccggtccg tataacctgc tgttcctgtt cagcatcggt    1620
atcgataaga ccaaagcact gagcctgctg cgtgctctga ctgactttaa acgtgcgttc    1680
gacctgaacc tgcgtgtgaa aaacatgctg ccgtctctgt atcgtgaaga tcctgaattc    1740
tatgaaaaca tgcgtattca ggaactggct cagaatatcc acaaactgat tgttcaccac    1800
aatctgccgg atctgatgta tcgcgcattt gaagtgctgc cgacgatggt aatgactccg    1860
tatgctgcat tccagaaaga gctgcacggt atgaccgaag aagtttacct cgacgaaatg    1920
gtaggtcgta ttaacgccaa tatgatcctt ccgtacccgc cgggagttcc tctggtaatg    1980
ccgggtgaaa tgatcaccga agaaagccgt ccggttctgg agttcctgca gatgctgtgt    2040
gaaatcggcg ctcactatcc gggctttgaa accgatattc acggtgcata ccgtcaggct    2100
gatggccgct ataccgttaa ggtattgaaa gaagaaagca aaaaataa                 2148
```

<210> SEQ ID NO 42
<211> LENGTH: 2142
<212> TYPE: DNA
<213> ORGANISM: Escherichia coli

<400> SEQUENCE: 42

```
atgaacatca ttgccattat gggaccgcat ggcgtctttt ataaagatga gcccatcaaa    60
gaactggagt cggcgctggt ggcgcaaggc tttcagatta tctggccaca aaacagcgtt    120
gatttgctga aatttatcga gcataaccct cgaatttgcg gcgtgatttt tgactgggat    180
agtacagtc tcgattatgt agcgatatc aatcagctta tgaatatct cccgcttat     240
gccttcatca cacccactc gacgatggat gtcagcgtgc aggatatgcg gatggcgctc    300
tggttttttg aatatgcgct ggggcaggcg gaagatatcg ccattcgtat gcgtcagtac    360
accgacgaat atcttgataa cattacaccg ccgttcacga aagccttgtt tacctacgtc    420
aaagagcgga agtacacctt ttgtacgccg gggcatatgg gcggcaccgc atatcaaaaa    480
agcccggttg gctgtctgtt ttatgatttt ttcggcggga atactcttaa ggctgatgtc    540
tctatttcgg tcaccgagct tggttcgttg ctcgaccaca ccgggccaca cctggaagcg    600
gaagagtaca tcgcgcggac ttttggcgcg aacagagtt atatcgttac caacggaaca    660
tcgacgtcga acaaaattgt gggtatgtac gccgcgccat ccggcagtac gctgttgatc    720
```

```
gaccgcaatt gtcataaatc gctggcgcat ctgttgatga tgaacgatgt agtgccagtc    780
tggctgaaac cgacgcgtaa tgcgttgggg attcttggtg ggatcccgcg ccgtgaattt    840
actcgcgaca gcatcgaaga gaaagtcgct gctaccacgc aagcacaatg gccggttcat    900
gcggtgatca ccaactccac ctatgatggc ttgctctaca acaccgactg gatcaaacag    960
acgctggatg tcccgtcgat tcacttcgat tctgcctggg tgccgtacac ccattttcat   1020
ccgatctacc agggtaaaag tggtatgagc ggcgagcgtg ttgcgggaaa agtgatcttc   1080
gaaacgcaat cgacccacaa aatgctggcg gcgttatcgc aggcttcgct gatccacatt   1140
aaaggcgagt atgacgaaga ggcctttaac gaagcccttta tgatgcatac caccacctcg   1200
cccagttatc ccattgttgc ttcggttgag acggcggcgg cgatgctgcg tggtaatccg   1260
ggcaaacggc tgattaaccg ttcagtagaa cgagctctgc attttcgcaa agaggtccag   1320
cggctgcggg aagagtctga cggttggttt ttcgatatct ggcaaccgcc gcaggtggat   1380
gaagccgaat gctggcccgt tgcgcctggc gaacagtggc acggctttaa cgatgcggat   1440
gccgatcata tgtttctcga tccggttaaa gtcactattt tgacaccggg gatggacgag   1500
cagggcaata tgagcgagga ggggatcccg gcggcgctgg tagcaaaaatt cctcgacgaa   1560 cgtgggatcg tagtagagaa aaccggcccct tataacctgc tgtttctctt tagtattggc   1620
atcgataaaa ccaaagcaat gggattattg cgtgggttga cggaattcaa acgctcttac   1680
gatctcaacc tgcggatcaa aaatatgcta cccgatctct atgcagaaga tcccgatttc   1740
taccgcaata tgcgtattca ggatctggca aagggatcc ataagctgat tcgtaaacac   1800
gatcttcccg gtttgatgtt gcgggcattc gatactttgc cggagatgat catgacgcca   1860
catcaggcat ggcaacgaca aattaaaggc gaagtagaaa ccattgcgct ggaacaactg   1920
gtcggtagag tatcggcaaa tatgatcctg ccttatccac cgggcgtacc gctgttgatg   1980
cctggagaaa tgctgaccaa agagagccgc acagtactcg attttctact gatgctttgt   2040
tccgtcgggc aacattaccc cggttttgaa acgatattc acggcgcgaa acaggacgaa   2100
gacggcgttt accgcgtacg agtcctaaaa atggcgggat aa                      2142
```

<210> SEQ ID NO 43
<211> LENGTH: 49
<212> TYPE: DNA
<213> ORGANISM: Artificial Sequence
<220> FEATURE:
<223> OTHER INFORMATION: primer

<400> SEQUENCE: 43

```
ggcgagctca cacaggaaac agaccatgaa atctaacaat gcgctcatc                 49
```

<210> SEQ ID NO 44
<211> LENGTH: 29
<212> TYPE: DNA
<213> ORGANISM: Artificial Sequence
<220> FEATURE:
<223> OTHER INFORMATION: primer

<400> SEQUENCE: 44

```
ggctctagat caacgacagg agcacgatc                                      29
```

<210> SEQ ID NO 45
<211> LENGTH: 29
<212> TYPE: DNA
<213> ORGANISM: Artificial Sequence
<220> FEATURE:
<223> OTHER INFORMATION: primer

```
<400> SEQUENCE: 45
ggctctagaa cacaggaaac agaccatga                                29

<210> SEQ ID NO 46
<211> LENGTH: 29
<212> TYPE: DNA
<213> ORGANISM: Artificial Sequence
<220> FEATURE:
<223> OTHER INFORMATION: primer

<400> SEQUENCE: 46
ggcaagcttt caacgacagg agcacgatc                                29

<210> SEQ ID NO 47
<211> LENGTH: 34
<212> TYPE: DNA
<213> ORGANISM: Artificial Sequence
<220> FEATURE:
<223> OTHER INFORMATION: primer

<400> SEQUENCE: 47
ggcctcgaga gtttattctt gacatgtagt gagg                          34

<210> SEQ ID NO 48
<211> LENGTH: 29
<212> TYPE: DNA
<213> ORGANISM: Artificial Sequence
<220> FEATURE:
<223> OTHER INFORMATION: primer

<400> SEQUENCE: 48
ggcgcatgct caacgacagg agcacgatc                                29

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
gagtcgcatt aagggagagc                                          20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
gctctccctt aatgcgactc                                          20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
cgtcctgtaa ggatcctcta                                          20

<210> SEQ ID NO 52
```

```
<211> LENGTH: 20
<212> TYPE: DNA
<213> ORGANISM: Artificial Sequence
<220> FEATURE:
<223> OTHER INFORMATION: primer

<400> SEQUENCE: 52
tagaggatcc ttacaggacg                                              20

<210> SEQ ID NO 53
<211> LENGTH: 26
<212> TYPE: DNA
<213> ORGANISM: Artificial Sequence
<220> FEATURE:
<223> OTHER INFORMATION: primer

<400> SEQUENCE: 53
ggcctcgagc tgtgcgaaga aattag                                       26

<210> SEQ ID NO 54
<211> LENGTH: 31
<212> TYPE: DNA
<213> ORGANISM: Artificial Sequence
<220> FEATURE:
<223> OTHER INFORMATION: primer

<400> SEQUENCE: 54
ggcgcatgct gttttcatt cacgcaggtt c                                  31

<210> SEQ ID NO 55
<211> LENGTH: 46
<212> TYPE: DNA
<213> ORGANISM: Artificial Sequence
<220> FEATURE:
<223> OTHER INFORMATION: primer

<400> SEQUENCE: 55
ggcgagctca cacaggaaac agaccatgtc tgaaattgtt gtctcc                 46

<210> SEQ ID NO 56
<211> LENGTH: 33
<212> TYPE: DNA
<213> ORGANISM: Artificial Sequence
<220> FEATURE:
<223> OTHER INFORMATION: primer

<400> SEQUENCE: 56
ggcggatcct tactcaaaca aattactatg cag                               33

<210> SEQ ID NO 57
<211> LENGTH: 46
<212> TYPE: DNA
<213> ORGANISM: Artificial Sequence
<220> FEATURE:
<223> OTHER INFORMATION: primer

<400> SEQUENCE: 57
ggcggatcca cacaggaaac agaccatgtt cacgggaagt attgtc                 46

<210> SEQ ID NO 58
<211> LENGTH: 28
<212> TYPE: DNA
<213> ORGANISM: Artificial Sequence
<220> FEATURE:
<223> OTHER INFORMATION: primer

<400> SEQUENCE: 58
```

```
ggctctagat tacagcaaac cggcatgc                                              28

<210> SEQ ID NO 59
<211> LENGTH: 46
<212> TYPE: DNA
<213> ORGANISM: Artificial Sequence
<220> FEATURE:
<223> OTHER INFORMATION: primer

<400> SEQUENCE: 59
ggctctagaa cacaggaaac agaccatgcc acattcactg ttcagc                          46

<210> SEQ ID NO 60
<211> LENGTH: 30
<212> TYPE: DNA
<213> ORGANISM: Artificial Sequence
<220> FEATURE:
<223> OTHER INFORMATION: primer

<400> SEQUENCE: 60
ggcgtcgact taaagcaatt ccagcgccag                                            30

<210> SEQ ID NO 61
<211> LENGTH: 48
<212> TYPE: DNA
<213> ORGANISM: Artificial Sequence
<220> FEATURE:
<223> OTHER INFORMATION: primer

<400> SEQUENCE: 61
ggcgagctca cacaggaaac agaccatgaa aaatgttggt tttatcgg                        48

<210> SEQ ID NO 62
<211> LENGTH: 28
<212> TYPE: DNA
<213> ORGANISM: Artificial Sequence
<220> FEATURE:
<223> OTHER INFORMATION: primer

<400> SEQUENCE: 62
ggcggatcct tacgccagtt gacgaagc                                              28

<210> SEQ ID NO 63
<211> LENGTH: 39
<212> TYPE: DNA
<213> ORGANISM: Artificial Sequence
<220> FEATURE:
<223> OTHER INFORMATION: primer

<400> SEQUENCE: 63
ggcacacagg aaacagacca tgcatgatgc aaacatccg                                  39

<210> SEQ ID NO 64
<211> LENGTH: 38
<212> TYPE: DNA
<213> ORGANISM: Artificial Sequence
<220> FEATURE:
<223> OTHER INFORMATION: primer

<400> SEQUENCE: 64
ggctctagat tacaaattat tgagatcaag tacatctc                                   38

<210> SEQ ID NO 65
<211> LENGTH: 45
<212> TYPE: DNA
```

```
<213> ORGANISM: Artificial Sequence
<220> FEATURE:
<223> OTHER INFORMATION: primer

<400> SEQUENCE: 65
ggctctagaa cacaggaaac agaccatgca gcagttacag aacat           45

<210> SEQ ID NO 66
<211> LENGTH: 29
<212> TYPE: DNA
<213> ORGANISM: Artificial Sequence
<220> FEATURE:
<223> OTHER INFORMATION: primer

<400> SEQUENCE: 66
ggcgcatgct tagtcgatgg tacgcagca                              29

<210> SEQ ID NO 67
<211> LENGTH: 46
<212> TYPE: DNA
<213> ORGANISM: Artificial Sequence
<220> FEATURE:
<223> OTHER INFORMATION: primer

<400> SEQUENCE: 67
ggctctagaa cacaggaaac agaccatgtt tgagaacatt accgcc           46

<210> SEQ ID NO 68
<211> LENGTH: 47
<212> TYPE: DNA
<213> ORGANISM: Artificial Sequence
<220> FEATURE:
<223> OTHER INFORMATION: primer

<400> SEQUENCE: 68
ggcgcatgcg acctcgaggt agtcgactta cagcactgcc acaatcg          47

<210> SEQ ID NO 69
<211> LENGTH: 23
<212> TYPE: DNA
<213> ORGANISM: Artificial Sequence
<220> FEATURE:
<223> OTHER INFORMATION: primer

<400> SEQUENCE: 69
cagcctgaat atactgcatt ctc                                    23

<210> SEQ ID NO 70
<211> LENGTH: 23
<212> TYPE: DNA
<213> ORGANISM: Artificial Sequence
<220> FEATURE:
<223> OTHER INFORMATION: primer

<400> SEQUENCE: 70
gagaatgcag tatattcagg ctg                                    23

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
gcattctcgc gatttcctcg                                        20
```

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72
cgaggaaatc gcgagaatgc                                                    20

<210> SEQ ID NO 73
<211> LENGTH: 22
<212> TYPE: DNA
<213> ORGANISM: Artificial Sequence
<220> FEATURE:
<223> OTHER INFORMATION: primer

<400> SEQUENCE: 73
cttaatcacc atgtcagaag tg                                                 22

<210> SEQ ID NO 74
<211> LENGTH: 22
<212> TYPE: DNA
<213> ORGANISM: Artificial Sequence
<220> FEATURE:
<223> OTHER INFORMATION: primer

<400> SEQUENCE: 74
cacttctgac atggtgatta ag                                                 22

<210> SEQ ID NO 75
<211> LENGTH: 21
<212> TYPE: DNA
<213> ORGANISM: Artificial Sequence
<220> FEATURE:
<223> OTHER INFORMATION: primer

<400> SEQUENCE: 75
cgtggcatta atccttgata c                                                  21

<210> SEQ ID NO 76
<211> LENGTH: 21
<212> TYPE: DNA
<213> ORGANISM: Artificial Sequence
<220> FEATURE:
<223> OTHER INFORMATION: primer

<400> SEQUENCE: 76
gtatcaagga ttaatgccac g                                                  21

<210> SEQ ID NO 77
<211> LENGTH: 46
<212> TYPE: DNA
<213> ORGANISM: Artificial Sequence
<220> FEATURE:
<223> OTHER INFORMATION: primer

<400> SEQUENCE: 77
ggcgagctca cacaggaaac agaccatggg cttagttgtg cagaaa                       46

<210> SEQ ID NO 78
<211> LENGTH: 30
<212> TYPE: DNA
<213> ORGANISM: Artificial Sequence
<220> FEATURE:

```
<223> OTHER INFORMATION: primer

<400> SEQUENCE: 78
ggcggatcct taacgacctg tgccgccata                              30

<210> SEQ ID NO 79
<211> LENGTH: 34
<212> TYPE: DNA
<213> ORGANISM: Artificial Sequence
<220> FEATURE:
<223> OTHER INFORMATION: primer

<400> SEQUENCE: 79
ggcggtacca gtttattctt gacatgtagt gagg                         34

<210> SEQ ID NO 80
<211> LENGTH: 29
<212> TYPE: DNA
<213> ORGANISM: Artificial Sequence
<220> FEATURE:
<223> OTHER INFORMATION: primer

<400> SEQUENCE: 80
ggcgggccct taaagcaatt ccagcgcca                               29

<210> SEQ ID NO 81
<211> LENGTH: 29
<212> TYPE: DNA
<213> ORGANISM: Artificial Sequence
<220> FEATURE:
<223> OTHER INFORMATION: primer

<400> SEQUENCE: 81
ggcgggccct gctggccttt tgctcacat                               29

<210> SEQ ID NO 82
<211> LENGTH: 29
<212> TYPE: DNA
<213> ORGANISM: Artificial Sequence
<220> FEATURE:
<223> OTHER INFORMATION: primer

<400> SEQUENCE: 82
ggcggtacct tacagcactg ccacaatcg                               29

<210> SEQ ID NO 83
<211> LENGTH: 29
<212> TYPE: DNA
<213> ORGANISM: Artificial Sequence
<220> FEATURE:
<223> OTHER INFORMATION: primer

<400> SEQUENCE: 83
ggcggtacct caacgacagg agcacgatc                               29
```

EXPRESSION OF RECOMBINANT TETRACYCLINE EFFLUX PUMPS FOR THE PRODUCTION OF LYSINE OR LYSINE-DERIVED PRODUCTS, AND METHODS AND APPLICATIONS THEREOF

CROSS-REFERENCE TO RELATED APPLICATIONS

The present application is division of U.S. patent application Ser. No. 15/517,633, filed on 7 Apr. 2017, now U.S. Pat. No. 10,400,257,which in turn is a national stage filing under 35 U.S.C. §371 of PCT/CN2014/088237, filed on 9 Oct. 2014. Each application is incorporated herein by reference in its entirety.

BACKGROUND

Current approaches to improve lysine production and the production of lysine-derived products, such as cadaverine, focus on the overexpression or attenuation of proteins involved in cellular metabolism. However, the yield obtained so far is not satisfying. Therefore, there is a need for new techniques resulting in higher yields of lysine and cadaverine.

SUMMARY OF THE INVENTION

One aspect of the invention relates to a first polypeptide comprising, consisting of, or consisting essentially of a tetracycline efflux pump polypeptide, a fragment thereof, or a mutant thereof. As used herein, the *E. coli* tetracycline efflux pump A is referred to as "TetA" and has the amino acid sequence of SEQ ID NO: 2. Examples of mutants of TetA include, without limitation, truncations of TetA such as TetA (aa1-185) having the polypeptide sequence of SEQ ID NO: 30 and TetA (aa1-96) having the polypeptide sequence of SEQ ID NO: 32. As used herein, "aa" refers to amino acid.

Another aspect of the invention relates to a non-naturally occurring first polynucleotide encoding one or more first polypeptides as disclosed herein. As used herein, the *E. coli* tetracycline efflux pump A gene is referred to as "*E.coli* tetA" and comprises, consists of, or consists essentially of the polynucleotide sequence of SEQ ID NO: 1. Examples of mutants of tetA include, without limitation, truncations of tetA such as tetA (nt 1-558) having the polynucleotide sequence of SEQ ID NO: 29 and tetA (nt 1-291) having the polynucleotide sequence of SEQ ID NO: 31. As used herein, "nt" refers to nucleotide.

Another aspect of the invention relates to a first expression plasmid vector comprising, consisting of, or consisting essentially of one or more first polynucleotides as disclosed herein; and a backbone plasmid capable of autonomous replication in a host cell, wherein the first expression plasmid vector is used for production of lysine or a lysine-derived product. In certain embodiments, the first expression plasmid vector further comprises one or more second polynucleotides selected from the group consisting of a third polynucleotide encoding a third polypeptide comprising a lysine decarboxylase polypeptide, a fragment thereof or a mutant thereof, and a fourth polynucleotide encoding a fourth polypeptide comprising a lysine biosynthesis polypeptide, a fragment thereof or a mutant thereof.

Another aspect of the invention relates to a transformant comprising, consisting of, or consisting essentially of one or more first expression plasmid vectors as described herein in a host cell. In certain embodiments, the transformant as described herein, further comprises, consists of, or consists essentially of one or more second expression plasmid vectors comprising, consisting of, or consisting essentially of one or more fifth polynucleotides selected from the group consisting of a first polynucleotide as disclosed herein, a third polynucleotide as disclosed herein, and a fourth polynucleotide as disclosed herein; and a backbone plasmid capable of autonomous replication in a host cell, wherein the one or more second expression plasmid vectors are used for production of lysine or a lysine-derived product.

Another aspect of the invention relates to a mutant host cell comprising, consisting of, or consisting essentially of one or more first polynucleotides as disclosed herein integrated into a chromosome of a host cell. In certain embodiments, mutant host cell further comprises, consists of, or consists essentially of one or more second polynucleotides selected from the group consisting of third polynucleotides as disclosed herein, and fourth polynucleotides as disclosed herein.

Another aspect of the invention relates to a method for producing lysine comprising obtaining a transformant and/or mutant host cell as disclosed herein, culturing the transformant and/or mutant host cell under conditions effective for the expression of the lysine; and harvesting the lysine.

Another aspect of the invention relates to a method for producing cadaverine (1,5-pentanediamine) comprising cultivating a transformant and/or mutant host cell as disclosed herein, producing cadaverine using the culture obtained herein to decarboxylate lysine, and extracting and purifying cadaverine using the culture obtained herein.

Other aspects of the invention relate to polyamides and 1,5-diisocyanatopentane prepared from biobased cadaverine prepared as disclosed herein, and compositions and preparation methods thereof.

BRIEF DESCRIPTION OF THE DRAWINGS

FIG. 1: Polymerase chain reaction (PCR) primer sequences used to construct the recombinant expression plasmid vectors according to an embodiment of the invention. Primer sequences used to clone and truncate tetA, cadA, and various genes involved in the lysine biosynthetic pathway are provided.

FIG. 2: A table showing the plasmids and strains used in the Examples in addition to the corresponding enzymes being overexpressed and the genes encoding the enzymes.

DETAILED DESCRIPTION OF THE INVENTION

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

As disclosed herein, it has been found that expression of a tetracycline efflux pump has resulted in unexpectedly high yields of lysine and cadaverine production. Furthermore, it has unexpectedly been found that expression of various mutants of the tetracycline efflux pump have resulted in high cadaverine productions.

As used herein, the term "one or more" items (e.g. without limitation, polynucleotides, polypeptides, expression plasmid vectors, amino acids, nucleotides, mutations, plasmids, enzymes, proteins, sources, diamines, dicarboxylic acids, and polyamides) means that when there are a plurality of the items, said items may be the same or different.

One aspect of the invention relates to a first polypeptide comprising, consisting of, or consisting essentially of a tetracycline efflux pump polypeptide, a fragment thereof, or a mutant thereof. In certain embodiments, the tetracycline efflux pump polypeptide comprises, consists of, or consists essentially of the amino acid sequence of SEQ ID NO: 2 (TetA), a fragment thereof, or a mutant thereof.

In certain embodiments, the first polypeptide comprises a tetracycline efflux pump polypeptides selected from the group consisting of Tet, TetA, TetB, TetC, TetD, TetE, TetF, TetG, TetH, TetJ, TetK, TetL, TetM, TetO, TetP(A), TetP(B), TetQ, TetS, TetT, TetU, TetV, TetW, TetX, TetY, TetZ, TetA30, fragments thereof, and mutants thereof. For example, without limitation, the first polypeptide may comprise any of the tetracycline efflux pump polypeptides listed in Table 1, a fragment thereof, or a mutant thereof.

TABLE 1

Genes that encode tetracycline efflux pumps and corresponding genera

| Genes | Polypeptides | Source (Genus) |
|---|---|---|
| tetA | TetA | *Aeromonas, Citrobacter, Edwardsiella, Escherichia, Klebsiella, Plesimonas, Proteus, Pseudomonas, Salmonella, Serratia, Shigella, Vibrio* |
| tetB | TetB | *Actinobacillus, Aeromonas, Citrobacter, Enterobacter, Escherichia, Haempphilus. Klebsiella, Moraxella, Pasteurella, Plesimonas, Proteus, Providencia, Salmonella, Serratia, Shigella, Treponema, Vibrio, Yersinia* |
| tetC | TetC | *Citrobacter, Enterobacter, Escherichia, Proteus, Pseudomonas, Salmonella, Serratia, Shigella, Vibrio* |
| tetD | TetC | *Aeromonas, Citrobacter, Edwardsiella, Enterobacter, Escherichia, Klebsiella, Pasteurella, Plesimonas, Salmonella, Shigella, Vibrio, Yersinia* |
| tetE | TetE | *Aeromonas, Alcaligenes, Escherichia, Providencia, Pseudomonas, Serratia, Shigella, Vibrio* |
| tetF | TetF | *Baceriodes fragilis* |
| tetG | TetG | *Pseudomonas, Salmonella, Vibrio* |
| tetH | TetH | *Pasteurella* |
| tetJ | TetJ | *Proteus mirabilis* |
| tetK | TetK | *Bacillus, Clostridium, Enterococcus, Eubacterium, Haempphilus. Listeria, Mycobacterium, Nocardia, Peptostreptococcus, Staphylococcus, Streptococcus, Streptomyces* |
| tetL | TetL | *Actinomyces, Bacillus, Clostridium, Enterococcus, Listeria, Mycobacterium, Peptostreptococcus, Staphylococcus, Streptococcus, Streptomyces* |
| tetM | TetM | *Aerococcus, Actinomyces, Bacterionema, Bifidobacterium, Clostridium, Corynebacterium, Enterococcus, Eubacterium, Gardnerella, Gemella, Listeria, Mycoplasma, Peptostreptococcus, Staphylococcus, Streptococcus, Ureaplasma, Campylobacter, Eikenella, Fusobacterium, Haemophilus, Kingella, Neisseria, Pasteurella, Prevotella, Veillonella* |
| tetO | TetO | *Aerococcus, Enterococcus, Lactobacillus, Mobiluncus, Peptostreptococcus, Staphylococcus, Streptococcus, Campylobacter* |
| tetP(A) | TetP(A) | *Clostridium, Helicobacter* |
| tetP(B) | TetP(B) | *Clostridium* |
| tetQ | TetQ | *Baceriodes, Capnocytophaga, Mitsuokella, Porphyromonas, Prevotella, Veillonella, Eubacterium, Lactobacillus, Mobiluncus, Peptostreptococcus, Streptococcus* |
| tetS | TetS | *Enterococcus, Lactobacillus, Listeria* |
| tetT | TetT | *Streptococcus* |
| tetU | TetU | *Enterococcus* |
| tetV | TetV | *Mycobacterium* |
| tetW | TetW | *Butyrivibrio* |
| tetX | TetX | *Baceriodes* |
| tetY | TetY | pIE1120 |
| tetZ | TetZ | *Corynebacterium* |
| tetA(30) | TetA(30) | *Agrobacterium* |

In certain embodiments, the first polypeptide comprises, consists of, or consists essentially of the amino acid sequence of SEQ ID NO: 2 (TetA), a fragment thereof, or a mutant thereof. A mutant of TetA may include a deletion, substitution, addition, and/or insertion of one or more amino acids to the amino acid sequence of SEQ ID NO: 2, while the mutant of TetA provides substantially the same function as TetA (i.e., the mutant of TetA has about 80% or higher tetracycline efflux pump activity compared to that of TetA; about 90% or higher tetracycline efflux pump activity compared to that of TetA; about 95% or higher tetracycline efflux pump activity compared to that of TetA; about 97% or higher tetracycline efflux pump activity compared to that of TetA; about 99% or higher tetracycline efflux pump activity compared to that of TetA; or about 100% or higher tetracycline efflux pump activity compared to that of TetA.)

Examples of mutants of TetA include, without limitation, SEQ ID NO: 30 (TetA (aa1-185; where "aa" refers to amino acids)) and SEQ ID NO: 32 (TetA (aa1-96)). Other examples of TetA mutants may include TetA mutants that are truncated at structural loop regions connecting alpha helices within the TetA polypeptide. In certain embodiments, TetA mutants may include any truncations made in loop three of the TetA protein such as TetA aa1-97, TetA aa 1-98, TetA aa 1-99, TetA aa 1-100, TetA aa 1-101, TetA aa 1-102, TetA aa 1-103, or TetA aa 1-104. In certain embodiments, TetA mutants may include any truncations made in loop four of the TetA protein such as TetA aa1-124, TetA aa 1-125, TetA aa 1-126, TetA aa 1-127, TetA aa 1-128, TetA aa 1-129, TetA aa 1-130, TetA aa 1-131, TetA aa 1-132, or TetA aa 1-133. In certain embodiments, TetA mutants may include any truncations made in loop five of the TetA protein such as TetA aa1-155, TetA aa 1-156, TetA aa 1-157, TetA aa 1-158, TetA aa 1-159, TetA aa 1-160, TetA aa 1-161, or TetA aa 1-162. In certain embodiments, TetA mutants may include any truncations made in loop six of the TetA protein such as TetA aa1-182, TetA aa 1-183, TetA aa 1-184, TetA aa 1-185, TetA aa 1-186, TetA aa 1-187, TetA aa 1-188, TetA aa 1-189, TetA aa 1-190, TetA aa1-191, TetA aa 1-192, TetA aa 1-193, TetA aa 1-194, TetA aa 1-195, TetA aa 1-196, TetA aa 1-197, TetA aa 1-198, TetA aa 1-199, TetA aa1-200, TetA aa 1-201, TetA aa 1-202, TetA aa 1-203, TetA aa 1-204, TetA aa 1-205, TetA aa 1-206, TetA aa 1-207, TetA aa 1-208, TetA aa 1-209, TetA aa 1-210, TetA aa 1-211, TetA aa 1-212, TetA aa 1-213, or TetA aa 1-214. In certain embodiments, TetA mutants may include any truncations made in loop seven of the TetA protein such as TetA aa1-237, TetA aa 1-238, TetA aa 1-239, TetA aa 1-240, TetA aa 1-241, TetA aa 1-242, TetA aa 1-243, TetA aa 1-244, or TetA aa 1-245. In certain embodiments, TetA mutants may include any truncations made in loop eight of the TetA protein such as TetA aa1-268, TetA aa 1-269, TetA aa 1-270, TetA aa 1-271, TetA aa 1-272, TetA aa 1-273, TetA aa 1-274, TetA aa 1-275, TetA aa 1-276, TetA aa 1-277, or TetA aa 1-278. In certain embodiments, TetA mutants may include any truncations made in loop nine of the TetA protein such as TetA aa1-321, TetA aa 1-322, TetA aa 1-323, TetA aa 1-324, TetA aa 1-325, TetA aa 1-326, TetA aa 1-327, TetA aa 1-328, TetA aa 1-329, TetA aa 1-330, TetA aa 1-331, TetA aa 1-332, TetA aa 1-333, TetA aa 1-334, TetA aa 1-335, TetA aa 1-336, TetA aa 1-337, TetA aa 1-338, or TetA aa 1-339. In certain embodiments, TetA mutants may include any truncations made in loop ten of the TetA protein such as TetA aa1-360, TetA aa 1-361, TetA aa 1-362, TetA aa 1-363, TetA aa 1-364, TetA aa 1-365, TetA aa 1-366, or TetA aa 1-367.

As used herein, a polypeptide comprising a specific polypeptide sequence may include fragments, and/or mutants of the specific polypeptide sequence, while still providing substantially the same function as the whole original unmutated specific polypeptide sequence. A fragment of a polypeptide means a part of the polypeptide that provides substantially the same function as the whole polypeptide. Examples of mutants of a specific polypeptide sequence include deletions, substitutions, additions, and/or insertions of one or more amino acids to the specific polypeptide sequence. For example, a fragment or mutant of TetA possesses substantially the same function of the TetA polypeptide (e.g. tetracycline efflux pump activity).

Another aspect of the invention relates to a first polynucleotide encoding one or more first polypeptides that are the same or different as disclosed herein. In one embodiment, the first polypeptide comprises, consists of, or consists essentially of a tetracycline efflux pump polypeptide, a fragment thereof or a mutant thereof. When there are a plurality of the first polypeptides, each first polypeptide may be the same or different, and may be expressed individually or as a fusion protein.

In certain embodiments, the first polynucleotide sequence preferably comprises one or more of a E. coli tetracycline efflux pump gene tetA (SEQ ID NO: 1), a fragment thereof, and/or a mutant thereof. In certain embodiments, the first polynucleotide may encode any of the tetracycline efflux pumps as disclosed herein. In certain embodiments, the first polynucleotide sequence may be selected from the group consisting of SEQ ID NO: 29 (tetA (nt 1-558)), SEQ ID NO: 31 (tetA (nt 1-291), and codon optimized tetA's.

In certain embodiments, the first polynucleotide sequence comprises one, two, three, four, five, six, seven, eight, nine, or ten tetracycline efflux pump genes independently selected from the group consisting of tet, tetA, tetB, tetC, tetD, tetE, tetF, tetG, tetH, tetJ, tetK, tetL, tetM, tetO, tetP(A), tetP(B), tetQ, tetS, tetT, tetU, tetV, tetW, tetX, tetY, tetZ, tetA30, fragments thereof, and mutants thereof. For example, the first polynucleotide sequence may, without limitation, comprise any of the tetracycline efflux pump genes listed in Table 1, a fragment thereof, or a mutant thereof. In certain embodiments, the tetracycline efflux pump genes may, without limitation, be from any of the corresponding genera listed in Table 1.

In certain embodiments, the first polynucleotide comprises, consists of, or consists essentially of the polynucleotide tetracycline efflux pump gene tetA (SEQ ID NO: 1), a mutant thereof, or a fragment thereof. A mutant of tetA may include a deletion, a substitution, an addition, and/or an insertion of one or more nucleotides to the polynucleotide sequence of SEQ ID NO: 1, while the protein encoded by the mutant of tetA provides substantially the same function as TetA (i.e., the mutant of TetA has about 80% or higher tetracycline efflux pump activity compared to that of TetA; about 90% or higher tetracycline efflux pump activity compared to that of TetA; about 95% or higher tetracycline efflux pump activity compared to that of TetA; about 97% or higher tetracycline efflux pump activity compared to that of TetA; about 99% or higher tetracycline efflux pump activity compared to that of TetA; or about 100% or higher tetracycline efflux pump activity compared to that of TetA).

In certain embodiments, the first polynucleotide may be a recombinant or non-naturally occurring polynucleotide. In certain embodiments, the first polynucleotide may be cDNA. In certain embodiments, the first polynucleotide may be obtained by codon optimization for optimal polypeptide expression in a particular microorganism (e.g., E. coli, H. alvei, or P. aeruginosa).

Nucleotide sequences, polynucleotides, and DNA molecules as used herein are not limited to the functional region, and may include at least one of an expression suppression region, a coding region, a leader sequence, an exon, an intron, and an expression cassette (see, e.g. Papadakis et al., "Promoters and Control Elements: Designing Expression Cassettes for Gene Therapy," Current Gene Therapy (2004), 4, 89-113). Furthermore, nucleotide sequences or polynucleotides may include double strand DNA or single strand DNA (i.e., a sense chain and an antisense chain constituting the double strand DNA), or RNA. A polynucleotide containing a specific polynucleotides sequence may include fragments, and/or mutants of the specific polynucleotides sequence. A fragment of a polynucleotide means a part of the polynucleotide that encodes a polypeptide which provides substantially the same function as the polypeptide encoded by the whole polynucleotide. Examples of mutants of a specific polynucleotides sequence include naturally occurring allelic mutants; artificial mutants; and polynucleotides sequences obtained by deletion, substitution, addition, and/or insertion of one or more nucleotides to the specific polynucleotides sequence. It should be understood that such fragments, and/or mutants of a specific polynucleotides sequence encode polypeptides having substantially the same function as the polypeptide encoded by the original, specific polynucleotides sequence. For example, a fragment and/or mutant of tetA encodes a polypeptide that possesses substantially the same function of TetA (e.g. tetracycline efflux pump activity).

Codon optimization is a technique that may be used to maximize the protein expression in an organism by increasing the translational efficiency of the gene of interest. Different organisms often show particular preferences for one of the several codons that encode the same amino acid due to mutational biases and natural selection. For example, in fast growing microorganisms such as *E. coli*, optimal codons reflect the composition of their respective genomic tRNA pool. Therefore, the codons of low frequency of an amino acid may be replaced with codons for the same amino acid but of high frequency in the fast growing microorganism. Accordingly, the expression of the optimized DNA sequence is improved in the fast growing microorganism. See, e.g. http://www.guptalab.org/shubhg/pdf/shubhra_codon.pdf for an overview of codon optimization technology, which is incorporated herein by reference in its entirety. As provided herein, polynucleotide sequences may be codon optimized for optimal polypeptide expression in a particular microorganism including, but not limited to, *E. coli, H. alvei*, and *P. aeruginosa*.

In certain embodiments, mutants of a polynucleotide can be obtained from codon optimization of the polynucleotide to decrease the guanine (G) and cytosine (C) polynucleotide content thereof for improved protein expression. A genome is considered GC-rich if about 50% or more of its bases are G or C. A high GC content in the polynucleotide sequence of interest may lead to the formation of secondary structure in the mRNA, which can result in interrupted translation and lower levels of expression. Thus, changing G and C residues in the coding sequence to A and T residues without changing the amino acids may provide higher expression levels.

Another aspect of the invention relates to a first expression plasmid vector comprising, consisting of, or consisting essentially of:
one or more first polynucleotides that are the same or different, and each encodes one or more first polypeptides that are the same or different and each comprises, consists of, or consists essentially of a tetracycline efflux pump polypeptide, a fragment thereof, or a mutant thereof, and
a backbone plasmid capable of autonomous replication in a host cell,
wherein the first expression plasmid vector is used for production of lysine or a lysine-derived product.

In one embodiment, there are a plurality of the first polypeptides, each first polypeptide may be the same or different, and may be expressed individually or as a fusion protein.

As used herein, the term "host cell" refers to a microorganism cell that may be any cell that can be transformed with an expression plasmid vector (e.g., *Pseudomonas* (e.g., *P. aeruginosa*), *Escherichia* (e.g., *E. coli*), *Corynebacterium* (e.g., *Corynebacterium glutamicum*), *Bacilli, Hafnia* (e.g., *Hafnia alvei*), *Brevibacterium, Lactobacillus* (e.g., *Lactobacillus pentosus, Lactobacillus plantarum, Lactobacillus saerimnen*), *Lactococcus* (e.g., *Lactococcus lactis, Lactococcus lactis* ssp. *cremoris, Lactococcus lactis* ssp. *lactis*), and *Streptococcus* (e.g., *Streptococcus thermophilus*)).

An *E. coli* cell may be any of the *E. coli* strains derived from *E. coli* K12 (e.g., MG1655, W3110, DH10b, DH1, BW2952 and strains derived therefrom) or *E. coli* B, or strains derived therefrom.

In certain embodiments, the host cell may contain one or more endogenous plasmids. In certain embodiments, the host cell does not contain endogenous plasmids. The term "cure" as used herein means to remove one or more endogenous plasmids from a host cell. In certain embodiments, a host cell may be "cured" of all endogenous plasmids by removing all endogenous plasmids from the host cell. In certain embodiments, a host cell may be "cured" of one or more endogenous plasmids by removing only the one or more endogenous plasmids that is targeted for removal from the cell.

In certain embodiments, the host cell may be a prokaryotic cell (e.g. is., *H. alvei*) containing endogenous plasmids that encode specific toxin/antitoxin gene pairs. Such toxin/antitoxin gene pairs play a role in maintenance of the genetic information and response to stress. (See, Wertz et al. "Chimeric nature of two plasmids of Hafnia alvei encoding the bacteriocins alveicins A and B." Journal of Bacteriology, (2004) 186: 1598-1605.) As long as the cell has one or more plasmids comprising an antitoxin gene, the toxin is neutralized by the antitoxin that is continuously expressed by the one or more plasmids to keep the cells alive. In certain prokaryotes, the antitoxin protein degrades faster than the toxin protein. If the plasmid comprising the antitoxin gene is lost from the cell, the toxin protein will exist longer than the antitoxin protein in the cell and kill or inhibit the growth of the cell. Therefore, plasmids comprising the antitoxin or the toxin/antitoxin gene are preferably maintained to keep the host cell alive.

As used herein, a toxin/antitoxin gene pair has two genes, one is a toxin gene which expresses a polypeptide toxic to a host cell, and the other is an antitoxin gene which neutralizes the toxic polypeptide in the host cell. Examples of the toxin/antitoxin gene pair include, without limitation, abt/abi gene pair and aat/aai gene pair, fragments thereof, and mutants thereof. In some embodiments, the toxin polynucleotide sequence comprises, consists of, or consists essentially of the nucleotide sequence of SEQ ID NO: 12 or SEQ ID NO: 14, fragments thereof, or mutants thereof. In some embodiments, the antitoxin polynucleotide sequence comprises, consists of, or consists essentially of the nucleotide sequence of SEQ ID NO: 13 or SEQ ID NO: 15, fragments thereof, or mutants thereof.

In certain embodiments, the host cell may be any *H. alvei* strain, e.g., endogenous plasmid-free *H. alvei* strains or *H. alvei* strains containing endogenous plasmids. For example, the host cell may be an *H. alvei* strain containing one or more pAlvA plasmids or the cured strains thereof (pAlvA-strains), or an *H. alvei* strain containing one or more pAlvB plasmids and the cured strains thereof (pAlvB-strains).

In certain embodiments, the expression plasmid vector disclosed herein (e.g. the first expression plasmid vector) may further comprise one or more antitoxin genes independently selected from the group consisting of abi gene, aai gene, mutations and fragments thereof, and/or one or more toxin/antitoxin gene pairs independently selected from the group consisting of abt/abi gene pair and aat/aai gene pair, and mutations and fragments thereof. For example, in certain embodiments, an expression plasmid vector (e.g. the first expression plasmid vector) may further comprise an antitoxin polynucleotide that counteracts a toxin polypeptide that is harmful to the host cell, and a toxin polynucleotide sequence encoding the toxin polypeptide.

In certain embodiments, the host cell is an industrial strain suitable to be used in industrial-scale or large-scale production. For example, industrial strains may be cultivated in a fermenter. The scale of culture may range from hundreds of liters to millions of liters. On the other hand, a laboratory strain usually is cultivated in a few liters or less. In certain embodiments, an industrial strain may grow in a simpler or more economical medium than laboratory strains.

A backbone plasmid capable of autonomous replication in a host cell may be any plasmid that can replicate in the host cell. In one embodiment, an expression plasmid vector comprises a backbone plasmid that can replicate in *E. coli*. In another embodiment, an expression plasmid vector comprises a backbone plasmid that can replicate in *H. alvei*. Examples of the backbone plasmids include, without limitation, backbone plasmids that can replicate in *E. coli* strains, e.g. pUC (e.g. pUC18 and pUC19 plasmids), pBR322, pSC101, p15a, pACYC, pET, and pSC101 plasmids, and plasmids derived therefrom.

In certain embodiments, the mutants of a polynucleotide can be obtained from codon optimization of the polynucleotide for a particular microorganism (e.g., *E. coli*, *H. alvei*, or *P. aeruginosa*) to enhance polypeptide expression.

In certain embodiments, the first expression plasmid vector may be used for the production of lysine or a lysine derived product as described herein. In certain embodiments, a lysine derived product may be cadaverine as described herein.

In certain embodiments, the first expression plasmid vector further comprises one or more sixth polynucleotides that are the same or different, and each encodes a sixth polypeptide that comprises, consists of, or consists essentially of an antibiotic resistance protein, a fragment, or a mutant thereof. When there are a plurality of the sixth polynucleotides, the sixth polypeptides encoded by the sixth polynucleotides may be the same and different, and may be expressed individually or as a fusion protein.

In certain embodiments, the antibiotic resistance protein may be a tetracycline resistance protein or an oxytetracycline-resistance protein. In certain embodiments, the antibiotic resistance protein may be selected from the group that comprises, consists of, or consists essentially of OtrA, OtrB, OtrC, Tcr3, a fragment, and/or mutant thereof. In certain embodiments, OtrA may be from the genus *Mycobacterium* or *Streptomyces*. In certain embodiments, OtrB, OtrC, and Tcr3 may be from the genus *Streptomyces*. In certain embodiments, the sixth polynucleotide may be selected from the group that comprises, consists of, or consists essentially of otrA, otrB, otrC, tcr3, a fragment, and/or mutant thereof. In certain embodiments, otrA may be from the genus *Mycobacterium* or *Streptomyces*. In certain embodiments, otrB, otrC, and tcr3 may be from the genus *Streptomyces*.

In certain embodiments, the first expression plasmid vector comprising, consisting of, or consisting essentially of:
one or more first polynucleotides that are the same or different, and each encodes one or more first polypeptides that are the same or different and each comprises, consists of, or consists essentially of a tetracycline efflux pump polypeptide, a fragment thereof, or a mutant thereof;
one or more second polynucleotides that are the same or different and independently selected from the group consisting of:
a third polynucleotide encoding a third polypeptide comprising, consisting of, or consists essentially of a lysine decarboxylase polypeptide, a fragment thereof or a mutant thereof, and
a fourth polynucleotide encoding a fourth polypeptide comprising, consisting of, or consisting essentially of a lysine biosynthesis polypeptide, a fragment thereof or a mutant thereof; and
a backbone plasmid capable of autonomous replication in a host cell,
wherein the first expression plasmid vector is used for production of lysine or a lysine-derived product.

In certain embodiments, when there are a plurality of the second polynucleotides, each third polypeptide may be the same or different and each fourth polypeptide may be the same or different; the third and fourth polypeptides may be expressed individually or as a fusion protein.

In certain embodiments, the third polynucleotide encodes a third polypeptide that comprises, consists of, or consists essentially of a lysine decarboxylase polypeptide, a fragment thereof, or a mutant thereof.

In certain embodiments, the third polynucleotide may be selected from the group that comprises, consists of, or consists essentially of SEQ ID NO: 41 (cadA), SEQ ID NO: 42 (ldcC), SEQ ID NO: 8 (ldc2), fragments thereof, and mutants thereof. In certain embodiments, third polynucleotide is selected from the group that comprises, consists of, or consists essentially of SEQ ID NO: 10 (ldc2 co-1), SEQ ID NO: 34 (ldc2 co-1 C332G), SEQ ID NO: 35 (ldc2 co-1 A785C), SEQ ID NO: 36 (ldc2 co-1 A795C), SEQ ID NO: 37 (ldc2 co-1 C332G/A785C), SEQ ID NO: 38 (ldc2 co-1 C332G/A795C), SEQ ID NO: 39 (ldc2 co-1 A785C/A795C), and SEQ ID NO: 40 (ldc2 co-1 C332G/A785C/A795C).

In certain embodiments, the third polypeptide may comprise, consist of, or consist essentially of *Escherichia coli* CadA (SEQ ID NO: 6), *Escherichia coli* LdcC (SEQ ID NO: 7), *Pseudomonas aeruginosa* Ldc2 (SEQ ID NO: 9), a fragment thereof, or a mutant thereof. In certain embodiments, the lysine decarboxylase may be a lysine decarboxylase from a species that is homologous to *E. coli* LdcC or CadA. For example, the lysine decarboxylase may be *Shigella sonnei* CadA or *Salmonella enterica* lysine decarboxylase, a fragment, or a mutant thereof.

Examples of mutants of Ldc2 include, without limitation, SEQ ID NO: 11 (Ldc2 S111C), SEQ ID NO: 16 (Ldc2 N262T), SEQ ID NO: 17 (Ldc2 K265N), SEQ ID NO: 18 (Ldc2 S111C/N262T), SEQ ID NO: 19 (Ldc2 S111C/K265N), SEQ ID NO: 20 (Ldc2 N262T/K265N), and SEQ ID NO: 21 (Ldc2 S111C/N262T/K265N), homologous polypeptides of Ldc2, homologous polypeptides of Ldc2 S111C (e.g. Ldc2 S111X), homologous polypeptides of Ldc2 N262T (e.g. Ldc2 N262X'), homologous polypeptides of Ldc2 K265N (e.g. Ldc2 K265X'), homologous polypeptides of Ldc2 S111C/N262T (e.g. Ldc2 S111X/N262X'), homologous polypeptides of Ldc2 S111C/K265N (e.g. Ldc2 S111X/K265X"), homologous polypeptides of Ldc2 N262T/K265N (e.g. Ldc2 N262X'/K265X"), and homologous polypeptides of Ldc2 S111C/N262T/K265N (e.g. Ldc2 S111X/N262X'/K265X"). X is any amino acid that is not serine, X' is any amino acid that is not asparagine, and X" is any amino acid that is not lysine. As used herein, a homologous polypeptide is at least about 90%, at least about 95%, at least about 97%, at least about 98%, or at least about 99% homologous with the polypeptide. When a Ldc2 mutant has multiple mutations, each mutation may be the same or different.

In certain embodiments, the third polypeptides are mutants of Ldc2, and the corresponding third polynucleotides encoding the third polypeptides are polynucleotides encoding Ldc2 (e.g. Idc2 (SEQ ID NO: 8)), a codon optimized Idc2 (e.g. Idc2-col, SEQ ID NO: 10)) containing one or more suitable nucleotide mutations that are the same or different and independently selected from the group consisting of a mutation at nucleotide position 331, a mutation at nucleotide position 332, a mutation at nucleotide position 333, a mutation at nucleotide position 784, a mutation at nucleotide position 785, a mutation at nucleotide position 786, a mutation at nucleotide position 793, a mutation at nucleotide position 794, and a mutation at nucleotide position 795.

In certain embodiments, the third polypeptides are mutants of Ldc2, and the corresponding third polynucleotides encoding the third polypeptides are polynucleotides encoding Ldc2 (e.g. Idc2 (SEQ ID NO: 8), a codon optimized Idc2 (e.g. Idc2-col, SEQ ID NO: 10)) containing one or more suitable nucleotide mutations that are the same or different and independently selected from the group consisting of a mutation at nucleotide position 332, a mutation at nucleotide position 785, and a mutation at nucleotide position 795. In certain examples, without limitation, the nucleotide at position 332 may be mutated to G, the nucleotide at position 785 may be mutated to a C, and the nucleotide at position 795 may be mutated to a T or C.

In certain embodiments, a lysine decarboxylase polypeptide may include a deletion, substitution, addition, and/or insertion of one or more amino acids to the amino acid sequence of a lysine decarboxylase polypeptide, while the mutant of lysine decarboxylase polypeptide provides substantially the same function as a lysine decarboxylase polypeptide (i.e., the mutant of a lysine decarboxylase polypeptide has about 80% or higher lysine decarboxylase activity compared to that of a lysine decarboxylase polypeptide; about 90% or higher lysine decarboxylase activity compared to that of a lysine decarboxylase polypeptide; about 95% or higher lysine decarboxylase activity compared to that of a lysine decarboxylase polypeptide; about 97% or higher lysine decarboxylase activity compared to that of a lysine decarboxylase polypeptide; about 99% or higher lysine decarboxylase activity compared to that of a lysine decarboxylase polypeptide; or about 100% or higher lysine decarboxylase activity compared to that of a lysine decarboxylase polypeptide).

In certain embodiments, the fourth polynucleotide encodes a fourth polypeptide that comprises, consists of, or consists essentially of a lysine biosynthesis polypeptide, a fragment thereof, or a mutant thereof. In certain embodiments, the fourth polynucleotide may be a gene selected from the group consisting of sucA, ppc, aspC, lysC, asd, dapA, dapB, dapD, argD, dapE, dapF, lysA, ddh, pntAB, cyoABE, gadAB, ybjE, gdhA, gltA, sucC, gadC, acnB, pflB, thrA, aceA, aceB, gltB, aceE, sdhA, murE, speE, speG, puuA, puuP, ygjG, fragments thereof, and mutants thereof. For example, without limitation, the fourth polynucleotide may comprise the sequence of any one of the E. coli genes, fragments thereof, or mutants thereof, listed in Table 2.

In certain embodiments, the fourth polynucleotide may comprise the sequence of a gene involved in lysine biosynthesis that is homologous to any one of the genes listed in Table 2. For example, the fourth polynucleotide may comprise the sequence of a gene involved in lysine biosynthesis that is from a species other than E. coli. In certain embodiments, the fourth polynucleotide may comprise the sequence of a polynucleotide sequence decoding the aspartokinase, LysC, from Streptomyces lividans (GenBank EOY48571.1). As used herein, a gene that is homologous to an E. coli gene has a polynucleotide sequence with at least about 90%, at least about 95%, at least about 97%, at least about 98%, or at least about 99% sequence homology with the polynucleotide sequence of the E. coli gene.

TABLE 2

E. coli Proteins/genes involved in lysine biosynthesis.

| Protein | Gene | GenBank Accession No. |
|---|---|---|
| α-ketoglutarate dehydrogenase (SucA) | sucA | YP_489005.1 |
| Phosphoenolpyruvate carboxylase (PPC) | ppc | AAC76938.1 |
| aspartate transaminase (AspC) | aspC | AAC74014.1 |
| aspartate kinase (LysC) | lysC | NP_418448.1 |
| aspartate semialdehyde dehydrogenase (Asd) | asd | AAC76458.1 |
| dihydrodipicolinate synthase (DapA) | dapA | NP_416973.1 |
| dihydropicolinate reductase (DapB) | dapB | AAC73142.1 |
| tetrahydrodipicoinate succinylase (DapD) | dapD | AAC73277.1 |
| N-succinyldiaminopimelate aminotransferase (ArgD) | argD | AAC76384.1 |
| N-succinyl-L-diaminopimelate deacylase (DapE) | dapE | AAC75525.1 |
| diaminopimelate epimerase (DapF) | dapF | AAC76812.2 |
| diaminopimelate decarboxylase (LysA) | lysA | AAC75877.1 |
| meso-diaminopimelate dehydrogenase (Ddh) | ddh | P04964.1 |
| pyridine nucleotide transhydrogenase (PntAB) | pntAB | AAC74675.1, AAC74674.1 |
| cytochrome O oxidase (CyoABE) | cyoABE | AAC73535.1, AAC73534.1, AAC73531.1 |
| glutamate decarboxylase (GadAB) | gadAB | AAC76542.1, AAC74566.1 |
| L-amino acid efflux transporter (YbjE) | ybjE | AAC73961.2 |
| glutamate dehydrogenase (GdhA) | gdhA | AAC74831.1 |
| citrate synthase (GltA) | gltA | AAC73814.1 |
| succinyl-coA synthase (SucC) | sucC | AAC73822.1 |
| glutamate-GABA antiporter (GadC) | gadC | AAC74565.1 |
| aconitase B (AcnB) | acnB | AAC73229.1 |
| pyruvate-formate lyase (PflB) | pflB | AAC73989.1 |
| aspartate kinase/homoserine dehydrogenase (ThrA) | thrA | AAC73113.1 |
| isocitrate lyase (AceA) | aceA | AAC76985.1 |
| malate synthase (AceB) | aceB | AAC76984.1 |
| glutmate synthase (GltB) | gltB | AAC76244.2 |
| pyruvate dehydrogenase (AceE) | aceE | AAC73225.1 |
| succinate dehydrogenase (SdhA) | sdhA | AAC73817.1 |
| UDP-N-acetylmuramoyl-L-alanyl-D-glutamate:meso-diaminopimelate ligase (MurE) | murE | AAC73196.1 |
| putrescine/cadaverine aminopropyltransferase (SpeE) | speE | AAC73232.1 |
| spermidine acetyltransferase (SpeG) | speG | AAC74656.1 |
| glutamate-putrescine/glutamate-cadaverine ligase (PuuA) | puuA | AAC74379.2 |
| putrescine importer (PuuP) | puuP | AAC74378.2 |
| putrescine/cadaverine aminotransferase (YgjG) | ygjG | AAC76108.3 |

In certain embodiments, the fourth polypeptide comprises, consists of, or consists essentially of a lysine biosynthesis polypeptide, a fragment thereof or a mutant thereof. In certain embodiments, the fourth polypeptide may be selected from the group consisting of SucA, Ppc, AspC, LysC, Asd, DapA, DapB, DapD, ArgD, DapE, DapF, LysA, Ddh, PntAB, CyoABE, GadAB, YbjE, GdhA, GltA, SucC, GadC, AcnB, PflB, ThrA, AceA, AceB, GltB, AceE, SdhA, MurE, SpeE, SpeG, PuuA, PuuP, and YgjG, fragments thereof, and mutants thereof. For example, without limitation, the fourth polypeptide may be any one of the proteins listed in Table 2. In certain embodiments, the fourth polypeptide may contain one or more mutations. For example, the fourth polypeptide may comprise the sequence of the E. coli aspartokinase III (LysC or AKIII) polypeptide with a mutation from a methionine to an isoleucine at position 318 and a mutation from a glycine to an aspartic acid at position 323 (LysC-1 (M318I, G323D)) having the sequence of SEQ ID NO: 26. In certain embodiments, the fourth polypeptide may comprise the sequence of the *E. coli* LysC polypeptide with a mutation from a threonine to a methionine at position 344 and a mutation from a threonine to an isoleucine at position 352 (LysC-1 (T344M, T352I)) having the sequence of SEQ ID NO: 27.

In certain embodiments, the fourth polypeptide may comprise the sequence of a protein involved in lysine biosynthesis that is homologous to any one of the proteins listed in Table 2. In certain embodiments, the fourth polynucleotide may comprise the sequence of a protein involved in lysine biosynthesis that is from a species other than *E. coli*. For example, the fourth polypeptide may comprise the sequence of the aspartokinase protein, LysC, from *Streptomyces lividans* (GenBank EOY48571.1) having the sequence of SEQ ID NO: 28). As used herein, a polypeptide that is homologous to an *E. coli* protein has a polypeptide sequence with at least about 90%, at least about 95%, at least about 97%, at least about 98%, or at least about 99% sequence homology with the polypeptide sequence of the *E. coli* protein.

In certain embodiments, the protein involved in lysine biosynthesis is one or more of aspartate kinase (LysC), dihydrodipicolinate synthase (DapA), diaminopimelate decarboxylase (LysA), a fragment, and/or mutant thereof. In certain embodiments, the protein involved in lysine biosynthesis is from the genera *Escherichia*. In certain embodiments, the protein involved in lysine biosynthesis is from the species *E. coli*. For example, the protein may be *E. coli* aspartate kinase (LysC or AKIII) protein (SEQ ID NO: 3), which is encoded by the polynucleotide sequence of the lysC gene. In some embodiments, the protein may be *E. coli* dihydrodipicolinate synthase (DapA or DHDPS) protein (SEQ ID NO: 4), which is encoded by the polynucleotide sequence of the dapA gene. In certain embodiments, the protein may be *E. coli* diaminopimelate decarboxylase (LysA) protein (SEQ ID NO: 5), which is encoded by the polynucleotide sequence of the lysA gene. In certain embodiments, the protein involved in lysine biosynthesis is one or more proteins listed in Table 2, fragments thereof and/or mutants thereof.

In certain embodiments, the first expression plasmid vector may be used for the production of a lysine derived product as described herein. In certain embodiments, a lysine derived product may be cadaverine as described herein.

In certain embodiments, the second, third and/or fourth polynucleotide may be a recombinant or non-naturally occurring polynucleotide. In certain embodiments, the second polynucleotide may be cDNA. In certain embodiments, the second, third and/or fourth polynucleotide may be obtained by codon optimization for optimal polypeptide expression in a particular microorganism (e.g., *E. coli, H. alvei*, or *P. aeruginosa*).

Another aspect of the invention relates to a transformant comprising one or more first expression plasmid vectors that are the same or different, and disclosed herein in a host cell.

The first expression plasmid vectors; host cell; backbone plasmid; and further additions to the first expression plasmid vector are the same as described supra.

As used herein, a transformant is a host cell that has been altered by introducing one or more expression plasmid vectors in the host cell, wherein the one or more expression plasmid vectors are the same or different. In certain embodiments, the transformant is obtained by introducing an expression plasmid vector through transformation into a host cell displaying competence to the plasmid vector.

In certain embodiments, the transformant may be used for the production of lysine or a lysine derived product as described herein. In certain embodiments, a lysine derived product may be cadaverine as described herein.

Another aspect of the invention relates to a transformant comprising one or more first expression plasmid vectors that are the same or different and disclosed herein in a host cell, the transformant further comprising, consisting, or consisting essentially of:

one or more second expression plasmid vectors that are the same or different, and each comprises, consists, or consists essentially of:
  one or more fifth polynucleotides that are the same or different and independently selected from the group consisting of a first polynucleotide encoding a first polypeptide comprising, consisting, or consisting essentially of a tetracycline efflux pump polypeptide, a fragment thereof or a mutant thereof, a third polynucleotide encoding a third polypeptide comprising, consisting, or consisting essentially of a lysine decarboxylase polypeptide, a fragment thereof or a mutant thereof, and a fourth polynucleotide encoding a fourth polypeptide comprising, consisting, or consisting essentially of a lysine biosynthesis polypeptide, a fragment thereof or a mutant thereof; and a backbone plasmid capable of autonomous replication in a host cell, wherein the one or more first and second expression plasmid vectors are used for production of lysine or a lysine-derived product.

The first expression plasmid vectors; first polynucleotides, fragments and mutants thereof; first polypeptides, fragments and mutants thereof; tetracycline efflux pump polypeptides, fragments and mutants thereof; third polynucleotides, fragments and mutants thereof; third polypeptides, fragments and mutants thereof; lysine decarboxylase polypeptides, fragments and mutants thereof; fourth polynucleotides, fragments and mutants thereof; fourth polypeptides, fragments and mutants thereof; lysine biosynthesis polypeptides, fragments and mutants thereof; host cell; backbone plasmid; and further additions to the first expression plasmid vector are the same as described supra.

In certain embodiments, the second expression plasmid vector further comprises one or more sixth polynucleotides that are the same or different and each encodes a sixth polypeptide comprising, consisting of, or consisting essentially of an antibiotic resistance protein, a fragment thereof, or a mutant thereof. In certain embodiments, the antibiotic resistance protein may be a tetracycline resistance protein or an oxytetracycline-resistance protein. In certain embodiments, the antibiotic resistance protein may be selected from the group that comprises, consists of, or consists essentially of OtrA, OtrB, OtrC, Tcr3, a fragment, and/or mutant thereof. In certain embodiments, OtrA may be from the genus *Mycobacterium* or *Streptomyces*. In certain embodiments, OtrB, OtrC, and Tcr3 may be from the genus *Streptomyces*. In certain embodiments, the sixth polynucleotide may be selected from the group that comprises, consists of, or consists essentially of otrA, otrB, otrC, tcr3, a fragment, or mutant thereof. In certain embodiments, otrA may be from the genus *Mycobacterium* or *Streptomyces*. In certain embodiments, otrB, otrC, and tcr3 may be from the genus *Streptomyces*.

In certain embodiments, the transformant may be used for the production of lysine or a lysine derived product as described herein. In certain embodiments, a lysine derived product may be cadaverine as described herein.

Another aspect of the invention relates to a mutant host cell comprising, consisting of, or consisting essentially of:
one or more first polynucleotides that are the same or different, and integrated into a chromosome of a host cell, wherein each of the one or more first polynucleotides encodes one or more first polypeptides that are the same or different and each comprises, consists of, or consists essentially of a tetracycline efflux pump polypeptide, a fragment thereof, or a mutant thereof.

The first polynucleotides, fragments and mutants thereof; first polypeptides, fragments and mutants thereof; tetracycline efflux pump polypeptides, fragments and mutants thereof; and host cell are the same as described supra.

In certain embodiments, the mutant host cell may be used for the production of lysine or a lysine derived product as described herein. In certain embodiments, a lysine derived product may be cadaverine as described herein.

In certain embodiments, the first polynucleotide may be integrated into the host cell chromosome according to the PCR-mediated gene replacement method (see, e.g. Datsenko, 2000 for an overview of the PCR-mediated gene replacement method, which is incorporated herein by reference in its entirety). Integrated chromosomes may also be produced by other suitable methods.

Another aspect of the invention relates to a mutant host cell comprising, consisting of, or consisting essentially of:
one or more first polynucleotides integrated into a chromosome of a host cell, wherein the one or more first polynucleotides are the same or different, and each of the one or more first polynucleotides encodes one or more first polypeptides that are the same or different and each comprises, consists of, or consists essentially of a tetracycline efflux pump polypeptide, a fragment thereof, or a mutants thereof;
one or more second polynucleotides integrated into a chromosome of the host cell, wherein the one or more second polynucleotide are the same or different and independently selected from the group consisting of:
a third polynucleotide encoding a third polypeptide comprising, consisting of, or consisting essentially of a lysine decarboxylase polypeptide, a fragment thereof or a mutant thereof, and
a fourth polynucleotide encoding a fourth polypeptide comprising, consisting of, or consisting essentially of a lysine biosynthesis polypeptide, a fragment thereof or a mutant thereof.

The first polynucleotides; first polypeptides; tetracycline efflux pump polypeptides, fragments and mutants thereof; second polynucleotides; third polynucleotides; third polypeptides; lysine decarboxylase polypeptides, fragments and mutants thereof; fourth polynucleotides; fourth polypeptides; lysine biosynthesis polypeptides, fragments and mutants thereof; and host cell are the same as described supra.

In certain embodiments, when there are a plurality of the first polypeptides, each first polypeptide may be the same or different and may be expressed individually or as a fusion protein.

In certain embodiments, when there are a plurality of the second polynucleotides, each third polypeptide may be the same or different, and each fourth polypeptide may be the same or different; the third and fourth polypeptides may be expressed individually or as a fusion protein.

In certain embodiments, the first and second polynucleotides may be integrated into the host cell chromosome according to the PCR-mediated gene replacement method (see, e.g. Datsenko, 2000 for an overview of the PCR-mediated gene replacement method, which is incorporated herein by reference in its entirety). Integrated chromosomes may also be produced by other suitable methods.

In certain embodiments, the mutant host cell may be used for the production of lysine or a lysine derived product as described herein. In certain embodiments, a lysine derived product may be cadaverine as described herein.

Another aspect of the invention relates to a method for producing lysine comprising:
obtaining a transformant and/or mutant host cell as disclosed herein;
culturing the transformant and/or mutant host cell under conditions effective for the expression of the lysine; and
harvesting the lysine.

In certain embodiments, the transformant and/or mutant host cell may be any of those as described herein. For example, the transformant used to produce lysine may be obtained by transforming one or more expression plasmid vectors that are the same or different, and disclosed herein into a host cell.

The transformant and/or mutant host cell may be cultured using a medium containing carbon sources and non-carbon nutrient sources. Examples of carbon sources include, without limitation, sugar (e.g. carbohydrates such as glucose and fructose), oil and/or fat, fatty acid, and/or derivatives thereof. The oil and fat may contain saturated and/or unsaturated fatty acids having 10 or more carbon atoms, e.g. coconut oil, palm oil, palm kernel oil, and the like. The fatty acid may be a saturated and/or unsaturated fatty acid, e.g. hexanoic acid, octanoic acid, decanoic acid, lauric acid, oleic acid, palmitic acid, linoleic acid, linolenic acid, myristic acid, and the like. Examples of derivatives of a fatty acid include, without limitation, esters and salts thereof. Examples of non-carbon sources include, without limitation, nitrogen sources, inorganic salts, and other organic nutrient sources.

For example, a medium may contain a carbon source assimilable by the transformant and/or mutant host cell, optionally with one or more other sources independently selected from the group consisting of a nitrogen source, an inorganic salt and another organic nutrient source. In certain embodiments, the weight percentage of the nitrogen source is about 0.01 to about 0.1% of the medium. Examples of the nitrogen source may comprise ammonia, ammonium salts (e.g. ammonium chloride, ammonium sulfate and ammonium phosphate), peptone, meat extract, yeast extract, and the like. Examples of the inorganic salts include, without limitation, potassium dihydrogen phosphate, dipotassium hydrogen phosphate, magnesium phosphate, magnesium sulfate, sodium chloride, and the like. Examples of the other organic nutrient source include, without limitation, amino acids (e.g. glycine, alanine, serine, threonine and proline), vitamins (e.g. vitamin B1, vitamin B12 and vitamin C), and the like.

The culture may be carried out at any temperature as long as the cells can grow, and preferably at about 20° C. to about 40° C., or about 35° C. The culture period may be about 1, about 2, about 3, about 4, about 5, about 6, about 7, about 8, about 9, or about 10 days.

In one embodiment, the transformant and/or mutant host cell is cultured in a medium containing peptides, peptones, vitamins (e.g. B vitamins), trace elements (e.g. nitrogen, sulfur, magnesium), and minerals. Examples of such medium include, without limitation, commonly known Lysogeny broth (LB) mediums comprising tryptone, yeast extract and NaCl suspended in water (e.g. distilled or deionized).

Another aspect of the invention relates to a method for producing cadaverine (1,5-pentanediamine) comprising, consisting of, or consisting essentially of:
1a) cultivating the transformant and/or mutant host cell as disclosed herein,
1b) producing cadaverine using the culture obtained from step 1a to decarboxylate lysine, and
1c) extracting and purifying cadaverine using the culture obtained from step 1b.

In certain embodiments, the transformant and/or mutant host cell may be any of those as described herein.

Cultivating the transformant may comprise the steps of culturing the transformant as described supra.

As used herein, "using the culture obtained from step 1a" may comprise further processes of the culture obtained from step 1a. For example, using a buffer solution to dilute the culture; centrifuging the culture to collect the cells; resuspending the cells in a buffer solution; or lysing the cells into cell lysate; or/and purifying lysine decarboxylase from the cell lysate.

In another embodiment, step 1c of the method further comprises the following steps:
1d) separating the solid and liquid components of the reaction obtained from step 1b;
1e) adjusting the pH of the liquid component obtained from step 1d to about 14 or higher;
1f) removing water from the liquid component obtained from step 1e; and
1g) recovering cadaverine.

In step 1d, the separation of solid and liquid components of the reaction of step 1b may be accomplished by conventional centrifugation and/or filtration.

In step 1e, the pH of the liquid component of step 1d may be adjusted by adding a base, e.g. NaOH. NaOH may be added as a solid and/or a solution (e.g. an aqueous solution).

In step 1f, the water may be removed by distillation at ambient pressure or under vacuum.

In step 1g, cadaverine may be recovered by distillation at ambient pressure or under vacuum.

Another aspect of the invention relates to biobased cadaverine prepared according to the method disclosed herein.

As used herein, a "biobased" compound means the compound is considered biobased under Standard ASTM D6866.

Another aspect of the invention relates to a polyamide having a structure of Structure 1:

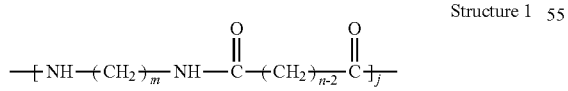

Structure 1 including stereoisomers thereof, wherein:
m=4, 5, 6, 7, 8, 9, 10, 11, 12, 13, 14, 15, 16, 17, 18, 19, 20, 21, or 22;
n=4, 5, 6, 7, 8, 9, 10, 11, 12, 13, 14, 15, 16, 17, 18, 19, 20, 21, or 22;
j=about 100~about 1,000,000; and
the polyamide is prepared from one or more diamines having carbon numbers of m and one or more dicarboxylic acids having carbon numbers of n, at least one of the diamines and dicarboxylic acids comprises biobased carbon under Standard ASTM D6866, and the m or n of each diamine or dicarboxylic acid can be the same or different.

In one embodiment, the diamine is biobased cadaverine, more preferably biobased cadaverine prepared according to the method disclosed herein. Examples of the dicarboxylic acids include, without limitation, $C_{10}$dicarboxylic acid, $C_{1}$dicarboxylic acid, $C_{12}$dicarboxylic acid, $C_{13}$dicarboxylic acid, $C_{14}$dicarboxylic acid, $C_{16}$dicarboxylic acid, $C_{18}$dicarboxylic acid, and any combinations thereof. In certain embodiments, all or part of the $C_n$dicarboxylic acids are biobased.

In another embodiments, the polyamide has a structure described above, wherein:
the polyamide is formed by reacting biobased cadaverine with one or more dicarboxylic acids, more preferably the biobased cadaverine is prepared according to the method disclosed herein;
n=4, 5, 6, 7, 8, 9, 10, 11, 12, 13, 14, 15, 16, 17, 18, 19, 20, 21, or 22;
j=about 100~about 1,000,000, about 1000~about 100, 000, or about 1000~about 10,000; and
the dicarboxylic acids comprise biobased carbon under Standard ASTM D6866.

Another aspect of the invention relates to a method of making the polyamides disclosed herein comprising preparing biobased cadaverine as the Cmdiamine according to the method disclosed herein.

In one embodiment, the method further comprises preparing one or more biobased Cndicarboxylic acids.

In another embodiment, the method further comprises preparing the polyamide by reacting biobased cadaverine with one or more biobased Cndicarboxylic acids.

Another aspect of the invention relates to a composition comprising one or more polyamides disclosed herein.

In one embodiment, the diamine is biobased cadaverine, more preferably biobased cadaverine prepared according to the method disclosed herein. Examples of the dicarboxylic acids include, without limitation, C10dicarboxylic acid, C11dicarboxylic acid, C12dicarboxylic acid, C13dicarboxylic acid, C14dicarboxylic acid, C16dicarboxylic acid, C18dicarboxylic acid, and any combinations thereof. In certain embodiments, all or part of the Cndicarboxylic acids are biobased.

In another embodiment, the polyamide has a structure described above, wherein:
the polyamide is formed by reacting biobased cadaverine with one or more dicarboxylic acids, more preferably the biobased cadaverine is prepared according to the method disclosed herein;
n=4, 5, 6, 7, 8, 9, 10, 11, 12, 13, 14, 15, 16, 17, 18, 19, 20, 21, or 22;
j=about 100~about 1,000,000, about 1000~about 100, 000, or about 1000~about 10,000; and
the dicarboxylic acids comprise biobased carbon under Standard ASTM D6866.

Another aspect of the invention relates to a method of preparing 1,5-diisocyanatopentane comprising:
2a) preparing biobased cadaverine as disclosed herein; and
2b) converting biobased cadaverine obtained from step 2a to 1,5-diisocyanatopentane.

Step 2b may comprise using any known method to convert diamine into isocyanate. An example of said method is the traditional phosgene method, which includes one-step high temperature phosgene method (i.e. mixing phosgene with diamine at high temperature to obtain isocyanate), the improved two-step phosgene method, and the triphosgene method in which triphosgene is used instead of phosgene. There are also other methods that do not use phosgene as a raw material. An example of said method is hexanediamine carbonylation which uses CO2 instead of phosgene: CO2 is added into a solution of a primary amine and an organic base, then a proper amount of phosphorus electrophilic reagents is added into the reaction solution to start an exothermic dehydration reaction to obtain isocyanate. Another example is carbamate thermal decomposition method wherein a primary amine is converted to a carbamate, and then the carbamate is heated to decompose and generate isocyanate.

The abbreviations used for the amino acids, polypeptides, base sequences, and nucleic acids are based on the abbreviations specified in the IUPAC-IUB Communication on Biochemical Nomenclature, Eur. J. Biochem., 138:9 (1984), "Guideline for Preparing Specifications Including Base Sequences and Amino Acid Sequences" (United States Patent and Trademark Office), and those commonly used in this technical field.

Unless the context clearly requires otherwise, throughout the description and the claims, the words "comprise," "comprising," and the like are to be construed in an inclusive sense (i.e., to say, in the sense of "including, but not limited to"), as opposed to an exclusive or exhaustive sense. The words "herein," "above," "below," "supra," and words of similar import; when used in this application, refer to this application as a whole and not to any particular portions of this application. Where the context permits, words in the above Detailed Description using the singular or plural number may also include the plural or singular number respectively. The words "or," and "and/or" in reference to a list of two or more items, covers all of the following interpretations of the word: any of the items in the list, all of the items in the list, and any combination of the items in the list.

In *E. coli*, lysine is known to be transported across the membrane into the cell through three pathways: one mediated by the lysine-specific permease LysP, another mediated by the ArgT ABC transporter that also recognizes arginine and ornithine, and the third is mediated by the lysine/cadaverine antiporter, CadB. Bacteria use pumps to transport antibiotics out of the cell and nutrients into a cell. Tetracyclines are antibiotics that stop protein synthesis and inhibit cell growth. Many Gram-positive and Gram-negative bacteria have evolved to express proteins that pump tetracycline out of the cell. To date, sixty-one tetracycline resistance genes have been sequenced in bacteria that produce or do not produce tetracyclines. The most commonly used tetracycline efflux pump in the laboratory is TetA, a protein that localizes to the inner membrane and catalyzes the exchange of monocationic magnesium-tetracycline chelate complex from inside the cell with a proton from outside the cell.

A mechanism that enables *E. coli* transport of lysine and lysine-derived products across the membrane is disclosed herein. As shown in the Examples below, the increased expression of tetracycline efflux pump protein, TetA, resulted in an increased production of lysine in *E. coli*. Additionally, the increased expression of TetA in both *E. coli* and *H. alvei* resulted in a higher yield of cadaverine, a metabolite derived from lysine. Therefore, the data provided herein indicate that tetracycline efflux pumps can be used to increase the yield of lysine and/or lysine derived products.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

Construction of Strains Containing Plasmid Vectors That Encode a Tetracycline Efflux Pump The *E. coli* gene, tetA (SEQ ID NO: 1), that encodes a tetracycline efflux pump, TetA (SEQ ID NO: 2), was amplified from the *E. coli* cloning vector pBR322 using the PCR primers tetA-F and tetA-R (FIG. 1). The amplified DNA was digested with the restriction enzymes SacI and XbaI, and ligated into a pUC18 plasmid vector and a pCIB10 plasmid vector to create pCIB17 and pCIB20, respectively (FIG. 2). pCIB17 was transformed into *E. coli* and *H. alvei* to create strains CIB17-EC and CIB17-HA, respectively (FIG. 2).

Example 2

Construction of Strains Containing Plasmid Vectors That Encode Either Wild-Type CadA or an Inactive CadA Mutant A plasmid vector containing wild-type *E. coli* cadA, which encodes the lysine decarboxylase CadA (SEQ ID NO: 6), was constructed by cloning wild-type cadA into pUC18 to generate the positive control, pCIB60 (FIG. 2). A plasmid vector containing an inactive mutant cadA was constructed by truncating the C-terminus of cadA by introducing a premature stop codon which resulted in a mutation at amino acid 566 of CadA and a truncated CadA protein (CadA (aa1-565) (where "aa" is amino acids) (SEQ ID NO: 33). The primers cadAm1-F and cadAm1-R (FIG. 1) were used to amplify a fragment of cadA. The amplified mutant cadA and the pCIB60 plasmid were digested using the restriction enzymes XhoI and SphI. The digested mutant cadA was then ligated into the digested pCIB60 plasmid vector to replace the wild type cadA with the mutant cadA. The plasmid vector expressing the truncated cadA gene was designated as pCIB63 (FIG. 2). pCIB60 was transformed into *E. coli* and *H. alvei* to create the strains CIB60-EC and CIB60-HA, respectively. pCIB63 was transformed into *E. coli* and *H. alvei* to create the strains CIB63-EC and CIB63-HA, respectively (FIG. 2).

Example 3

Production of Cadaverine from *E. coli* and *H. alvei* Strains Expressing a Recombinant Tetracycline Efflux Pump A single colony of each strain was grown overnight in LB medium with ampicillin (100 µg/mL) in a 2.5 mL culture at 29° C. *E. coli* and *H. alvei* transformed with the empty vector, pUC18, were used as negative controls. The following day, 2.5 mL of minimal media was supplemented with ampicillin (100 µg/mL), and lysine-HCl and PLP to a final concentration of 20 g/L and 0.1 mM, respectively. Each culture was incubated at 37° C. for 5 hours and 21 hours. 1 mL of sample was taken from each culture at the 5- and 21-hour time points to quantify cadaverine production using nuclear magnetic resonance (NMR). Cadaverine production at both time points from strains expressing the mutant, CadA (aa1-565), wild-type CadA or TetA is presented in Table 3.

TABLE 3

Production of cadaverine in *E. coli* and *H. alvei* by expression of CadA or TetA.

| Host | Strain | Enzyme(s) | Gene(s) | 5 hrs (g/kg) | 21 hrs (g/kg) |
|---|---|---|---|---|---|
| *E. coli* | | none | none | 0.20 | N.A. |
| | CIB63-EC | CadA (aa1-565) | mutant cadA | 2.99 ± 0.005 | 3.78 ± 0.04 |
| | CIB60-EC | CadA | cadA | 8.93 ± 0.9 | 11.7 ± 0.02 |
| | CIB17-EC | TetA | tetA | 5.14 ± 0.1 | 11.1 ± 0.5 |
| *H. alvei* | | none | none | 1.27 | N.A. |
| | CIB63-HA | CadA (aa1-565) | mutant cadA | 0.24 | N.A. |
| | CIB60-HA | CadA | cadA | 9.64 ± 0.3 | N.A. |
| | CIB17-HA | TetA | tetA | 9.28 ± 1.8 | N.A. |

N.A.: data not available

As indicated in Table 3, expression of TetA in *E. coli* resulted in a higher yield of cadaverine production as compared to the negative control (no enzyme) and the mutant CadA (aa1-565) (5 hours: 5.14 g/kg compared to 0.20 g/kg and 2.99 g/kg, respectively; 21 hours: 11.1 g/kg compared to N.A. and 3.78 g/kg). Also, expression of TetA in *H. alvei* resulted in a higher yield of cadaverine production as compared to the negative control (none) and the mutant CadA (aa1-565) (5 hours: 9.28 g/kg compared to 1.27 g/kg and 0.24 g/kg, respectively).

Example 4

Production of Cadaverine from *E. coli* Strains Co-Expressing a Recombinant Lysine Decarboxylase and a Recombinant Tetracycline Efflux Pump The tetA gene was cloned into the pCIB60 plasmid vector behind the cadA gene. First, tetA was amplified from pBR322 using primers tetA-F2 and tetA-R2 (FIG. 1). Next, the amplified PCR product and pCIB60 plasmid vector were digested using the restriction enzymes XbaI and HindIII, and the products were ligated together to create pCIB77. pCIB77 was transformed into *E. coli* MG1655 K12 to create the strain CIB77 (FIG. 2).

A single colony of each strain was grown overnight in LB medium with ampicillin (100 µg/mL) in a 2.5 mL culture at 29° C. The following day, minimal media was supplemented with ampicillin (100 µg/mL), and lysine-HCl and PLP to a final concentration of 20 g/L and 0.1 mM, respectively. Each culture was incubated at 37° C. for 3 hours and 6 hours. 1 mL of sample was taken from each culture at the 3- and 6-hour time points to quantify cadaverine production using NMR. Cadaverine production at both time points from strains expressing CadA or TetA and CadA is presented in Table 4.

TABLE 4

Production of cadaverine in *E. coli* by expression of CadA or CadA and TetA.

| Host | Strain | Enzyme(s) | Gene(s) | 3 hrs (g/kg) | 6 hrs (g/kg) |
|---|---|---|---|---|---|
| *E. coli* | | None | None | 0.14 | 0.31 |
| | CIB60 | CadA | cadA | 4.38 ± 0.65 | 6.20 ± 0.61 |
| | CIB77 | TetA, CadA | tetA, cadA | 5.54 ± 1.30 | 8.06 ± 0.65 |

Table 4 indicates that expression of TetA and CadA together resulted in a higher yield of cadaverine production in *E. coli* when compared to expression of only CadA (3 hours: 5.54 g/kg compared to 4.38 g/kg, respectively; 6 hours: 8.06 g/kg compared to 6.20 g/kg, respectively).

Example 5

Production of Lysine From Strains Co-Expressing a Recombinant Tetracycline Efflux Pump and Recombinant Proteins (LysC, DapA, LysA) From the Lysine Biosynthetic Pathway Three genes from *E. coli*, lysC, dapA, and lysA, encode proteins involved in the *E. coli* lysine biosynthetic pathway: aspartate kinase (LysC or AKIII, encoded by lysC), dihydrodipicolinate synthase (DapA or DHDPS, encoded by dapA), and diaminopimelate decarboxylase (LysA, encoded by lysA). The three genes were cloned into a plasmid vector and the three proteins, LysC (SEQ ID NO: 3), DapA (SEQ ID NO: 4), and LysA (SEQ ID NO: 5) were overexpressed in *E. coli*. The gene lysC was amplified from the *E. coli* MG1655 K12 genomic DNA using the primers lysC-F and lysC-R (FIG. 1), and the amplified fragment was digested using SacI and BamHI, and ligated into pUC18 to create pCIB7 (FIG. 2). The gene dapA was amplified from the *E. coli* MG1655 K12 genomic DNA using the primers dapA-F and dapA-R (FIG. 1), and the amplified fragment was digested using BamHI and XbaI, and ligated into pCIB7 to create pCIB8 (FIG. 2). The gene lysA was amplified from the *E. coli* MG1655 K12 genomic DNA using the primers lysA-F and lysA-R (FIG. 1), and the amplified fragment was digested using XbaI and SalI, and ligated into pCIB8 to create pCIB9. The three-gene operon was amplified from pCIB9 using the primers lysC-F and lysA-R (FIG. 1). The amplified product was digested using SacI and SalI, and the digested fragment was ligated into pCIB10 to create pCIB32 (FIG. 2). pCIB32 was transformed into *E. coli* to create the strain CIB32. CIB32 was further transformed with pCIB20, the plasmid containing the tetA gene.

A single colony was grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, ampicillin (100 µg/mL), and tetracycline (10 µg/mL). The following day, each culture was inoculated into 100 mL of fresh medium with ampicillin (100 µg/mL) and tetracycline (10 µg/mL), and grown for 21 hours at 37° C., at which point the concentration of lysine in each culture was determined (Table 5).

TABLE 5

Production of lysine in *E. coli* by expression of TetA and proteins from the lysine biosynthetic pathway.

| Host | Strain and Plasmid | Enzyme(s) | Gene(s) | Lysine (mg/g) |
|---|---|---|---|---|
| *E. coli* | MG1655 K12 | none | none | n.d. |
| | CIB32 | LysC, DapA, LysA | lysC, dapA, lysA | 1.47 ± 0.05 |
| | CIB32 + pCIB20 | LysC, DapA, LysA, TetA | lysC, dapA, lysA, tetA | 2.46 ± 0.03 | n.d.: none detected

As indicated in Table 5, the expression of TetA along with proteins involved in the lysine biosynthetic pathway (i.e., CIB32+pCIB20) resulted in a higher yield of lysine as compared to expression of proteins involved in the lysine biosynthetic pathway without TetA (i.e., CIB32) (compare 2.46 mg/g to 1.47 mg/g).

Example 6

Production of Lysine From Strains Co-Expressing a Recombinant Tetracycline Efflux Pump and Recombinant Proteins (LysC, DapA, LysA, DapB, DapD, AspC, Asd) From the Lysine Biosynthetic Pathway Next, the expression of four additional genes, asd, dapB, dapD, and aspC, which are involved in the lysine biosynthetic pathway of *E. coli*, was enhanced. These genes encode the following enzymes: aspartate semialdehyde dehydrogenase (Asd (SEQ ID NO: 22), encoded by asd), dihydrodipicolinate reductase (DapB or DHDPR (SEQ ID NO: 23), encoded by dapB), tetrahydrodipicolinate succinylase (DapD (SEQ ID NO: 24), encoded by dapD), and aspartate transaminase (AspC (SEQ ID NO: 25), encoded by aspC). The gene asd was amplified from the *E. coli* MG1655 K12 genomic DNA using the primers asd-F and asd-R (FIG. 1), and the amplified fragment was digested using SacI and BamHI, and ligated into pUC18 to create pCIB12 (FIG. 2). The gene dapB was amplified from the *E. coli* MG1655 K12 genomic DNA using the primers dapB-F and dapB-R (FIG. 1), and the amplified fragment was digested using BamHI and XbaI, and ligated into pCIB12 to create pCIB13 (FIG. 2). The gene dapD was amplified from the *E. coli* MG1655 K12 genomic DNA using the primers dapD-F and dapD-R (FIG. 1), and the amplified fragment was digested using XbaI and SalI, and ligated into pCIB13 to create pCIB14 (FIG. 2). Similarly, the gene aspC was amplified from the *E. coli* MG1655 K12 genomic DNA using the primers aspC-F and aspC-R (FIG. 1), and the amplified fragment was digested using XbaI and SalI, and ligated into pCIB13 to create pCIB31 (FIG. 2). The gene tetA was amplified from pCIB20 using the primers tetA-F3 and tetA-R3 (FIG. 1), and the amplified fragment was digested using XhoI and SphI and ligated into pCIB14 and pCIB31 to generate plasmids pCIB15 and pCIB59, respectively (FIG. 2). pCIB59 and pCIB15 were each transformed into strain CIB32.

A single colony was grown overnight at 37° C. in 3mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, ampicillin (100 μg/mL), and tetracycline (10 μg/mL). The following day, each culture was inoculated into 100 mL of fresh medium with ampicillin (100 μg/mL) and tetracycline (10 μg/mL), and grown for 21 hours at 37° C., at which point the concentration of lysine in each culture was determined (Table 6).

TABLE 6

Production of lysine in *E. coli* by expression of TetA and proteins from the lysine biosynthetic pathway.

| Host | Strain and Plasmid | Enzyme(s) | Gene(s) | Lysine (mg/g) |
|---|---|---|---|---|
| *E. coli* | MG1655 K12 | none | none | n.d. |
| | CIB32 | LysC, DapA, LysA | lysC, dapA, lysA | 0.61 ± 0.02 |
| | CIB32 + pCIB20 | LysC, DapA, LysA, TetA | lysC, dapA, lysA, tetA | 1.03 ± 0.01 |
| | CIB32 + pCIB15 | LysC, DapA, LysA, Asd, DapB, DapD, TetA | lysC, dapA, lysA, asd, dapB, dapD, tetA | 1.16 ± 0.03 |
| | CIB32 + pCIB59 | LysC, DapA, LysA, Asd, DapB, AspC, TetA | lysC, dapA, lysA, asd, dapB, aspC, tetA | 1.14 ± 0.02 | n.d.: none detected

As indicated in Table 6, the expression of TetA along with proteins involved in the lysine biosynthetic pathway (i.e., CIB32+pCIB20, CIB32 +pCIB15, and CIB32+pCIB59) resulted in a higher yield of lysine as compared to expression of proteins involved in the lysine biosynthetic pathway without TetA (i.e., CIB32) (compare 1.03 mg/g, 1.16 mg/g, and 1.14 mg/g to 0.61 mg/g).

Example 7

Production of Lysine From Strains Co-Expressing a Recombinant Tetracycline Efflux Pump and Various Aspartokinases Various aspartokinases were expressed in order to increase lysine production. Two pairs of mutations were chosen that enabled the *E. coli* aspartokinase III (LysC or AKIII, encoded by lysC, SEQ ID NO: 3) to have an increased feedback resistance to lysine. The gene encoding the first mutant, LysC-1 (M318I, G323D) (SEQ. ID NO: 26) was constructed using the primers 318-F, 318-R, 323-F, 323-R (FIG. 1). The gene encoding the second mutant, LysC-2 (T344M, T352I) (SEQ. ID NO: 27), was constructed using the primers 344-F, 344-R, 352-F, 352-R (FIG. 1). The genes encoding LysC-1(M318I, G323D) and LysC-2 (T344M, T352I) were cloned into pCIB32 and replaced the wild-type *E. coli* aspartokinase, LysC, to create the plasmids pCIB43 and pCIB44, respectively (FIG. 2). The aspartokinase from *Streptomyces* strains that is capable of producing polylysine was previously suggested, but not proven, to be more feedback resistant to lysine compared to *E. coli* aspartokinase. As such, the aspartokinase gene from *Streptomyces lividans* was codon optimized, synthesized, and cloned in place of wild-type lysC in pCIB32 in order to create the plasmid pCIB55 using the primers SlysC-F and SlysC-R (FIG. 1). The resulting aspartokinase protein that was expressed was named S-LysC (SEQ ID NO: 28). pCIB43, pCIB44, and pCIB55 were transformed into *E. coli* MG1655 to create the strains CIB43, CIB44, and CIB55, respectively (FIG. 2). pCIB59 was also transformed into CIB55.

A single colony was grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, ampicillin (100 µg/mL), and tetracycline (10 µg/mL). The following day, each culture was inoculated into 100 mL of fresh medium with ampicillin (and tetracycline in the case of CIB55+pCIB59), and grown for 63 hours, at which point the concentration of lysine in each culture was determined.

TABLE 7

Production of lysine in E. coli by expression of TetA and proteins from the lysine biosynthetic pathway.

| Host | Strain and Plasmid | Enzyme(s) | Gene(s) | Lysine (mg/g) |
|---|---|---|---|---|
| E. coli | MG1655 K12 | none | none | n.d. |
| | CIB32 | LysC, DapA, LysA | lysC, dapA, lysA | 0.48 ± 0.01 |
| | CIB43 | LysC-1 (M318I, G323D), DapA, LysA | lysC-1, dapA, lysA | 1.57 ± 0.02 |
| | CIB44 | LysC-2 (T344M, T352I), DapA, LysA | lysC-2, dapA, lysA | 1.50 ± 0.02 |
| | CIB55 | S-LysC, DapA, LysA | S-lysC, dapA, lysA | 1.55 ± 0.02 |
| | CIB55 + pCIB59 | S-LysC, DapA, LysA, Asd, DapB, AspC, TetA | S-lysC, dapA, lysA, asd, dapB, aspC, tetA | 1.66 ± 0.01 | n.d. = not detected

Example 8

Production of Lysine in E. coli

The two lysine operons consisting of the genes S-lysC, dapA, lysA, asd, dapB, and aspC were combined into a single vector. The operon from pCIB55 consisting of the genes S-lysC, dapA, and lysA was amplified using the primers SAL-F and SAL-R (FIG. 1). The operon from pCIB31 consisting of the genes asd, dapB, and aspC was amplified using the primers ABC-F and ABC-R (FIG. 1). The operon from pCIB59 consisting of the genes asd, dapB, and aspC and the tetA gene was amplified using the primers ABC-F and ABCT-R (FIG. 1). The products were digested using the restriction enzymes ApaI and KpnI. The digested products of pCIB55 and pCIB31were ligated to form pCIB92 and the digested products of pCIB55 and pCIB59 were ligated to form pCIB103 (FIG. 2).

E. coli was used as a host to produce lysine. The plasmids, pUC18, pCIB92, and pCIB103 were independently co-transformed with pCIB110 into E. coli. Two colonies from each transformation were grown overnight at 37° C. in 3 mL of LB medium supplemented with ampicillin (100 mg/L) for 18 hours. The following day, each culture was assayed for cadaverine using NMR. The lysine production is shown in Table 8.

TABLE 8

Production of cadaverine in E. coli by expression of TetA and proteins from the lysine biosynthetic pathway

| Host | Plasmids | Enzyme(s) | Gene(s) | Lysine (mg/g) |
|---|---|---|---|---|
| E. coli | pUC18 | none | none | n.d. |
| | pCIB92 | S-LysC, DapA, | S-LysC, dapA, | 1.62 ± 0.02 |

TABLE 8-continued

Production of cadaverine in E. coli by expression of TetA and proteins from the lysine biosynthetic pathway

| Host | Plasmids | Enzyme(s) | Gene(s) | Lysine (mg/g) |
|---|---|---|---|---|
| | pCIB103 | LysA, Asd, DapB, AspC S-LysC, DapA, LysA, Asd, DapB, AspC, TetA | lysA, asd, dapB, aspC S-lysC, dapA, lysA, asd, dapB, aspC, tetA | 1.70 ± 0.01 | n.d.: none detected

As indicated in Table 8, the expression of TetA along with proteins involved in the lysine biosynthetic pathway (i.e., pCIB103) resulted in a higher yield of cadaverine as compared to expression of proteins involved in the lysine biosynthetic pathway without TetA (i.e., pCIB92) (compare 1.70±0.01 g/kg to 1.62±0.02 g/kg).

Example 9

Production of Cadaverine in H. alvei

H. alvei was used as a host to produce cadaverine without adding any additional lysine to the cell. The plasmids, pUC18, pCIB92, and p103 were independently transformed into H. alvei. Two colonies from each transformation were grown overnight at 37° C. in 3mL of LB medium supplemented with ampicillin (100 mg/L) for 18 hours. The following day, each culture was assayed for cadaverine using NMR. The cadaverine production is shown in Table 8.

TABLE 9

Production of cadaverine in H. alvei by expression of TetA and proteins from the lysine biosynthetic pathway

| Host | Plasmids | Enzyme(s) | Gene(s) | Cadaverine (g/kg) |
|---|---|---|---|---|
| H. alvei | pUC18 | none | none | 0.07 ± 0.04 |
| | pCIB92 | S-LysC, DapA, LysA, Asd, DapB, AspC | S-lysC, dapA, lysA, asd, dapB, aspC | 0.11 ± 0.005 |
| | pCIB103 | S-LysC, DapA, LysA, Asd, DapB, AspC, TetA | S-lysC, dapA, lysA, asd, dapB, aspC, tetA | 0.36 ± 0.01 | n.d.: none detected

As indicated in Table 8, the expression of TetA along with proteins involved in the lysine biosynthetic pathway (i.e., pCIB103) resulted in a higher yield of cadaverine as compared to expression of proteins involved in the lysine biosynthetic pathway without TetA (i.e., pCIB92) (compare 0.36 g/kg to 0.11 g/kg).

Example 10

Increased Cadaverine Production From Mutant TetA

The full-length TetA protein is 396 amino acids long. Amber mutations (stop codons) were introduced into the tetA polynucleotide sequence in order to truncate TetA to determine whether the entire TetA protein is necessary for the increased production of cadaverine. Two truncations of the TetA protein were generated. The first truncation, TetA (aa1-185), was generated by using Splicing by Overlap Extension PCR (SOEing PCR) with the primers tetAm1-F, tetAm1-R, tetA-F2, and tetA-R2 (FIG. 1). This inserted a T after nucleotide 555 in order to create a premature stop codon in the tetA polynucleotide sequence (tetA (nt 1-558), where "nt" is nucleotides, SEQ ID NO: 29), which resulted in a mutation at amino acid 186 and a truncated form of TetA having amino acids 1-185 (SEQ ID NO: 30). The amplified product was cloned into pCIB60 (containing CadA) using the restriction enzymes XbaI and HindIII, and the products were ligated together to create pCIB97 (FIG. 2). The second truncation, TetA (aa1-96), was created using SOEing PCR with the primers tetAm2-F, tetAm2-R, tetA-F2, and tetA-R2 (FIG. 1). This inserted two nucleotides (AA) after nucleotide 289 in order to introduce a premature stop codon in the tetA polynucleotide sequence (tetA (nt 1-291), SEQ ID NO: 31), which resulted in a mutation at amino acid 97 and a truncated form of TetA having amino acids 1-96 (SEQ ID NO: 32). The amplified product was cloned into pCIB60 to create pCIB98. The plasmids pCIB97 and pCIB98 were transformed into E. coli MG1655 to create CIB97 and CIB98, respectively (FIG. 2).

A single colony of each strain was grown overnight in LB medium with ampicillin (100 µg/mL) in a 2 mL culture at 29° C. The following day, 0.9 mL of culture was added to 100 µL of lysine-HCL and 5 µL of PLP to a final concentration of 40 g/L and 0.1 mM, respectively. Each culture was incubated at 37° C. for 2 hours. Each sample was quantified for cadaverine production using NMR (Table 9).

TABLE 9

Production of cadaverine in E. coli by expression of TetA and proteins from the lysine biosynthetic pathway

| Host | Strain | Enzyme(s) | Gene(s) | Cadaverine (g/kg) |
| --- | --- | --- | --- | --- |
| E. coli | MG1655 K12 | none | none | n.d. |
| | CIB60 | CadA | cadA | 1.1 ± 0.1 |
| | CIB77 | TetA, CadA | tetA, cadA | 2.0 ± 1.3 |
| | CIB97 | TetA (1-185), CadA | tetA (nt 1-558), cadA | 1.8 ± 0.1 |
| | CIB98 | TetA (1-96), CadA | tetA (nt 1-291), cadA | 2.6 ± 0.9 | n.d.: none detected

As indicated in Table 9, the expression of TetA with CadA and the truncated forms of TetA with CadA resulted in an increased production of cadaverine compared with expression of CadA alone (compare 2.0 g/kg (CIB77), 1.8 g/kg (CIB97) and 2.6 g/kg (CIB98) compared to 1.1 g/kg (CIB60)). The amount of cadaverine produced with the expression of both TetA mutants (TetA (aa1-185) and TetA (aa1-96)) was comparable to the amount of cadaverine produced with the expression of wild type TetA (2.0 g/kg), with cells expressing TetA (aa1-96) producing the most cadaverine (2.6 g/kg).

SEQUENCE LISTINGS

SEQ ID NO: 1 (Escherichia coli tetA polynucleotide sequence)
ATGAAATCTAACAATGCGCTCATCGTCATCCTCGGCACCGTCACCCT
GGATGCTGTAGGCATAGGCTTGGTTATGCCGGTACTGCCGGGCCTCTTGCGGGAT
ATCGTCCATTCCGACAGCATCGCCAGTCACTATGGCGTGCTGCTAGCGCTATATGC
GTTGATGCAATTTCTATGCGCACCCGTTCTCGGAGCACTGTCCGACCGCTTTGGCC
GCCGCCCAGTCCTGCTCGCTTCGCTACTTGGAGCCACTATCGACTACGCGATCAT
GGCGACCACACCCGTCCTGTGGATCCTCTACGCCGGACGCATCGTGGCCGGCAT
CACCGGCGCCACAGGTGCGGTTGCTGGCGCCTATATCGCCGACATCACCGATGG
GGAAGATCGGGCTCGCCACTTCGGGCTCATGAGCGCTTGTTTCGGCGTGGGTATG
GTGGCAGGCCCCGTGGCCGGGGGACTGTTGGGCGCCATCTCCTTGCATGCACCA
TTCCTTGCGGCGGCGGTGCTCAACGGCCTCAACCTACTACTGGGCTGCTTCCTAA
TGCAGGAGTCGCATAAGGGAGAGCGTCGACCGATGCCCTTGAGAGCCTTCAACCC
AGTCAGCTCCTTCCGGTGGGCGCGGGGCATGACTATCGTCGCCGCACTTATGACT
GTCTTCTTTATCATGCAACTCGTAGGACAGGTGCCGGCAGCGCTCTGGGTCATTTT
CGGCGAGGACCGCTTTCGCTGGAGCGCGACGATGATCGGCCTGTCGCTTGCGGT
ATTCGGAATCTTGCACGCCCTCGCTCAAGCCTTCGTCACTGGTCCCGCCACCAAA
CGTTTCGGCGAGAAGCAGGCCATTATCGCCGGCATGGCGGCCGACGCGCTGGGC
TACGTCTTGCTGGCGTTCGCGACGCGAGGCTGGATGGCCTTCCCCATTATGATTC
TTCTCGCTTCCGGCGGCATCGGGATGCCCGCGTTGCAGGCCATGCTGTCCAGGC
AGGTAGATGACGACCATCAGGGACAGCTTCAAGGATCGCTCGCGGCTCTTACCAG
CCTAACTTCGATCATTGGACCGCTGATCGTCACGGCGGATTTATGCCGCCTCGGCG
AGCACATGGAACGGGTTGGCATGGATTGTAGGCGCCGCCCTATACCTTGTCTGCC
TCCCCGCGTTGCGTCGCGGTGCATGGAGCCGGGCCACCTCGACCTGA SEQ ID NO: 2 (Escherichia coli TetA polypeptide sequence, encoded
by tetA gene)
MKSNNALIVILGTVTLDAVGIGLVMPVLPGLLRDIVHSDSIASHYGVLLALYALMQFLCAP
VLGALSDRFGRRPVLLASLLGATIDYAIMATTPVLWILYAGRIVAGITGATGAVAGAYIAD
ITDGEDRARHFGLMSACFGVGMVAGPVAGGLLGAISLHAPFLAAAVLNGLNLLLGCFL
MQESHKGERRPMPLRAFNPVSSFRWARGMTIVAALMTVFFIMQLVGQVPAALVVVIFG
EDRFRWSATMIGLSLAVFGILHALAQAFVTGPATKRFGEKQAIIAGMAADALGYVLLAF
ATRGVVMAFPIMILLASGGIGMPALQAMLSRQVDDDHQGQLQGSLAALTSLTSIIGPLIV
TAIYAASASTWNGLAWIVGAALYLVCLPALRRGAWSRATST SEQ ID NO: 3 (Escherichia coli aspartokinase III polypeptide
sequence, LysC, encoded by lysC gene)
MSEIVVSKFGGTSVADFDAMNRSADIVLSDANVRLVVLSASAGITNLLVA
LAEGLEPGERFEKLDAIRNIQFAILERLRYPNVIREEIERLLENITVLAE
AAALATSPALTDELVSHGELMSTLLFVEILRERDVQAQWFDVRKVMRTND
RFGRAEPDIAALAELAALQLLPRLNEGLVITQGFIGSENKGRTTTLGRGG
SDYTAALLAEALHASRVDIVVTDVPGIYTTDPRVVSAAKRIDEIAFAEAAE
MATFGAKVLHPATLLPAVRSDIPVFVGSSKDPRAGGTLVCNKTENPPLFR
ALALRRNQTLLTLHSLNMLHSRGFLAEVFGILARHNISVDLITTSEVSVA

SEQUENCE LISTINGS

```
LTLDTTGSTSTGDTLLTQSLLMELSALCRVEVEEGLALVALIGNDLSKAC
GVGKEVFGVLEPFNIRMICYGASSHNLCFLVPGEDAEQVVQKLHSNLFE

SEQ ID NO: 4 (Escherichia coli dihydrodipicolinate synthase
polypeptide sequence, DapA, encoded by dapA gene)
MFTGSIVAIVTPMDEKGNVCRASLKKLIDYHVASGTSAIVSVGTTGESATLNHDEHADV
VMMTLDLADGRIPVIAGTGANATAEAISLTQRFNDSGIVGCLTVTPYYNRPSQEGLYQH
FKAIAEHTDLPQILYNVPSRTGCDLLPETVGRLAKVKNIIGIKEATGNLTRVNQIKELVSD
DFVLLSGDDASALDFMQLGGHGVISVTANVAARDMAQMCKLAAEGHFAEARVINQRL
MPLHNKLFVEPNPIPVKWACKELGLVATDTLRLPMTPITDSGRETVRAALKHAGLL SEQ ID NO: 5 (Escherichia coli meso-diaminopimelate decarboxylase
polypeptide sequence, LysA, encoded by lysA gene)
MPHSLFSTDTDLTAENLLRLPAEFGCPVWVYDAQIIRRQIAALKQFDVVR
FAQKACSNIHILRLMREQGVKVDSVSLGEIERALAAGYNPQTHPDDIVFTADVIDQATLE
RVSELQIPVNAGSVDMLDQLGQVSPGHRVWLRVNPGFGHGHSQKTNTGGENSKHGI
VVYTDLPAALDVIQRRHHLQLVGIHMHIGSGVDYAHLEQVCGAMVRQVIEFGQDLQAISA
GGGLSVPYQQGEEAVDTEHYYGLWNAAREQIARHLGHPVKLEIEPGRFLVAQSGVLIT
QVRSVKQMGSRHFVLVDAGFNDLMRPAMYGSYHHISALAADGRSLEHAPTVETVVAG
PLCESGDVFTQQEGGNVETRALPEVKAGDYLVLHDTGAYGASMSSNYNSRPLLPEVL
FDNGQARLIRRRQTIEELLALELL SEQ ID NO: 6 (Escherichia coli CadA polypeptide sequence, encoded
by cadA gene)
MNVIAILNHMGVYFKEEPIRELHRALERLNFQIVYPNDRDDLLKLIENNAR
LCGVIFDWDKYNLELCEEISKMNENLPLYAFANTYSTLDVSLNDLRLQISFFEYALGAAE
DIANKIKQTTDEYINTILPPLTKALFKYVREGKYTFCTPGHMGGTAFQKSPVGSLFYDFF
GPNTMKSDISISVSELGSLLDHSGPHKEAEQYIARVFNADRSYMVTNGTSTANKIVGMY
SAPAGSTILIDRNCHKSLTHLMMMSDVTPIYFRPTRNAYGILGGIPQSEFQHATIAKRVK
ETPNATWPVHAVITNSTYDGLLYNTDPIKKTLDVKSIHFDSAWVPYTNFSPIYEGKCGM
SGGRVEGKVIYETQSTHKLLAAFSQASMIHVKGDVNEETFNEAYMMHTTTSPHYGIVA
STETAAAMMKGNAGKRLINGSIERAIKFRKEIKRLRTESDGWFFDVWQPDHIDTTECW
PLRSDSTWHGFKNIDNEHMYLDPIKVTLLTPGMEKDGTMSDFGIPASIVAKYLDEHGIV
VEKTGPYNLLFLFSIGIDKTKALSLLRALTDFKRAFDLNLRVKNMLPSLYREDPEFYENM
RIQELAQNIHKLIVHHNLPDLMYRAFEVLPTMVMTPYAAFQKELHGMTEEVYLDEMVG
RINANMILPYPPGVPLVMPGEMITEESRPVLEFLQMLCEIGAHYPGFETDIHGAYRQA
DGRYTVKVLKEESKK SEQ ID NO: 7 (Escherichia coli LdcC polypeptide sequence (encoded
by ldcC gene))
MNIIAIMGPHGVFYKDEPIKELESALVAQGFQIIWPQNSVDLLKFIEHNPRICGVIFDWDE
YSLDLCSDINQLNEYLPLYAFINTHSTMDVSVQDMRMALWFFEYALGQAEDIAIRMRQY
TDEYLDNITPPFTKALFTYVKERKYTFCTPGHMGGTAYQKSPVGCLFYDFFGGNTLKA
DVSISVTELGSLLDHTGPHLEAEEYIARTFGAEQSYIVTNGTSTSNKIVGMYAAPSGSTL
LIDRNCHKSLAHLLMMNDVVPVWLKPTRNALGILGGIPRREFTRDSIEEKVAATTQAQW
PVHAVITNSTYDGLLYNTDWIKQTLDVPSIHFDSAWVPYTHFHPIYQGKSGMSGERVA
GKVIFETQSTHKMLAALSQASLIHIKGEYDEEAFNEAFMMHTTTSPSYPIVASVETAAA
MLRGNPGKRLINRSVERALHFRKEVQRLREESDGWFFDIWQPPQVDEAECWPVAPG
EQWHGFNDADADHMFLDPVKVTILTPGMDEQGNMSEEGIPAALVAKFLDERGIVVEKT
GPYNLLFLFSIGIDKTKAMGLLRGLTEFKRSYDLNLRIKNMLPDLYAEDPDFYRNMRIQD
LAQGIHKLIRKHDLPGLMLRAFDTLPEMIMTPHQAWQRQIKGEVETIALEQLVGRVSAN
MILPYPPGVPLLMPGEMLTKESRTVLDFLLMLCSVGQHYPGFETDIHGAKQDEDGVYR
VRVLKMAG SEQ ID NO: 8 (Pseudomonas aeruginosa ldc2 polynucleotide
sequence)
ATGTATAAAGACCTCAAATTTCCCGTCCTCATCGTCCATCGCGACATCAAGGCCGA
CACCGTTGCCGGCAACGCGTGCGGGCATCGCCCACGAACTGGAGCAGGACG
GCTTCAGCATTCTCTCCACCGCCAGCTCCGCCGAGGGGCGCATCGTCGCTTCCAC
CCACCACGGCCTGGCCTGCATTCTGGTCGCCGCCGAAGGTGCCGGGGAAAACCA
GCGCCTGCTGCAGGATGTGGTCGAACTGATCCGCGTGGCCCGCGTGCGGGCGCC
GCAATTGCCGATCTTCGCCCTCGGCGAGCAGGTGACCATCGAGAACGCGCCGGC
CGAGTCCATGGCCGACCTGCACCAGTTGCGCGGCATCCTCTACCTGTTCGAAGAC
ACCGTGCCGTTCCTCGCCCGCCAGGTCGCCCGGGCGGCGCGCAACTACCTGGCC
GGGCTGCTGCCGCCATTCTTCCGTGCGCTGGTCGAGCACACCGCGCAGTCCAACT
ATTCCTGGCATACGCCGGGCCACGGCGGCGGTGTCGCCTATCGCAAGAGTCCGG
TGGGACAGGCGTTCCACCAGTTCTTCGGGGAGAACACGCTGCGTTCCGACCTGTC
GGTCTCGGTCCCCGAGCTGGGATCGCTGCTGACCATACCGGCCCCCTGGCCGA
GGCCGAGGACCGTGCCGCGCGCAATTTCGGCGCCGACCATACCTTCTTCGTGATC
AATGGCACTTCCACCGCGAACAAGATCGTCTGGCACTCCATGGTCGGTCGCGAAG
ACCTGGTGCTGGTGGACCGCAACTGCCACAAGTCGATCCTCCACTCGATCATCAT
GACCGGGGCGATACCGCTCTACCTGACTCCGGAACGCAACGAACTGGGGATCAT
CGGGGCCGATCCCGCTGAGCGAATTCAGCAAGCAGTCGATCGCCGCGAAGATCGC
CGCCAGCCCGCTGGCGCGCGGCCGCGAGCCGAAGGTGAAGCTGGCGGTGGTGA
CTAACTCCACCTACGACGGCCTGTGCTACAACGCCGAGCTGATCAAGCAGACCCT
CGGCGACAGCGTCGAGGTGTTGCACTTCGACGAGGCTTGGTACGCCTATGCCGC
GTTCCACGAGTTCTACGACGGACGCTATGGCATGGGCACCTCGCGCAGCGAGGA
```

```
GGGACCCCTGGTGTTCGCCACCCACTCCACGCACAAGATGCTCGCCGCCTTCAGC
CAGGCCTCGATGATCCACGTGCAGGATGGCGGGACCCGGAAGCTGGACGTGGCG
CGCTTCAACGAAGCCTTCATGATGCACATCTCGACCTCGCCGCAGTACGGCATCA
TCGCTTCGCTGGACGTGGCTTCGGCGATGATGGAAGGGCCCGCCGGGCGTTCGC
TGATCCAGGAGACCTTCGACGAGGCCCTCAGCTTCCGCCGGGCCCTGGCCAACG
TACGGCAGAACCTGGACCGGAACGACTGGTGGTTCGGCGTCTGGCAGCCGGAGC
AGGTGGAGGGCACCGACCAGGTCGGCACCCATGACTGGGTGCTGGAGCCGAGC
GCCGACTGGCACGGCTTCGGCGATATCGCCGAAGACTACGTGCTGCTCGACCCG
ATCAAGGTCACCCTGACCACCCCGGGCCTGAGCGCTGGCGGCAAGCTCAGCGAG
CAGGGGATTCCGGCCGCCATCGTCAGCCGCTTCCTCTGGGAGCGCGGGCTGGTG
GTGGAGAAAACCGGTCTCTACTCCTTCCTGGTGCTGTTCTCGATGGGCATCACCAA
GGGCAAGTGGAGCACCCTGGTCACCGAACTGCTCGAATTCAAGCGCTGTTACGAC
GCCAACCTGCCGCTGCTTGACGTCTTGCCCTCCGTGGCCCAGGCCGGCGGCAAG
CGCTACAACGGAGTGGGCCTGCGCGACCTCAGCGACGCCATGCACGCCAGCTAC
CGCGACAACGCCACGGCGAAGGCCATGAAGCGCATGTACACGGTGCTGCCGGAG
GTCGCGATGCGGCCGTCCGAGGCCTACGACAAGCTGGTGCGCGGCGAGGTCGA
GGCGGTACCGATCGCTCGGTTGGAAGGGCGCATCGCGGCCGTCATGCTGGTACC
CTATCCGCCGGGTATCCCGCTGATCATGCCGGGTGAGCGCTTCACCGAGGCGAC
CCGCTCGATCCTCGACTATCTCGAGTTCGCGCGGACCTTCGAGCGCGCCTTCCCT
GGTTTCGACTCCGATGTGCATGGCCTGCAGCATCAGGACGGACCGTCCGGGCGC
TGCTATACCGTTGAATGCATAAAGGAATGA

SEQ ID NO: 9 (Pseudomonas aeruginosa Ldc2 polypeptide sequence
(encoded by Idc2 gene))
MYKDLKFPVLIVHRDIKADTVAGERVRGIAHELEQDGFSILSTASSAEGRIVASTHHGLA
CILVAAEGAGENQRLLQDVVELIRVARVRAPQLPIFALGEQVTIENAPAESMADLHQLR
GILYLFEDTVPFLARQVARAARNYLAGLLPPFFRALVEHTAQSNYSWHTPGHGGGVAY
RKSPVGQAFHQFFGENTLRSDLSVSVPELGSLLDHTGPLAEAEDRAARNFGADHTFF
VINGTSTANKIVWHSMVGREDLVLVDRNCHKSILHSIIMTGAIPLYLTPERNELGIIGPIPL
SEFSKQSIAAKIAASPLARGREPKVKLAVVTNSTYDGLCYNAELIKQTLGDSVEVLHFDE
AVVYAYAAFHEFYDGRYGMGTSRSEEGPLVFATHSTHKMLAAFSQASMIHVQDGGTR
KLDVARFNEAFMMHISTSPQYGIIASLDVASAMMEGPAGRSLIQETFDEALSFRRALAN
VRQNLDRNDVVWFGVWQPEQVEGTDQVGTHDWVLEPSADWHGFGDIAEDYVLLDPI
KVTLTTPGLSAGGKLSEQGIPAAIVSRFLWERGLVVEKTGLYSFLVLFSMGITKGKWST
LVTELLEFKRCYDANLPLLDVLPSVAQAGGKRYNGVGLRDLSDAMHASYRDNATAKA
MKRMYTVLPEVAMRPSEAYDKLVRGEVEAVPIARLEGRIAAVMLVPYPPGIPLIMPGER
FTEATRSILDYLEFARTFERAFPGFDSDVHGLQHQDGPSGRCYTVECIKE SEQ ID NO: 10 (Pseudomonas aeruginosa (Idc2-co1 DNA sequence))
ATGTACAAAGATCTGAAATTCCCTGTTCTGATTGTACACCGCGATATCAAGGCGGA
CACGGTAGCCGGCGAGCGTGTTCGCGGTATTGCCCACGAACTCGAACAAGACGG
CTTTAGCATTCTCTCTACGGCGTCTTCTGCGGAAGGCCGCATTGTGGCTAGCACG
CACCACGGTCTCGCCTGCATCCTCGTGGCAGCTGAGGGTGCGGGTGAGAATCAG
CGTCTGCTCCAAGACGTGGTTGAGCTGATCCGTGTAGCTCGCGTCCGTGCGCCAC
AGCTCCCGATCTTCGCGCTGGGCGAACAGGTGACTATTGAAAACGCGCCTGCCGA
ATCTATGGCCGACCTGCACCAGCTCCGCGGCATTCTGTATCTCTTCGAGGATACTG
TCCCGTTCCTGGCACGTCAGGTTGCACGCGCAGCGCGTAACTACCTCGCTGGCCT
CCTCCCGCCATTCTTCCGTGCACTCGTGGAGCACACGGCCCAAAGCAATTACTCTT
GGCACACCCCGGGTCACGGTGGTGGTGTCGCTTACCGTAAATCTCCGGTAGGTCA
AGCTTTCCACCAGTTCTTTGGCGAGAATACCCTCCGCTCTGACCTGTCTGTTAGCG
TTCCAGAGCTGGGCAGCCTGCTGGATCACACTGGCCCTCTCGCGGAAGCAGAGG
ATCGTGCCGCTCGCAATTTCGGTGCGGACCACACCTTCTTTGTCATCAATGGTACC
TCTACTGCGAACAAAATCGTTTGGCACTCTATGGTTGGTCGCGAGGACCTGGTGCT
GGTCGATCGTAACTGTCACAAATCTATTCTGCACTCCATTATCATGACGGGTGCTAT
CCCACTGTACCTGACTCCGGAACGCAACGAACTGGGTATTATCGGCCCTATTCCA
CTCTCCGAGTTTTCTAAACAATCTATCGCAGCAAAAATTGCCGCCTCCCCACTCGC
GCGTGGTCGTGAACCGAAAGTTAAACTGGCTGTCGTTACCAACTCTACCTATGACG
GTCTGTGTTACAACGCGGAACTGATCAAACAAACCCTCGGCGACTCTGTCGAGGT
ACTGCATTTCGACGAGGCTTGGTATGCTTATGCGGCGTTTCACGAGTTCTACGACG
GCCGCTACGGTATGGGCACTTCTCGTTCCGAAGAGGGTCCGCTGGTCTTTGCTAC
CCATTCTACCCACAAGATGCTCGCGGCTTTTTCCCAAGCTAGCATGATTCACGTTC
AGGATGGTGGTACGCGCAAGCTGGACGTCGCCCGCTTTAACGAAGCCTTTATGAT
GCACATCAGCACCTCTCCACAGTACGGCATCATTGCGTCTCTCGATGTCGCAAGC
GCTATGATGGAAGGTCCTGCCGGTCGTAGCCTGATCAAGAGACGTTCGATGAGG
CGCTGTCCTTCCGTCGTGCTCTGGCGAATGTCCGTCAGAACCTGGACCGTAATGA
TTGGTGGTTCGGTGTCTGGCAACCGGAGCAGGTTGAGGGCACCGACCAGGTAGG
TACTCACGACTGGGTTCTCGAGCCTAGCGCGGACTGGCATGGTTTTGGTGACATT
GCGGAGGATTACGTTCTCCTCGATCCTATCAAAGTTACCCTGACCACCCCAGGTCT
GAGCGCTGGCGGTAAACTCTCTGAACAAGGCATCCCGGCAGCTATCGTTAGCCGT
TTCCTGTGGGAACGTGGTCTGGTGGTCGAGAAAACGGGTCTGTACTCTTTCCTGG
TTCTGTTCTCCATGGGTATCACGAAAGGCAAATGGTCTACTCTGGTTACCGAGCTG
CTCGAATTCAAACGCTGTTACGACGCGAATCTGCCACTCCTGGATGTGCTGCCTTC
TGTAGCGCAGGCGGGTGGTAAACGCTATAACGGTGTAGGTCTGCGTGATCTGTCC
GATGCCATGCACGCTTCTTATCGTGACAATGCCACGGCGAAGGCCATGAAGCGTA
TGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCG
GCGGTTATGCTGGTTCCGTACCCGCCAGGTATCCCGCTCATTATGCCGGGTGAAC
```

-continued

```
                      SEQUENCE LISTINGS
GTTTTACTGAAGCTACCCGCTCCATTCTGGACTATCTGGAGTTTGCCCGTACCTTC
GAGCGCGCGTTCCCGGGCTTTGACTCTGATGTTCACGGCCTCCAACATCAAGATG
GCCCGTCTGGCCGTTGTTATACCGTTGAATGCATCAAGGAATAA

SEQ ID NO: 11 (Pseudomonas aeruginosa mutant Ldc2 S111C
polypeptide sequence (encoded by mutant ldc2 gene))
MYKDLKFPVLIVHRDIKADTVAGERVRGIANELEQDGFSILSTASSAEGRIVASTHHGLA
CILVAAEGAGENQRLLQDVVELIRVARVRAPQLPIFALGEQVTIENAPAECMADLHQLR
GILYLFEDTVPFLARQVARAARNYLAGLLPPFFRALVEHTAQSNYSWHTPGHGGGVAY
RKSPVGQAFHQFFGENTLRSDLSVSVPELGSLLDHTGPLAEAEDRAARNFGADHTFF
VINGTSTANKIVWHSMVGREDLVLVDRNCHKSILHSIIMTGAIPLYLTPERNELGIIGPIPL
SEFSKQSIAAKIAASPLARGREPKVKLAVVTNSTYDGLCYNAELIKQTLGDSVEVLHFDE
AVVYAYAAFHEFYDGRYGMGTSRSEEGPLVFATHSTHKMLAAFSQASMIHVQDGGTR
KLDVARFNEAFMMHISTSPQYGIIASLDVASAMMEGPAGRSLIQETFDEALSFRRALAN
VRQNLDRNDWWFGVWQPEQVEGTDQVGTHDWVLEPSADWHGFGDIAEDYVLLDPI
KVTLTTPGLSAGGKLSEQGIPAAIVSRFLWERGLVVEKTGLYSFLVLFSMGITKGKWST
LVTELLEFKRCYDANLPLLDVLPSVAQAGGKRYNGVGLRDLSDAMHASYRDNATAKA
MKRMYTVLPEVAMRPSEAYDKLVRGEVEAVPIARLEGRIAAVMLVPYPPGIPLIMPGER
FTEATRSILDYLEFARTFERAFPGFDSDVHGLQHQDGPSGRCYTVECIKE SEQ ID NO: 12 (aat)
>gb|AY271828.1|:385-1717 H. alvei plasmid pAlvA, complete sequence
    1 ttgactttgt taaagtcag gcataagatc aaaatactgt atatataaca atgtatttat
   61 atacagtatt ttatactttt tatctaacgt cagagaggac aatattatga gtggtggaga
  121 tggcaagggt cacaatagtg gagcacatga ttccggtggc agcattaatg gaacttctgg
  181 gaaaggtggg ccatcaagcg gaggagcatc agataattct gggtggagtt cggaaaataa
  241 cccgtggggc ggtggtaact cgggaatgat tggtggcagt caaggaggta acggagctaa
  301 tcatggtggc gaaaatacat cttctaacta tgggaaagat gtatcacgcc aaatcggtga
  361 tgcgatagcc agaaaggaag gcatcaatcc gaaaatattc actgggtact ttatccgttc
  421 agatggatat ttgatcggaa taacgccact tgtcagtggt gatgcctttg gcgttaatct
  481 tggcctgttc aataacaatc aaaatagtag tagtgaaaat aagggatgga atgaaggaa
  541 tggagatggc attaaaata gtagccaagg tggatggaag attaaaacta tgaacttac
  601 ttcaaaccaa gtagctgctg ctaaatccgt tccagaacct aaaaatagta aattattaa
  661 gtccatgaga gaagctagcg atgaggttat taattctaat ttaaaccaag ggcatggagt
  721 tggtgaggca gctagagctg aaagagatta cagagaaaaa gtaaagaacg caatcaatga
  781 taatagtccc aatgtgctac aggatgctat taaatttaca gcagatttt ataaggaagt
  841 ttttaacgct tacggagaaa aagccgaaaa actagccaag ttattagctg atcaagctaa
  901 aggtaaaaag atccgcaatg tagaagatgc attgaaatct tatgaaaac acaaggctaa
  961 cattaacaaa aaaatcaatg cgaaagatcg cgaagctatc gccaaggctt tggagtctat
 1021 ggatgtagaa aaagccgcaa aaatatatc caagttcagc aaaggactag gttgggttgg
 1081 cccagctatc gatataactg attggttac agaattatac aaagcagtga aaactgataa
 1141 ttggagatct ctttatgtta aaactgaaac tattgcagta gggctagctg caacccatgt
 1201 caccgcctta gcattcagtg ctgtcttggg tgggcctata ggtattttag gttatggttt
 1261 gattatggct ggggttgggg cgttagttaa cgagacaata gttgacgagg caaataaggt
 1321 cattgggatt taa SEQ ID NO: 13 (aai)
>gb|AY271828.1|:1734-2069 H. alvei plasmid pAlvA, complete sequence
    1 ctatatttta gcggtcacat tttttatttc aaaacaaaca gaaagaacac caataggaat
   61 tgatgtcata aaaataaaaa taaaatacaa agtcattaaa tatgttttg gcacaccatc
  121 cttaaaaaaa cctgttttcc aaaattcttt tttcgtatat ctaagcgctg ctttctctat
  181 tagaaaccga gagaaaggaa atagaatagc gctagccaaa ccaaagattc tgagcgcaat
  241 tattttaggt tcgtcatcac cataactggc gtaaagaata caagcagcca taaagtatcc
  301 ccaaaacata ttatgtatgt aatatttcct tgtcat SEQ ID NO: 14 (abt)
>gb|AY271829.1|:384-1566 H. alvei plasmid pAlvB, complete sequence
    1 atgagtggtg gagacggtaa aggtcacaat agtggagcac atgattccgg tggcagcatt
   61 aatggaactt cggggaaagg tggacctgat tctggtggcg gatattggga caactcatcca
  121 catattacaa tcaccggtgg acgggaagta ggtcaagggg gagctggtat caactggatg
  181 ggtggttctg gtcatggtaa cggcggggc tcagttgcca tccaagaata taacacgagt
  241 aaatatccta acacgggagg atttcctcct cttggagacg ctagctggct gttaaatcct
  301 ccaaaatggt cggttattga agtaaaatca gaaaactcag catggcgctc ttatattact
  361 catgttcaag gtcatgttta caaattgact tttgatggta cgggtaagct cattgatacc
  421 gcgtatgtta attatgaacc cagtgatgat actcgttgga gcccgcttaa aagttttaaa
  481 tataataaag gaaccgctga aaacaggtt agggatgcca ttaacaatga aaagaagca
  541 gttaaggacg ctgttaaatt tactgcagac ttcataaag aggttttaa ggtttacgga
  601 gaaaagccg agaagctcgc taagttatta gcagatcaag ctaaaggcaa aaaggttcgc
  661 aacgtagaag atgccttgaa atcttatgaa aaatataaga ctaacattaa caaaaaatc
  721 aatgcgaaag atcgcgaagc tattgctaaa gcctgaagt ctatgatgt aggaaagcc
  781 gcaaaaaata tagccaagtt cagtaaagga ctaggttggg ttggcctgc tatcgatata
  841 actgattggt ttcagaatt ataaagca gtggaaactg ataattggag atcttttat
  901 gttaaaactg aaactattgc agtagggcta gctgcaaccc atgttccgc cttggcattc
  961 agcgctgtct gggtgggcc tgtaggtatt tgggttatg gttgattat ggctgggt
 1021 ggggcgttag ttaatgagac aatagttgac gaggcaaata aggttattgg gctttaa
```

SEQUENCE LISTINGS

SEQ ID NO: 15 (abi)
>gb|AY271829.1|:1583-1918 H. alvei plasmid pAlvB, complete sequence
```
  1 ctataattta gcggtcacat tttttatttc aaaaaaaaca gaaataacac ctataggaat
 61 tgatgtcata aaaataaaaa ttaaatacaa agtcattaaa tatgtttttg gcacgccatc
121 cttaaaaaaa ccagtttccc aaaattcttt tttcgtatat ctaagcgcgg ttttctctat
181 taaaaaccga gagaaaggga ataggatagc actagccaaa ccaagattc tgagcgcaat
241 tattttaggt tcgttatccc cataactggc gtaaagaata caaacagcca taagtaccc
301 ccaaaacata ttatgtatat aatatttcct tgtcat
```

SEQ ID NO: 16 (Ldc2 N262T protein sequence)
MYKDLKFPVLIVHRDIKADTVAGERVRGIAHELEQDGFSILSTASSAEGRIVASTHHGLA
CILVAAEGAGENQRLLQDVVELIRVARVRAPQLPIFALGEQVTIENAPAESMADLHQLR
GILYLFEDTVPFLARQVARAARNYLAGLLPPFFRALVEHTAQSNYSWHTPGHGGGVAY
RKSPVGQAFHQFFGENTLRSDLSVSVPELGSLLDHTGPLAEAEDRAARNFGADHTFF
VINGTSTANKIVWHSMVGREDLVLVDRTCHKSILHSIIMTGAIPLYLTPERNELGIIGPIPL
SEFSKQSIAAKIAASPLARGREPKVKLAVVTNSTYDGLCYNAELIKQTLGDSVEVLHFDE
AVVYAYAAFHEFYDGRYGMGTSRSEEGPLVFATHSTHKMLAAFSQASMIHVQDGGTR
KLDVARFNEAFMMHISTSPQYGIIASLDVASAMMEGPAGRSLIQETFDEALSFRRALAN
VRQNLDRNDVVWFGVWQPEQVEGTDQVGTHDVVVLEPSADWHGFGDIAEDYVLLDPI
KVTLTTPGLSAGGKLSEQGIPAAIVSRFLWERGLVVEKTGLYSFLVLFSMGITKGKWST
LVTELLEFKRCYDANLPLLDVLPSVAQAGGKRYNGVGLRDLSDAMHASYRDNATAKA
MKRMYTVLPEVAMRPSEAYDKLVRGEVEAVPIARLEGRIAAVMLVPYPPGIPLIMPGER
FTEATRSILDYLEFARTFERAFPGFDSDVHGLQHQDGPSGRCYTVECIKE SEQ ID NO: 17 (Ldc2 K265N protein sequence)
MYKDLKFPVLIVHRDIKADTVAGERVRGIAHELEQDGFSILSTASSAEGRIVASTHHGLA
CILVAAEGAGENQRLLQDVVELIRVARVRAPQLPIFALGEQVTIENAPAESMADLHQLR
GILYLFEDTVPFLARQVARAARNYLAGLLPPFFRALVEHTAQSNYSWHTPGHGGGVAY
RKSPVGQAFHQFFGENTLRSDLSVSVPELGSLLDHTGPLAEAEDRAARNFGADHTFF
VINGTSTANKIVWHSMVGREDLVLVDRNCHNSILHSIIMTGAIPLYLTPERNELGIIGPIPL
SEFSKQSIAAKIAASPLARGREPKVKLAVVTNSTYDGLCYNAELIKQTLGDSVEVLHFDE
AVVYAYAAFHEFYDGRYGMGTSRSEEGPLVFATHSTHKMLAAFSQASMIHVQDGGTR
KLDVARFNEAFMMHISTSPQYGIIASLDVASAMMEGPAGRSLIQETFDEALSFRRALAN
VRQNLDRNDVVWFGVWQPEQVEGTDQVGTHDVVVLEPSADWHGFGDIAEDYVLLDPI
KVTLTTPGLSAGGKLSEQGIPAAIVSRFLWERGLVVEKTGLYSFLVLFSMGITKGKWST
LVTELLEFKRCYDANLPLLDVLPSVAQAGGKRYNGVGLRDLSDAMHASYRDNATAKA
MKRMYTVLPEVAMRPSEAYDKLVRGEVEAVPIARLEGRIAAVMLVPYPPGIPLIMPGER
FTEATRSILDYLEFARTFERAFPGFDSDVHGLQHQDGPSGRCYTVECIKE SEQ ID NO: 18 (Ldc2 S111C/N262T protein sequence)
MYKDLKFPVLIVHRDIKADTVAGERVRGIAHELEQDGFSILSTASSAEGRIVASTHHGLA
CILVAAEGAGENQRLLQDVVELIRVARVRAPQLPIFALGEQVTIENAPAECMADLHQLR
GILYLFEDTVPFLARQVARAARNYLAGLLPPFFRALVEHTAQSNYSWHTPGHGGGVAY
RKSPVGQAFHQFFGENTLRSDLSVSVPELGSLLDHTGPLAEAEDRAARNFGADHTFF
VINGTSTANKIVWHSMVGREDLVLVDRTCHKSILHSIIMTGAIPLYLTPERNELGIIGPIPL
SEFSKQSIAAKIAASPLARGREPKVKLAVVTNSTYDGLCYNAELIKQTLGDSVEVLHFDE
AVVYAYAAFHEFYDGRYGMGTSRSEEGPLVFATHSTHKMLAAFSQASMIHVQDGGTR
KLDVARFNEAFMMHISTSPQYGIIASLDVASAMMEGPAGRSLIQETFDEALSFRRALAN
VRQNLDRNDVVWFGVWQPEQVEGTDQVGTHDVVVLEPSADWHGFGDIAEDYVLLDPI
KVTLTTPGLSAGGKLSEQGIPAAIVSRFLWERGLVVEKTGLYSFLVLFSMGITKGKWST
LVTELLEFKRCYDANLPLLDVLPSVAQAGGKRYNGVGLRDLSDAMHASYRDNATAKA
MKRMYTVLPEVAMRPSEAYDKLVRGEVEAVPIARLEGRIAAVMLVPYPPGIPLIMPGER
FTEATRSILDYLEFARTFERAFPGFDSDVHGLQHQDGPSGRCYTVECIKE SEQ ID NO: 19 (Ldc2 S111C/K265N protein sequence)
MYKDLKFPVLIVHRDIKADTVAGERVRGIAHELEQDGFSILSTASSAEGRIVASTHHGLA
CILVAAEGAGENQRLLQDVVELIRVARVRAPQLPIFALGEQVTIENAPAECMADLHQLR
GILYLFEDTVPFLARQVARAARNYLAGLLPPFFRALVEHTAQSNYSWHTPGHGGGVAY
RKSPVGQAFHQFFGENTLRSDLSVSVPELGSLLDHTGPLAEAEDRAARNFGADHTFF
VINGTSTANKIVWHSMVGREDLVLVDRNCHNSILHSIIMTGAIPLYLTPERNELGIIGPIPL
SEFSKQSIAAKIAASPLARGREPKVKLAVVTNSTYDGLCYNAELIKQTLGDSVEVLHFDE
AVVYAYAAFHEFYDGRYGMGTSRSEEGPLVFATHSTHKMLAAFSQASMIHVQDGGTR
KLDVARFNEAFMMHISTSPQYGIIASLDVASAMMEGPAGRSLIQETFDEALSFRRALAN
VRQNLDRNDVVWFGVWQPEQVEGTDQVGTHDVVVLEPSADWHGFGDIAEDYVLLDPI
KVTLTTPGLSAGGKLSEQGIPAAIVSRFLWERGLVVEKTGLYSFLVLFSMGITKGKWST
LVTELLEFKRCYDANLPLLDVLPSVAQAGGKRYNGVGLRDLSDAMHASYRDNATAKA
MKRMYTVLPEVAMRPSEAYDKLVRGEVEAVPIARLEGRIAAVMLVPYPPGIPLIMPGER
FTEATRSILDYLEFARTFERAFPGFDSDVHGLQHQDGPSGRCYTVECIKE SEQ ID NO: 20 (Ldc2 N262T/K265N protein sequence)
MYKDLKFPVLIVHRDIKADTVAGERVRGIAHELEQDGFSILSTASSAEGRIVASTHHGLA
CILVAAEGAGENQRLLQDVVELIRVARVRAPQLPIFALGEQVTIENAPAESMADLHQLR
GILYLFEDTVPFLARQVARAARNYLAGLLPPFFRALVEHTAQSNYSWHTPGHGGGVAY
RKSPVGQAFHQFFGENTLRSDLSVSVPELGSLLDHTGPLAEAEDRAARNFGADHTFF
VINGTSTANKIVWHSMVGREDLVLVDRTCHNSILHSIIMTGAIPLYLTPERNELGIIGPIPL
SEFSKQSIAAKIAASPLARGREPKVKLAVVTNSTYDGLCYNAELIKQTLGDSVEVLHFDE

| SEQUENCE LISTINGS |
|---|

```
AVVYAYAAFHEFYDGRYGMGTSRSEEGPLVFATHSTHKMLAAFSQASMIHVQDGGTR
KLDVARFNEAFMMHISTSPQYGIIASLDVASAMMEGPAGRSLIQETFDEALSFRRALAN
VRQNLDRNDVVWFGVWQPEQVEGTDQVGTHDVVVLEPSADWHGFGDIAEDYVLLDPI
KVTLTTPGLSAGGKLSEQGIPAAIVSRFLWERGLVVEKTGLYSFLVLFSMGITKGKWST
LVTELLEFKRCYDANLPLLDVLPSVAQAGGKRYNGVGLRDLSDAMHASYRDNATAKA
MKRMYTVLPEVAMRPSEAYDKLVRGEVEAVPIARLEGRIAAVMLVPYPPGIPLIMPGER
FTEATRSILDYLEFARTFERAFPGFDSDVHGLQHQDGPSGRCYTVECIKE

SEQ ID NO: 21 (Ldc2 S111C/N262T/K265N protein sequence)
MYKDLKFPVLIVHRDIKADTVAGERVRGIAHELEQDGFSILSTASSAEGRIVASTHHGLA
CILVAAEGAGENQRLLQDVVELIRVARVRAPQLPIFALGEQVTIENAPAECMADLHQLR
GILYLFEDTVPFLARQVARAARNYLAGLLPPFFRALVEHTAQSNYSWHTPGHGGGVAY
RKSPVGQAFHQFFGENTLRSDLSVSVPELGSLLDHTGPLAEAEDRAARNFGADHTFF
VINGTSTANKIVWHSMVGREDLVLVDRTCHNSILHSIIMTGAIPLYLTPERNELGIIGPIPL
SEFSKQSIAAKIAASPLARGREPKVKLAVVTNSTYDGLCYNAELIKQTLGDSVEVLHFDE
AVVYAYAAFHEFYDGRYGMGTSRSEEGPLVFATHSTHKMLAAFSQASMIHVQDGGTR
KLDVARFNEAFMMHISTSPQYGIIASLDVASAMMEGPAGRSLIQETFDEALSFRRALAN
VRQNLDRNDVVWFGVWQPEQVEGTDQVGTHDVVVLEPSADWHGFGDIAEDYVLLDPI
KVTLTTPGLSAGGKLSEQGIPAAIVSRFLWERGLVVEKTGLYSFLVLFSMGITKGKWST
LVTELLEFKRCYDANLPLLDVLPSVAQAGGKRYNGVGLRDLSDAMHASYRDNATAKA
MKRMYTVLPEVAMRPSEAYDKLVRGEVEAVPIARLEGRIAAVMLVPYPPGIPLIMPGER
FTEATRSILDYLEFARTFERAFPGFDSDVHGLQHQDGPSGRCYTVECIKE SEQ ID NO: 22 (Escherichia coli Asd polypeptide sequence (encoded
by asd gene))
MKNVGFIGWRGMVGSVLMQRMVEERDFDAIRPVFFSTSQLGQAAPSFGGT
TGTLQDAFDLEALKALDIIVTCQGGDYTNEIYPKLRESGWQGYWIDASSS
LRMKDDAIIILDPVNQDVITDGLNNGIRTFVGGNCTVSLMLMSLGGLFAN
DLVDVVVSVATYQAASGGGARHMRELLTQMGHLYGHVADELATPSSAILDI
ERKVTTLTRSGELPVDNFGVPLAGSLIPWIDKQLDNGQSREEWKGQAETN
KILNTSSVIPVDGLCVRVGALRCHSQAFTIKLKKDVSIPTVEELLAAHNP
WAKVVPNDREITMRELTPAAVTGTLTTPVGRLRKLNMGPEFLSAFTVGDQ
LLWGAAEPLRRMLRQLA SEQ ID NO: 23 (Escherichia coli DapB polypeptide sequence
(encoded by dapB gene))
MHDANIRVAIAGAGGRMGRQLIQAALALEGVQLGAALEREGSSLLGSDAG
ELAGAGKTGVTVQSSLDAVKDDFDVFIDFTRPEGTLNHLAFCRQHGKGMV
IGTTGFDEAGKQAIRDAAADIAIVFAANFSVGVNVMLKLLEKAAKVMGDY
TDIEIIEAHHRHKVDAPSGTALAMGEAIAHALDKDLKDCAVYSREGHTGE
RVPGTIGFATVRAGDIVGEHTAMFADIGERLEITHKASSRMTFANGAVRS
ALWLSGKESGLFDMRDVLDLNNL SEQ ID NO: 24 (Escherichia coli DapD polypeptide sequence
(encoded by dapD gene))
MQQLQNIIETAFERRAEITPANADTVTREAVNQVIALLDSGALRVAEKID
GQVVVTHQWLKKAVLLSFRINDNQVIEGAESRYFDKVPMKFADYDEARFQK
EGFRVVPPAAVRQGAFIARNTVLMPSYVNIGAYVDEGTMVDTWATVGSCA
QIGKNVHLSGGVGIGGVLEPLQANPTIIEDNCFIGARSEVVEGVIVEEGS
VISMGVYIGQSTRIYDRETGEIHYGRVPAGSVVVSGNLPSKDGKYSLYCA
VIVKKVDAKTRGKVGINELLRTID SEQ ID NO: 25 (Escherichia coli AspC polypeptide sequence
(encoded by aspC gene))
MFENITAAPADPILGLADLFRADERPGKINLGIGVYKDETGKTPVLTSVK
KAEQYLLENETTKNYLGIDGIPEFGRCTQELLFGKGSALINDKRARTAQT
PGGTGALRVAADFLAKNTSVKRVVVVSNPSWPNHKSVFNSAGLEVREYAYY
DAENHTLDFDALINSLNEAQAGDVVLFHGCCHNPTGIDPTLEQWQTLAQL
SVEKGWLPLFDFAYQGFARGLEEDAEGLRAFAAMHKELIVASSYSKNFGL
YNERVGACTLVAADSETVDRAFSQMKAAIRANYSNPPAHGASVVATILSN
DALRAIWEQELTDMRQRIQRMRQLFVNTLQEKGANRDFSFIIKQNGMFSF
SGLTKEQVLRLREEFGVYAVASGRVNVAGMTPDNMAPLCEAIVAVL SEQ ID NO: 26 (Escherichia coli mutant aspartokinase III polypeptide
sequence, LysC-1 (M318I, G3230))
MSEIVVSKFGGTSVADFDAMNRSADIVLSDANVRLVVLSASAGITNLLVA
LAEGLEPGERFEKLDAIRNIQFAILERLRYPNVIREEIERLLENITVLAE
AAALATSPALTDELVSHGELMSTLLFVEILRERDVQAQWFDVRKVMRTND
RFGRAEPDIAAALAELAALQLLPRLNEGLVITQGFIGSENKGRTTTLGRGG
SDYTAALLAEALHASRVDIVVTDVPGIYTTDPRVVSAAKRIDEIAFAEAE
MATFGAKVLHPATLLPAVRSDIPVFVGSSKDPRAGGTLVCNKTENPPLFR
ALALRRNQTLLTLHSLNILHSRDFLAEVFGILARHNISVDLITTSEVSVA
LTLDTTGSTSTGDTLLTQSLLMELSALCRVEVEEGLALVALIGNDLSKAC
GVGKEVFGVLEPFNIRMICYGASSHNLCFLVPGEDAEQVVQKLHSNLFE
```

SEQUENCE LISTINGS

SEQ ID NO: 27 (*Escherichia coli* mutant aspartokinase III polypeptide sequence, LysC-2 (T344M, T352I))
MSEIVVSKFGGTSVADFDAMNRSADIVLSDANVRLVVLSASAGITNLLVA
LAEGLEPGERFEKLDAIRNIQFAILERLRYPNVIREEIERLLENITVLAE
AAALATSPALTDELVSHGELMSTLLFVEILRERDVQAQWFDVRKVMRTND
RFGRAEPDIAALAELAALQLLPRLNEGLVITQGFIGSENKGRTTTLGRGG
SDYTAALLAEALHASRVDIVVTDVPGIYTTDPRVVSAAKRIDEIAFAEAE
MATFGAKVLHPATLLPAVRSDIPVFVGSSKDPRAGGTLVCNKTENPPLFR
ALALRRNQTLLTLHSLNMLHSRGFLAEVFGILARHNISVDLITMSEVSVA
LILDTTGSTSTGDTLLTQSLLMELSALCRVEVEEGLALVALIGNDLSKAC
GVGKEVFGVLEPFNIRMICYGASSHNLCFLVPGEDAEQVVQKLHSNLFE SEQ ID NO: 28 (*Streptomyces lividans* aspartokinase III polypeptide sequence, S-LysC)
MGLVVQKYGGSSVADAEGIKRVAKRIVEAKKNGNQVVAVVSAMGDTTDELIDLAEQVS
PIPAGRELDMLLTAGERISMALLAMAIKNLGHEAQSFTGSQAGVITDSVHNKARIIDVTP
GRIRTSVDEGNVAIVAGFQGVSQDSKDITTLGRGGSDTTAVALAAALDADVCEIYTDVD
GVFTADPRVVPKAKKIDWISFEDMLELAASGSKVLLHRCVEYARRYNIPIHVRSSFSGL
QGTVVVSSEPIKQGEKHVEQALISGVAHDTSEAKVTVVGVPDKPGEAAAIFRAIADAQV
NIDMVVQNVSAASTGLTDISFTLPKSEGRKAIDALEKNRPGIGFDSLRYDDQIGKISLVG
AGMKSNPGVTADFFTALSDAGVNIELISTSEIRISVVTRKDDVNEAVRAVHTAFGLDSD
SDEAVVYGGTGR SEQ ID NO: 29 (*Escherichia coli* tetA polynucleotide sequence, nucleotides 1-558, tetA (nt 1-558))
ATGAAATCTAACAATGCGCTCATCGTCATCCTCGGCACCGTCACCCTGGATGCTGT
AGGCATAGGCTTGGTTATGCCGGTACTGCCGGGCCTCTTGCGGGATATCGTCCAT
TCCGACAGCATCGCCAGTCACTATGGCGTGCTGCTAGCGCTATATGCGTTGATGC
AATTTCTATGCGCACCCGTTCTCGGAGCACTGTCCGACCGCTTTGGCCGCCGCCC
AGTCCTGCTCGCTTCGCTACTTGGAGCCACTATCGACTACGCGATCATGGCGACC
ACACCCGTCCTGTGGATCCTCTACGCCGGACGCATCGTGGCCGGCATCACCGGC
GCCACAGGTGCGGTTGCTGGCGCCTATATCGCCGACATCACCGATGGGGAAGAT
CGGGCTCGCCACTTCGGGCTCATGAGCGCTTGTTTCGGCGTGGGTATGGTGGCA
GGCCCCGTGGCCGGGGGACTGTTGGGCGCCATCTCCTTGCATGCACCATTCCTTG
CGGCGGCGGTGCTCAACGGCCTCAACCTACTACTGGGCTGCTTCCTAATGCAGGA
GTCGCATTAAGGGAGAGCGTCGACCGATGCCCTTGAGAGCCTTCAACCCAGTCAG
CTCCTTCCGGTGGGCGCGGGGCATGACTATCGTCGCCGCACTTATGACTGTCTTC
TTTATCATGCAACTCGTAGGACAGGTGCCGGCAGCGCTCTGGGTCATTTTCGGCG
AGGACCGCTTTCGCTGGAGCGCGACGATGATCGGCCTGTCGCTTGCGGTATTCGG
AATCTTGCACGCCCTCGCTCAAGCCTTCGTCACTGGTCCCGCCACCAAACGTTTCG
GCGAGAAGCAGGCCATTATCGCCGGCATGGCGGCCGACGCGCTGGGCTACGTCT
TGCTGGCGTTCGCGACGCGAGGCTGGATGGCCTTCCCCATTATGATTCTTCTCGC
TTCCGGCGGCATCGGGATGCCCGCGTTGCAGGCCATGCTGTCCAGGCAGGTAGA
TGACGACCATCAGGGACAGCTTCAAGGATCGCTCGCGGCTCTTACCAGCCTAACT
TCGATCATTGGACCGCTGATCGTCACGGCGATTTATGCCGCCTCGGCGAGCACAT
GGAACGGGTTGGCATGGATTGTAGGCGCCGCCCTATACCTTGTCTGCCTCCCCGC
GTTGCGTCGCGGTGCATGGAGCCGGGCCACCTCGACCTGA SEQ ID NO: 30 (*Escherichia coli* TetA polypeptide sequence, amino acids 1-185, TetA (aa1-185))
MKSNNALIVILGTVTLDAVGIGLVMPVLPGLLRDIVHSDSIASHYGVLLA
LYALMQFLCAPVLGALSDRFGRRPVLLASLLGATIDYAIMATTPVLWILY
AGRIVAGITGATGAVAGAYIADITDGEDRARHFGLMSACFGVGMVAGPVA
GGLLGAISLHAPFLAAAVLNGLNLLLGCFLMQESH SEQ ID NO: 31 (*Escherichia coli* tetA polynucleotide sequence, nucleotides 1-291, tetA (nt 1-291))
ATGAAATCTAACAATGCGCTCATCGTCATCCTCGGCACCGTCACCCTGGATGCTGT
AGGCATAGGCTTGGTTATGCCGGTACTGCCGGGCCTCTTGCGGGATATCGTCCAT
TCCGACAGCATCGCCAGTCACTATGGCGTGCTGCTAGCGCTATATGCGTTGATGC
AATTTCTATGCGCACCCGTTCTCGGAGCACTGTCCGACCGCTTTGGCCGCCGCCC
AGTCCTGCTCGCTTCGCTACTTGGAGCCACTATCGACTACGCGATCATGGCGACC
ACACCCGTCCTGTAAGGATCCTCTACGCCGGACGCATCGTGGCCGGCATCACCG
GCGCCACAGGTGCGGTTGCTGGCGCCTATATCGCCGACATCACCGATGGGGAAG
ATCGGGCTCGCCACTTCGGGCTCATGAGCGCTTGTTTCGGCGTGGGTATGGTGGC
AGGCCCCGTGGCCGGGGGACTGTTGGGCGCCATCTCCTTGCATGCACCATTCCTT
GCGGCGGCGGTGCTCAACGGCCTCAACCTACTACTGGGCTGCTTCCTAATGCAGG
AGTCGCATAAGGGAGAGCGTCGACCGATGCCCTTGAGAGCCTTCAACCCAGTCAG
CTCCTTCCGGTGGGCGCGGGGCATGACTATCGTCGCCGCACTTATGACTGTCTTC
TTTATCATGCAACTCGTAGGACAGGTGCCGGCAGCGCTCTGGGTCATTTTCGGCG
AGGACCGCTTTCGCTGGAGCGCGACGATGATCGGCCTGTCGCTTGCGGTATTCGG
AATCTTGCACGCCCTCGCTCAAGCCTTCGTCACTGGTCCCGCCACCAAACGTTTCG
GCGAGAAGCAGGCCATTATCGCCGGCATGGCGGCCGACGCGCTGGGCTACGTCT
TGCTGGCGTTCGCGACGCGAGGCTGGATGGCCTTCCCCATTATGATTCTTCTCGC
TTCCGGCGGCATCGGGATGCCCGCGTTGCAGGCCATGCTGTCCAGGCAGGTAGA
TGACGACCATCAGGGACAGCTTCAAGGATCGCTCGCGGCTCTTACCAGCCTAACT TCGATCATTGGACCGCTGATCGTCACGGCGATTTATGCCGCCTCGGCGAGCACAT
GGAACGGGTTGGCATGGATTGTAGGCGCCGCCCTATACCTTGTCTGCCTCCCCGC
GTTGCGTCGCGGTGCATGGAGCCGGGCCACCTCGACCTGA SEQ ID NO: 32 (*Escherichia coli* TetA polypeptide sequence, amino
acids 1-96, TetA (aa1-96))
MKSNNALIVILGTVTLDAVGIGLVMPVLPGLLRDIVHSDSIASHYGVLLALYALMQFLCAP
VLGALSDRFGRRPVLLASLLGATIDYAIMATTPVL SEQ ID NO: 33 (*Escherichia coli* CadA polypeptide sequence, amino
acids 1-565, CadA (aa1-565))
MNVIAILNHMGVYFKEEPIRELHRALERLNFQIVYPNDRDDLLKLIENNA
RLCGVIFDWDKYNLELCEEISKMNENLPLYAFANTYSTLDVSLNDLRLQI
SFFEYALGAAEDIANKIKQTTDEYINTILPPLTKALFKYVREGKYTFCTP
GHMGGTAFQKSPVGSLFYDFFGPNTMKSDISISVSELGSLLDHSGPHKEA
EQYIARVFNADRSYMVTNGTSTANKIVGMYSAPAGSTILIDRNCHKSLTH
LMMMSDVTPIYFRPTRNAYGILGGIPQSEFQHATIAKRVKETPNATWPVH
AVITNSTYDGLLYNTDFIKKTLDVKSIHFDSAWVPYTNFSPIYEGKCGMS
GGRVEGKVIYETQSTHKLLAAFSQASMIHVKGDVNEETFNEAYMMHTTTS
PHYGIVASTETAAAMMKGNAGKRLINGSIERAIKFRKEIKRLRTESDGWF
FDVWQPDHIDTTECWPLRSDSTWHGFKNIDNEHMYLDPIKVTLLTPGMEK
DGTMSDFGIPASIVAKYLDEHGIVVEKTGPYNLLFLFSIGIDKTKALSLL
RALTDFKRAFDLNLR SEQ ID NO: 34 (ldc2-col C332G DNA sequence)
ATGTACAAAGATCTGAAATTCCCTGTTCTGATTGTACACCGCGATATCAAGGCGGA
CACGGTAGCCGGCGAGCGTGTTCGCGGTATTGCCCACGAACTCGAACAAGACGG
CTTTTAGCATTCTCTCTACGGCGTCTTCTGCGGAAGGCCGCATTGTGGCTAGCACG
CACCACGGTCTCGCCTGCATCCTCGTGGCAGCTGAGGGTGCGGGTGAGAATCAG
CGTCTGCTCCAAGACGTGGTTGAGCTGATCCGTGTAGCTCGCGTCCGTGCGCCAC
AGCTCCCGATCTTCGCGCTGGGCGAACAGGTGACTATTGAAAACGCGCCTGCCGA
ATGTATGGCCGACCTGCACCAGCTCCGCGGCATTCTGTATCTCTTCGAGGATACTG
TCCCGTTCCTGGCACGTCAGGTTGCACGCGCAGCGCGTAACTACCTCGCTGGCCT
CCTCCCGCCATTCTTCCGTGCACTCGTGGAGCACACGGCCCAAAGCAATTACTCTT
GGCACACCCCGGGTCACGGTGGTGGTGTCGCTTACCGTAAATCTCCGGTAGGTCA
AGCTTTCCACCAGTTCTTTGGCGAGAATACCCTCCGCTCTGACCTGTCTGTTAGCG
TTCCAGAGCTGGGCAGCTGCTGGATCACACTGGCCCTCTCGCGGAAGCAGAGG
ATCGTGCCGCTCGCAATTTCGGTGCGGACCACACCTTCTTTGTCATCAATGGTACC
TCTACTGCGAACAAAATCGTTTGGCACTCTATGGTTGGTCGCGAGGACCTGGTGCT
GGTCGATCGTAACTGTCACAAATCTATTCTGCACTCCATTATCATGACGGGTGCTAT
CCCACTGTACCTGACTCCGGAACGCAACGAACTGGGTATTATCGGCCCTATTCCA
CTCTCCGAGTTTTCTAAACAATCTATCGCAGCAAAATTGCCGCCTCCCCACTCGC
GCGTGGTCGTGAACCGAAAGTTAAACTGGCTGTCGTTACCAACTCTACCTATGACG
GTCTGTGTTACAACGCGGAACTGATCAAACAAACCCTCGGCGACTCTGTCGAGGT
ACTGCATTTCGACGAGGCTTGGTATGCTTATGCGGCGTTTCACGAGTTCTACGACG
GCCGCTACGGTATGGGCACTTCTCGTTCCGAAGAGGGTCCGCTGGTCTTTGCTAC
CCATTCTACCCACAAGATGCTCGCGGCTTTTTCCCAAGCTAGCATGATTCACGTTC
AGGATGGTGGTACGCGCAAGCTGGACGTCGCCCGCTTTAACGAAGCCTTTATGAT
GCACATCAGCACCTCTCCACAGTACGGCATCATTGCGTCTCTCGATGTCGCAAGC
GCTATGATGGAAGGTCCTGCCGGTCGTAGCCTGATCCAAGAGACGTTCGATGAGG
CGCTGTCCTTCCGTCGTGCTCTGGCGAATGTCCGTCAGAACCTGGACCGTAATGA
TTGGTGGTTCGGTGTCTGGCAACCGGAGCAGGTTGAGGGCACCGACCAGGTAGG
TACTCACGACTGGGTTCTCGAGCCTAGCGCGGACTGGCATGGTTTTGGTGACATT
GCGGAGGATTACGTTCCTCGATCCTATCAAAGTTACCCTGACCACCCCAGGTCT
GAGCGCTGGCGGTAAACTCTCGAACAAGGCATCCCGGCAGCTATCGTTAGCCGT
TTCCTGTGGGAACGTGGTCTGGTGGTCGAGAAAACGGGTCTGTACTCTTTCCTGG
TTCTGTTCTCCATGGGTATCACGAAAGGCAAATGGTCTACTCGTTACCGAGCTG
CTCGAATTCAAACGCTGTTACGACGCGAATCTGCCACTCCTGGATGTGCTGCCTTC
TGTAGCGCAGGCGGGTGGTAAACGCTATAACGGTGTAGGTCTGCGTGATCGTCC
GATGCCATGCACGCTTCTTATCGTGACAATGCCACGGCGAAGGCCATGAAGCGTA
TGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCG
GCGGTTATGCTGGTTCCGTACCCGCCAGGTATCCCGCTCATTATGCCGGGTGAAC
GTTTTACTGAAGCTACCCGCTCCATTCTGGACTATCTGGAGTTTGCCCGTACCTTC
GAGCGCGCGTTCCCGGGCTTTGACTCTGATGTTCACGGCCTCCAACATCAAGATG
GCCCGTCTGGCCGTTGTTATACCGTTGAATGCATCAAGGAATAA SEQ ID NO: 35 (Idc2-col A785C DNA sequence)
ATGTACAAAGATCTGAAATTCCCTGTTCTGATTGTACACCGCGATATCAAGGCGGA
CACGGTAGCCGGCGAGCGTGTTCGCGGTATTGCCCACGAACTCGAACAAGACGG
CTTTTAGCATTCTCTCTACGGCGTCTTCTGCGGAAGGCCGCATTGTGGCTAGCACG
CAC CACGGTCTCGCCTGCATCCTCGTGGCAGCTGAGGGTGCGGGTGAGAATCAG
CGTCTGCTCCAAGACGTGGTTGAGCTGATCCGTGTAGCTCGCGTCCGTGCGCCAC
AGCTCCCGATCTTCGCGCTGGGCGAACAGGTGACTATTGAAAACGCGCCTGCCGA
ATCTATGGCCGACCTGCACCAGCTCCGCGGCATTCTGTATCTCTTCGAGGATACTG
TCCCGTTCCTGGCACGTCAGGTTGCACGCGCAGCGCGTAACTACCTCGCTGGCCT
CCTCCCGCCATTCTTCCGTGCACTCGTGGAGCACACGGCCCAAAGCAATTACTCTT

```
GGCACACCCCGGGTCACGGTGGTGGTGTCGCTTACCGTAAATCTCCGGTAGGTCA
AGCTTTCCACCAGTTCTTTGGCGAGAATACCCTCCGCTCTGACCTGTCTGTTAGCG
TTCCAGAGCTGGGCAGCCTGCTGGATCACACTGGCCCTCTCGCGGAAGCAGAGG
ATCGTGCCGCTCGCAATTTCGGTGCGGACCACACCTTCTTTGTCATCAATGGTACC
TCTACTGCGAACAAAATCGTTTGGCACTCTATGGTTGGTCGCGAGGACCTGGTGCT
GGTCGATCGTACCTGTCACAAATCTATTCTGCACTCCATTATCATGACGGGTGCTA
TCCCACTGTACCTGACTCCGGAACGCAACGAACTGGGTATTATCGGCCCTATTCCA
CTCTCCGAGTTTTCTAAACAATCTATCGCAGCAAAAATTGCCGCCTCCCCACTCGC
GCGTGGTCGTGAACCGAAAGTTAAACTGGCTGTCGTTACCAACTCTACCTATGACG
GTCTGTGTTACAACGCGGAACTGATCAAACAAACCCTCGGCGACTCTGTCGAGGT
ACTGCATTTCGACGAGGCTTGGTATGCTTATGCGGCGTTTCACGAGTTCTACGACG
GCCGCTACGGTATGGGCACTTCTCGTTCCGAAGAGGGTCCGCTGGTCTTTGCTAC
CCATTCTACCCACAAGATGCTCGCGGCTTTTTCCCAAGCTAGCATGATTCACGTTC
AGGATGGTGGTACGCGCAAGCTGGACGTCGCCCGCTTTAACGAAGCCTTTATGAT
GCACATCAGCACCTCTCCACAGTACGGCATCATTGCGTCTCTCGATGTCGCAAGC
GCTATGATGGAAGGTCCTGCCGGTCGTAGCCTGATCCAAGAGACGTTCGATGAGG
CGCTGTCCTTCCGTCGTGCTCTGGCAATGTCCGTCAGAACCTGGACCGTAATGA
TTGGTGGTTCGGTGTCTGGCAACCGGAGCAGGTTGAGGGCACCGACCAGGTAGG
TACTCACGACTGGGTTCTCGAGCCTAGCGCGGACTGGCATGGTTTTGGTGACATT
GCGGAGGATTACGTTCTCCTCGATCCTATCAAAGTTACCCTGACCACCCCAGGTCT
GAGCGCTGGCGGTAAACTCTCTGAACAAGGCATCCCGGCAGCTATCGTTAGCCGT
TTCCTGTGGGAACGTGGTCTGGTGGTCGAGAAAACGGGTCTGTACTCTTTCCTGG
TTCTGTTCTCCATGGGTATCACGAAAGGCAAATGGTCTACTCTGGTTACCGAGCTG
CTCGAATTCAAACGCTGTTACGACGCGAATCTGCCACTCCTGGATGTGCTGCCTTC
TGTAGCGCAGGCGGGTGGTAAACGCTATAACGGTGTAGGTCTGCGTGATCTGTCC
GATGCCATGCACGCTTCTTATCGTGACAATGCCACGGCGAAGGCCATGAAGCGTA
TGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCG
GCGGTTATGCTGGTTCCGTACCCGCCAGGTATCCCGCTCATTATGCCGGGTGAAC
GTTTTACTGAAGCTACCCGCTCCATTCTGGACTATCTGGAGTTTGCCCGTACCTTC
GAGCGCGCGTTCCCGGGCTTTGACTCTGATGTTCACGGCCTCCAACATCAAGATG
GCCCGTCTGGCCGTTGTTATACCGTTAATGCATCAAGGAATAA

SEQ ID NO: 36 (ldc2-col A795C DNA sequence)
ATGTACAAAGATCTGAAATTCCCTGTTCTGATTGTACACCGCGATATCAAGGCGGA
CACGGTAGCCGGCGAGCGTGTTCGCGGTATTGCCCACGAACTCGAACAAGACGG
CTTTAGCATTCTCTCTACGGCGTCTTCTGCGAAGGCCGCATTGTGGCTAGCACG
CACCACGGTCTCGCCTGCATCCTCGTGGCAGCTGAGGGTGCGGGTGAGAATCAG
CGTCTGCTCCAAGACGTGGTTGAGCTGATCCGTGTAGCTCGCGTCCGTGCGCCAC
AGCTCCCGATCTTCGCGCTGGGCGAACAGGTGACTATTGAAAACGCGCCTGCCGA
ATCTATGGCCGACCTGCACCAGCTCCGCGGCATTCTGTATCTCTTCGAGGATACTG
TCCCGTTCCTGGCACGTCAGGTTGCACGCGCAGCGCGTAACTACCTCGCTGGCCT
CCTCCCGCCATTCTTCCGTGCACTCGTGGAGCACACGGCCCAAAGCAATTACTCTT
GGCACACCCCGGGTCACGGTGGTGGTGTCGCTTACCGTAAATCTCCGGTAGGTCA
AGCTTTCCACCAGTTCTTTGGCGAGAATACCCTCCGCTCTGACCTGTCTGTTAGCG
TTCCAGAGCTGGGCAGCCTGCTGGATCACACTGGCCCTCTCGCGGAAGCAGAGG
ATCGTGCCGCTCGCAATTTCGGTGCGGACCACACCTTCTTTGTCATCAATGGTACC
TCTACTGCGAACAAAATCGTTTGGCACTCTATGGTTGGTCGCGAGGACCTGGTGCT
GGTCGATCGTAACTGTCACAACTCTATTCTGCACTCCATTATCATGACGGGTGCTA
TCCCACTGTACCTGACTCCGGAACGCAACGAACTGGGTATTATCGGCCCTATTCCA
CTCTCCGAGTTTTCTAAACAATCTATCGCAGCAAAAATTGCCGCCTCCCCACTCGC
GCGTGGTCGTGAACCGAAAGTTAAACTGGCTGTCGTTACCAACTCTACCTATGACG
GTCTGTGTTACAACGCGGAACTGATCAAACAAACCCTCGGCGACTCTGTCGAGGT
ACTGCATTTCGACGAGGCTTGGTATGCTTATGCGGCGTTTCACGAGTTCTACGACG
GCCGCTACGGTATGGGCACTTCTCGTTCCGAAGAGGGTCCGCTGGTCTTTGCTAC
CCATTCTACCCACAAGATGCTCGCGGCTTTTTCCCAAGCTAGCATGATTCACGTTC
AGGATGGTGGTACGCGCAAGCTGGACGTCGCCCGCTTTAACGAAGCCTTTATGAT
GCACATCAGCACCTCTCCACAGTACGGCATCATTGCGTCTCTCGATGTCGCAAGC
GCTATGATGGAAGGTCCTGCCGGTCGTAGCCTGATCCAAGAGACGTTCGATGAGG
CGCTGTCCTTCCGTCGTGCTCTGGCAATGTCCGTCAGAACCTGGACCGTAATGA
TTGGTGGTTCGGTGTCTGGCAACCGGAGCAGGTTGAGGGCACCGACCAGGTAGG
TACTCACGACTGGGTTCTCGAGCCTAGCGCGGACTGGCATGGTTTTGGTGACATT
GCGGAGGATTACGTTCTCCTCGATCCTATCAAAGTTACCCTGACCACCCCAGGTCT
GAGCGCTGGCGGTAAACTCTCTGAACAAGGCATCCCGGCAGCTATCGTTAGCCGT
TTCCTGTGGGAACGTGGTCTGGTGGTCGAGAAAACGGGTCTGTACTCTTTCCTGG
TTCTGTTCTCCATGGGTATCACGAAAGGCAAATGGTCTACTCTGGTTACCGAGCTG
CTCGAATTCAAACGCTGTTACGACGCGAATCTGCCACTCCTGGATGTGCTGCCTTC
TGTAGCGCAGGCGGGTGGTAAACGCTATAACGGTGTAGGTCTGCGTGATCTGTCC
GATGCCATGCACGCTTCTTATCGTGACAATGCCACGGCGAAGGCCATGAAGCGTA
TGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCG
GCGGTTATGCTGGTTCCGTACCCGCCAGGTATCCCGCTCATTATGCCGGGTGAAC
GTTTTACTGAAGCTACCCGCTCCATTCTGGACTATCTGGAGTTTGCCCGTACCTTC
GAGCGCGCGTTCCCGGGCTTTGACTCTGATGTTCACGGCCTCCAACATCAAGATG
GCCCGTCTGGCCGTTGTTATACCGTTAATGCATCAAGGAATAA
```

SEQUENCE LISTINGS

SEQ ID NO: 37 (Idc2-col C332G/A785C DNA sequence)
ATGTACAAAGATCTGAAATTCCCTGTTCTGATTGTACACCGCGATATCAAGGCGGA
CACGGTAGCCGGCGAGCGTGTTCGCGGTATTGCCCACGAACTCGAACAAGACGG
CTTTAGCATTCTCTACGGCGTCTTCTGCGGAAGGCCGCATTGTGGCTAGCACG
CACCACGGTCTCGCCTGCATCCTCGTGGCAGCTGAGGGTGCGGGTGAGAATCAG
CGTCTGCTCCAAGACGTGGTTGAGCTGATCCGTGTAGCTCGCGTCCGTGCGCCAC
AGCTCCCGATCTTCGCGCTGGGCGAACAGGTGACTATTGAAAACGCGCCTGCCGA
ATGTATGGCCGACCTGCACCAGCTCCGCGGCATTCTGTATCTCTTCGAGGATACTG
TCCCGTTCCTGGCACGTCAGGTTGCACGCGCAGCGCGTAACTACCTCGCTGGCCT
CCTCCCGCCATTCTTCCGTGCACTCGTGGAGCACACGGCCCAAAGCAATTACTCTT
GGCACACCCCGGGTCACGGTGGTGGTGTCGCTTACCGTAAATCTCCGGTAGGTCA
AGCTTTCCACCAGTTCTTTGGCGAGAATACCCTCCGCTCTGACCTGTCTGTTAGCG
TTCCAGAGCTGGGCAGCCTGCTGGATCACACTGGCCCTCTCGCGGAAGCAGAGG
ATCGTGCCGCTCGCAATTTCGGTGCGGACCACACCTTCTTTGTCATCAATGGTACC
TCTACTGCGAACAAAATCGTTTGGCACTCTATGGTTGGTCGCGAGGACCTGGTGCT
GGTCGATCGTACCTGTCACAAATCTATTCTGCACTCCATTATCATGACGGGTGCTA
TCCCACTGTACCTGACTCCGGAACGCAACGAACTGGGTATTATCGGCCCTATTCCA
CTCTCCGAGTTTTCTAAACAATCTATCGCAGCAAAAATTGCCGCCTCCCCACTCGC
GCGTGGTCGTGAACCGAAAGTTAAACTGGCTGTCGTTACCAACTCTACCTATGACG
GTCTGTGTTACAACGCGGAACTGATCAAACAAACCCTCGGCGACTCTGTCGAGGT
ACTGCATTTCGACGAGGCTTGGTATGCTTATGCGGCGTTTCACGAGTTCTACGACG
GCCGCTACGGTATGGGCACTTCTCGTTCCGAAGAGGGTCCGCTGGTCTTTGCTAC
CCATTCTACCCACAAGATGCTCGCGGCTTTTTCCCAAGCTAGCATGATTCACGTTC
AGGATGGTGGTACGCGCAAGCTGGACGTCGCCCGCTTTAACGAAGCCTTTATGAT
GCACATCAGCACCTCTCCACAGTACGGCATCATTGCGTCTCTCGATGTCGCAAGC
GCTATGATGGAAGGTCCTGCCGGTCGTAGCCTGATCAAGAGACGTTCGATGAGG
CGCTGTCCTTCCGTCGTGCTCTGGCGAATGTCCGTCAGAACCTGGACCGTAATGA
TTGGTGGTTCGGTGTCTGGCAACCGGAGCAGGTTGAGGGCACCGACCAGGTAGG
TACTCACGACTGGGTTCTCGAGCCTAGCGCGGACTGGCATGGTTTTGGTGACATT
GCGGAGGATTACGTTCTCCTCGATCCTATCAAAGTTACCCTGACCACCCCAGGTCT
GAGCGCTGGCGGTAAACTCTCTGAACAAGGCATCCCGGCAGCTATCGTTAGCCGT
TTCCTGTGGGAACGTGGTCTGGTGGTCGAGAAAACGGGTCTGTACTCTTTCCTGG
TTCTGTTCTCCATGGGTATCACGAAAGGCAAATGGTCTACTCTGGTTACCGAGCTG
CTCGAATTCAAACGCTGTTACGACGCGAATCTGCCACTCCTGGATGTGCTGCCTTC
TGTAGCGCAGGCGGGTGGTAAACGCTATAACGGTGTAGGTCTGCGTGATCTGTCC
GATGCCATGCACGCTTCTTATCGTGACAATGCCACGGCGAAGGCCATGAAGCGTA
TGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCG
GCGGTTATGCTGGTTCCGTACCCGCCAGGTATCCCGCTCATTATGCCGGGTGAAC
GTTTTACTGAAGCTACCCGCTCCATTCTGGACTATCTGGAGTTTGCCCGTACCTTC
GAGCGCGCGTTCCCGGGCTTTGACTCTGATGTTCACGGCCTCCAACATCAAGATG
GCCCGTCTGGCCGTTGTTATACCGTTGAATGCATCAAGGAATAA SEQ ID NO: 38 (Idc2-col C332G/A795C DNA sequence)
ATGTACAAAGATCTGAAATTCCCTGTTCTGATTGTACACCGCGATATCAAGGCGGA
CACGGTAGCCGGCGAGCGTGTTCGCGGTATTGCCCACGAACTCGAACAAGACGG
CTTTAGCATTCTCTACGGCGTCTTCTGCGGAAGGCCGCATTGTGGCTAGCACG
CACCACGGTCTCGCCTGCATCCTCGTGGCAGCTGAGGGTGCGGGTGAGAATCAG
CGTCTGCTCCAAGACGTGGTTGAGCTGATCCGTGTAGCTCGCGTCCGTGCGCCAC
AGCTCCCGATCTTCGCGCTGGGCGAACAGGTGACTATTGAAAACGCGCCTGCCGA
ATGTATGGCCGACCTGCACCAGCTCCGCGGCATTCTGTATCTCTTCGAGGATACTG
TCCCGTTCCTGGCACGTCAGGTTGCACGCGCAGCGCGTAACTACCTCGCTGGCCT
CCTCCCGCCATTCTTCCGTGCACTCGTGGAGCACACGGCCCAAAGCAATTACTCTT
GGCACACCCCGGGTCACGGTGGTGGTGTCGCTTACCGTAAATCTCCGGTAGGTCA
AGCTTTCCACCAGTTCTTTGGCGAGAATACCCTCCGCTCTGACCTGTCTGTTAGCG
TTCCAGAGCTGGGCAGCCTGCTGGATCACACTGGCCCTCTCGCGGAAGCAGAGG
ATCGTGCCGCTCGCAATTTCGGTGCGGACCACACCTTCTTTGTCATCAATGGTACC
TCTACTGCGAACAAAATCGTTTGGCACTCTATGGTTGGTCGCGAGGACCTGGTGCT
GGTCGATCGTAACTGTCACAACTCTATTCTGCACTCCATTATCATGACGGGTGCTA
TCCCACTGTACCTGACTCCGGAACGCAACGAACTGGGTATTATCGGCCCTATTCCA
CTCTCCGAGTTTTCTAAACAATCTATCGCAGCAAAAATTGCCGCCTCCCCACTCGC
GCGTGGTCGTGAACCGAAAGTTAAACTGGCTGTCGTTACCAACTCTACCTATGACG
GTCTGTGTTACAACGCGGAACTGATCAAACAAACCCTCGGCGACTCTGTCGAGGT
ACTGCATTTCGACGAGGCTTGGTATGCTTATGCGGCGTTTCACGAGTTCTACGACG
GCCGCTACGGTATGGGCACTTCTCGTTCCGAAGAGGGTCCGCTGGTCTTTGCTAC
CCATTCTACCCACAAGATGCTCGCGGCTTTTTCCCAAGCTAGCATGATTCACGTTC
AGGATGGTGGTACGCGCAAGCTGGACGTCGCCCGCTTTAACGAAGCCTTTATGAT
GCACATCAGCACCTCTCCACAGTACGGCATCATTGCGTCTCTCGATGTCGCAAGC
GCTATGATGGAAGGTCCTGCCGGTCGTAGCCTGATCAAGAGACGTTCGATGAGG
CGCTGTCCTTCCGTCGTGCTCTGGCGAATGTCCGTCAGAACCTGGACCGTAATGA
TTGGTGGTTCGGTGTCTGGCAACCGGAGCAGGTTGAGGGCACCGACCAGGTAGG
TACTCACGACTGGGTTCTCGAGCCTAGCGCGGACTGGCATGGTTTTGGTGACATT
GCGGAGGATTACGTTCTCCTCGATCCTATCAAAGTTACCCTGACCACCCCAGGTCT
GAGCGCTGGCGGTAAACTCTCTGAACAAGGCATCCCGGCAGCTATCGTTAGCCGT
TTCCTGTGGGAACGTGGTCTGGTGGTCGAGAAAACGGGTCTGTACTCTTTCCTGG
TTCTGTTCTCCATGGGTATCACGAAAGGCAAATGGTCTACTCTGGTTACCGAGCTG CTCGAATTCAAACGCTGTTACGACGCGAATCTGCCACTCCTGGATGTGCTGCCTTC
TGTAGCGCAGGCGGGTGGTAAACGCTATAACGGTGTAGGTCTGCGTGATCTGTCC
GATGCCATGCACGCTTCTTATCGTGACAATGCCACGGCGAAGGCCATGAAGCGTA
TGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCG
GCGGTTATGCTGGTTCCGTACCCGCCAGGTATCCCGCTCATTATGCCGGGTGAAC
GTTTTACTGAAGCTACCCGCTCCATTCTGGACTATCTGGAGTTTGCCCGTACCTTC
GAGCGCGCGTTCCCGGGCTTTGACTCTGATGTTCACGGCCTCCAACATCAAGATG
GCCCGTCTGGCCGTTGTTATACCGTTGAATGCATCAAGGAATAA SEQ ID NO: 39 (Idc2-co1 A785C/A795C DNA sequence)
ATGTACAAAGATCTGAAATTCCCTGTTCTGATTGTACACCGCGATATCAAGGCGGA
CACGGTAGCCGGCGAGCGTGTTCGCGGTATTGCCCACGAACTCGAACAAGACGG
CTTTAGCATTCTCTCTACGGCGTCTTCTGCGGAAGGCCGCATTGTGGCTAGCACG
CACCACGGTCTCGCCTGCATCCTCGTGGCAGCTGAGGGTGCGGGTGAGAATCAG
CGTCTGCTCCAAGACGTGGTTGAGCTGATCCGTGTAGCTCGCGTCCGTGCGCCAC
AGCTCCCGATCTTCGCGCTGGGCGAACAGGTGACTATTGAAAACGCGCCTGCCGA
ATCTATGGCCGACCTGCACCAGCTCCGCGGCATTCTGTATCTCTTCGAGGATACTG
TCCCGTTCCTGGCACGTCAGGTTGCACGCGCAGCGCGTAACTACCTCGCTGGCCT
CCTCCCGCCATTCTTCCGTGCACTCGTGGAGCACACGGCCCAAAGCAATTACTCTT
GGCACACCCCGGGTCACGGTGGTGGTGTCGCTTACCGTAAATCTCCGGTAGGTCA
AGCTTTCCACCAGTTCTTTGGCGAGAATACCCTCCGCTCTGACCTGTCTGTTAGCG
TTCCAGAGCTGGGCAGCCTGCTGGATCACACTGGCCCTCTCGCGGAAGCAGAGG
ATCGTGCCGCTCGCAATTTCGGTGCGGACCACACCTTCTTTGTCATCAATGGTACC
TCTACTGCGAACAAAATCGTTTGGCACTCTATGGTTGGTCGCGAGGACCTGGTGCT
GGTCGATCGTACCTGTCACAACTCTATTCTGCACTCCATTATCATGACGGGTGCTA
TCCCACTGTACCTGACTCCGGAACGCAACGAACTGGGTATTATCGGCCCTATTCCA
CTCTCCGAGTTTTCTAAACAATCTATCGCAGCAAAAATTGCCGCCTCCCCACTCGC
GCGTGGTCGTGAACCGAAAGTTAAACTGGCTGTCGTTACCAACTCTACCTATGACG
GTCTGTGTTACAACGCGGAACTGATCAAACAAACCCTCGGCGACTCTGTCGAGGT
ACTGCATTTCGACGAGGCTTGGTATGCTTATGCGGCGTTTCACGAGTTCTACGACG
GCCGCTACGGTATGGGCACTTCTCGTTCCGAAGAGGGTCCGCTGGTCTTTGCTAC
CCATTCTACCCACAAGATGCTCGCGGCTTTTTCCCAAGCTAGCATGATTCACGTTC
AGGATGGTGGTACGCGCAAGCTGGACGTCGCCCGCTTTAACGAAGCCTTTATGAT
GCACATCAGCACCTCTCCACAGTACGGCATCATTGCGTCTCTCGATGTCGCAAGC
GCTATGATGGAAGGTCCTGCCGGTCGTAGCCTGATCAAGAGACGTTCGATGAGG
CGCTGTCCTTCCGTCGTGCTCTGGCGAATGTCCGTCAGAACCTGGACCGTAATGA
TTGGTGGTTCGGTGTCTGGCAACCGGAGCAGGTTGAGGGCACCGACCAGGTAGG
TACTCACGACTGGGTTCTCGAGCCTAGCGCGGACTGGCATGGTTTTGGTGACATT
GCGGAGGATTACGTTCTCCTCGATCCTATCAAAGTTACCCTGACCACCCCAGGTCT
GAGCGCTGGCGGTAAACTCTCTGAACAAGGCATCCCGGCCAGCTATCGTTAGCCGT
TTCCTGTGGGAACGTGGTCTGGTGGTCGAGAAAACGGGTCTGTACTCTTTCCTGG
TTCTGTTCTCCATGGGTATCACGAAAGGCAAATGGTCTACTCTGGTTACCGAGCTG
CTCGAATTCAAACGCTGTTACGACGCGAATCTGCCACTCCTGGATGTGCTGCCTTC
TGTAGCGCAGGCGGGTGGTAAACGCTATAACGGTGTAGGTCTGCGTGATCTGTCC
GATGCCATGCACGCTTCTTATCGTGACAATGCCACGGCGAAGGCCATGAAGCGTA
TGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCG
GCGGTTATGCTGGTTCCGTACCCGCCAGGTATCCCGCTCATTATGCCGGGTGAAC
GTTTTACTGAAGCTACCCGCTCCATTCTGGACTATCTGGAGTTTGCCCGTACCTTC
GAGCGCGCGTTCCCGGGCTTTGACTCTGATGTTCACGGCCTCCAACATCAAGATG
GCCCGTCTGGCCGTTGTTATACCGTTGAATGCATCAAGGAATAA SEQ ID NO: 40 (Idc2-co1 C332G/A785C/A795C DNA sequence)
ATGTACAAAGATCTGAAATTCCCTGTTCTGATTGTACACCGCGATATCAAGGCGGA
CACGGTAGCCGGCGAGCGTGTTCGCGGTATTGCCCACGAACTCGAACAAGACGG
CTTTAGCATTCTCTCTACGGCGTCTTCTGCGGAAGGCCGCATTGTGGCTAGCACG
CACCACGGTCTCGCCTGCATCCTCGTGGCAGCTGAGGGTGCGGGTGAGAATCAG
CGTCTGCTCCAAGACGTGGTTGAGCTGATCCGTGTAGCTCGCGTCCGTGCGCCAC
AGCTCCCGATCTTCGCGCTGGGCGAACAGGTGACTATTGAAAACGCGCCTGCCGA
ATGTATGGCCGACCTGCACCAGCTCCGCGGCATTCTGTATCTCTTCGAGGATACTG
TCCCGTTCCTGGCACGTCAGGTTGCACGCGCAGCGCGTAACTACCTCGCTGGCCT
CCTCCCGCCATTCTTCCGTGCACTCGTGGAGCACACGGCCCAAAGCAATTACTCTT
GGCACACCCCGGGTCACGGTGGTGGTGTCGCTTACCGTAAATCTCCGGTAGGTCA
AGCTTTCCACCAGTTCTTTGGCGAGAATACCCTCCGCTCTGACCTGTCTGTTAGCG
TTCCAGAGCTGGGCAGCCTGCTGGATCACACTGGCCCTCTCGCGGAAGCAGAGG
ATCGTGCCGCTCGCAATTTCGGTGCGGACCACACCTTCTTTGTCATCAATGGTACC
TCTACTGCGAACAAAATCGTTTGGCACTCTATGGTTGGTCGCGAGGACCTGGTGCT
GGTCGATCGTACCTGTCACAACTCTATTCTGCACTCCATTATCATGACGGGTGCTA
TCCCACTGTACCTGACTCCGGAACGCAACGAACTGGGTATTATCGGCCCTATTCCA
CTCTCCGAGTTTTCTAAACAATCTATCGCAGCAAAAATTGCCGCCTCCCCACTCGC
GCGTGGTCGTGAACCGAAAGTTAAACTGGCTGTCGTTACCAACTCTACCTATGACG
GTCTGTGTTACAACGCGGAACTGATCAAACAAACCCTCGGCGACTCTGTCGAGGT
ACTGCATTTCGACGAGGCTTGGTATGCTTATGCGGCGTTTCACGAGTTCTACGACG
GCCGCTACGGTATGGGCACTTCTCGTTCCGAAGAGGGTCCGCTGGTCTTTGCTAC
CCATTCTACCCACAAGATGCTCGCGGCTTTTTCCCAAGCTAGCATGATTCACGTTC
AGGATGGTGGTACGCGCAAGCTGGACGTCGCCCGCTTTAACGAAGCCTTTATGAT

```
GCACATCAGCACCTCTCCACAGTACGGCATCATTGCGTCTCTCGATGTCGCAAGC
GCTATGATGGAAGGTCCTGCCGGTCGTAGCCTGATCCAAGAGACGTTCGATGAGG
CGCTGTCCTTCCGTCGTGCTCTGGCGAATGTCCGTCAGAACCTGGACGTAATGA
TTGGTGGTTCGGTGTCTGGCAACCGGAGCAGGTTGAGGGCACCGACCAGGTAGG
TACTCACGACTGGGTTCTCGAGCCTAGCGCGGACTGGCATGGTTTTGGTGACATT
GCGGAGGATTACGTTCTCCTCGATCCTATCAAAGTTACCCTGACCACCCCAGGTCT
GAGCGCTGGCGGTAAACTCTCTGAACAAGGCATCCCGGCTGCTATCGTTAGCCGT
TTCCTGTGGGAACGTGGTCTGGTGGTCGAGAAAACGGGTCTGTACTCTTTCCTGG
TTCTGTTCTCCATGGGTATCACGAAAGGCAAATGGTCTACTCTGGTTACCGAGCTG
CTCGAATTCAAACGCTGTTACGACGCGAATCTGCCACTCCTGGATGTGCTGCCTTC
TGTAGCGCAGGCGGGTGGTAAACGCTATAACGGTGTAGGTCTGCGTGATCTGTCC
GATGCCATGCACGCTTCTTATCGTGACAATGCCACGGCGAAGGCCATGAAGCGTA
TGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCG
GCGGTTATGCTGGTTCCGTACCCGCCAGGTATCCCGCTCATTATGCCGGGTGAAC
GTTTTACTGAAGCTACCCGCTCCATTCTGGACTATCTGGAGTTTGCCCGTACCTTC
GAGCGCGCGTTCCCGGGCTTTGACTCTGATGTTCACGGCCTCCAACATCAAGATG
GCCCGTCTGGCCGTTGTTATACCGTTGAATGCATCAAGGAATAA

SEQ ID NO: 41 (cadA DNA sequence)
ATGAACGTTATTGCAATATTGAATCACATGGGGGTTTATTTTAAGAAGAACCCATC
CGTGAACTTCATCGCGCGCTTGAACGTCTGAACTTCCAGATTGTTTACCCGAACGA
CCGTGACGACTTATTAAAACTGATCGAAAACAATGCGCGTCTGTGCGGCGTTATT
TTGACTGGGATAAATATAATCTCGAGCTGTGCGAAGAAATTAGCAAAATGAACGAG
AACCTGCCGTTGTACGCGTTCGCTAATACGTATTCCACTCTCGATGTAAGCCTGAA
TGACCTGCGTTTACAGATTAGCTTCTTTGAATATGCGCTGGGTGCTGCTGAAGATA
TTGCTAATAAGATCAAGCAGACCACTGACGAATATATCAACACTATTCTGCCTCCG
CTGACTAAAGCACTGTTTAAATATGTTCGTGAAGGTAAATATACTTTCTGTACTCCT
GGTCACATGGGCGGTACTGCATTCCAGAAAAGCCCGGTAGGTAGCCTGTTCTATG
ATTTCTTTGGTCCGAATACCATGAAATCTGATATTTCCATTTCAGTATCTGAACTGG
GTTCTCTGCTGGATCACAGTGGTCCACACAAAGAAGCAGAACAGTATATCGCTCGC
GTCTTTAACGCAGACCGCAGCTACATGGTGACCAACGGTACTTCCACTGCGAACA
AAATTGTTGGTATGTACTCTGCTCCAGCAGGCAGCACCATTCTGATTGACCGTAAC
TGCCACAAATCGCTGACCCACCTGATGATGATGAGCGATGTTACGCCAATCTATTT
CCGCCCGACCCGTAACGCTTACGGTATTCTTGGTGGTATCCCACAGAGTGAATTCC
AGCACGCTACCATTGCTAAGCGCGTGAAAGAAACACCAAACGCAACCTGGCCGGT
ACATGCTGTAATTACCAACTCTACCTATGATGGTCTGCTGTACAACACCGACTTCAT
CAAGAAAACACTGGATGTGAAATCCATCCACTTTGACTCCGCGTGGGTGCCTTACA
CCAACTTCTCACCGATTTACGAAGGTAAATGCGGTATGAGCGGTGGCCGTGTAGA
AGGGAAAGTGATTTACGAAACCCAGTCCACTCACAAACTGCTGGCGGCGTTCTCT
CAGGCTTCCATGATCCACGTTAAAGGTGACGTAAACGAAGAAACCTTTAACGAAGC
CTACATGATGCACACCACCACTTCTCCGCACTACGGTATCGTGGCGTCCACTGAAA
CCGCTGCGGCGATGATGAAAGGCAATGCAGGTAAGCGTCTGATCAACGGTTCTAT
TGAACGTGCGATCAAATTCCGTAAAGAGATCAAACGTCTGAGAACGGAATCTGATG
GCTGGTTCTTTGATGTATGGCAGCCGGATCATATCGATACGACTGAATGCTGGCCG
CTGCGTTCTGACAGCACCTGGCACGGCTTCAAAAACATCGATAACGAGCACATGTA
TCTTGACCCGATCAAAGTCACCCTGCTGACTCCGGGGATGGAAAAAGACGGCACC
ATGAGCGACTTTGGTATTCCGGCCAGCATCGTGGCGAAATACCTCGACGAACATG
GCATCGTTGTTGAGAAAACCGGTCCGTATAACCTGCTGTTCCTGTTCAGCATCGGT
ATCGATAAGACCAAAGCACTGAGCCTGCTGCGTGCTCTGACTGACTTTAAACGTGC
GTTCGACCTGAACCTGCGTGTGAAAAACATGCTGCCGTCTCTGTATCGTGAAGATC
CTGAATTCTATGAAAACATGCGTATTCAGGAACTGGCTCAGAATATCCACAAACTG
ATTGTTCACCACAATCTGCCGGATCTGATGTATCGCGCATTTGAAGTGCTGCCGAC
GATGGTAATGACTCCGTATGCTGCATTCCAGAAAGAGCTGCACGGTATGACCGAA
GAAGTTTACCTCGACGAAATGGTAGGTCGTATTAACGCCAATATGATCCTTCCGTA
CCCGCCGGGAGTTCCTCTGGTAATGCCGGGTGAAATGATCACCGAAGAAAGCCGT
CCGGTTCTGGAGTTCCTGCAGATGCTGTGTGAAATCGGCGCTCACTATCCGGCT
TTGAAACCGATATTCACGGTGCATACCGTCAGGCTGATGGCCGCTATACCGTTAAG
GTATTGAAAGAAGAAAGCAAAAAATAA SEQ ID NO: 42 (ldcC DNA sequence)
ATGAACATCATTGCCATTATGGGACCGCATGGCGTCTTTTATAAAGATGAGCCCAT
CAAAGAACTGGAGTCGGCGCTGGTGGCGCAAGGCTTTCAGATTATCTGGCCACAA
AACAGCGTTGATTTGCTGAAATTTATCGAGCATAACCCTCGAATTTGCGGCGTGAT
TTTTGACTGGGATGAGTACAGTCTCGATTTATGTAGCGATATCAATCAGCTTAATGA
ATATCTCCCGCTTTATGCCTTCATCAACACCCACTCGACGATGGATGTCAGCGTGC
AGGATATGCGGATGGCGCTCTGGTTTTTTGAATATGCGCTGGGGCAGGCGGAAGA
TATCGCCATTCGTATGCGTCAGTACACCGACGAATATCTTGATAACATTACACCGC
CGTTCACGAAAGCCTTGTTTACCTACGTCAAAGAGCGGAAGTACACCTTTTGTACG
CCGGGGCATATGGGCGGCACCGCATATCAAAAAAGCCCGGTTGGCTGTCTGTTTT
ATGATTTTTCGGCGGGAATACTCTTAAGGCTGATGTCTCTATTTCGGTCACCGAG
CTTGGTTCGTTGCTCGACCACACCGGGCCACACCTGGAAGCGGAAGAGTACATCG
CGCGGACTTTTGGCGCGGAACAGAGTTATATCGTTACCAACGGAACATCGACGTC
GAACAAAATTGTGGGTATGTACGCCGCGCCATCCGGCAGTACGCTGTTGATCGAC
CGCAATTGTCATAAATCGCTGGCGCATCTGTTGATGATGAACGATGTAGTGCCAGT
CTGGCTGAAACCGACGCGTAATGCGTTGGGGATTCTTGGTGGGATCCCGCGCCGT
GAATTTACTCGCGACAGCATCGAAGAGAAAGTCGCTGCTACCACGCAAGCACAAT
```

-continued

```
SEQUENCE LISTINGS

GGCCGGTTCATGCGGTGATCACCAACTCCACCTATGATGGCTTGCTCTACAACACC
GACTGGATCAAACAGACGCTGGATGTCCCGTCGATTCACTTCGATTCTGCCTGGGT
GCCGTACACCCATTTTCATCCGATCTACCAGGGTAAAAGTGGTATGAGCGGCGAG
CGTGTTGCGGGAAAAGTGATCTTCGAAACGCAATCGACCCACAAAATGCTGGCGG
CGTTATCGCAGGCTTCGCTGATCCACATTAAAGGCGAGTATGACGAAGAGGCCTTT
AACGAAGCCTTTATGATGCATACCACCACCTCGCCCAGTTATCCCATTGTTGCTTC
GGTTGAGACGGCGGCGGCGATGCTGCGTGGTAATCCGGGCAAACGGCTGATTAA
CCGTTCAGTAGAACGAGCTCTGCATTTTCGCAAAGAGGTCCAGCGGCTGCGGGAA
GAGTCTGACGGTTGGTTTTTCGATATCTGGCAACCGCCGCAGGTGGATGAAGCCG
AATGCTGGCCCGTTGCGCCTGGCGAACAGTGGCACGGCTTTAACGATGCGGATG
CCGATCATATGTTTCTCGATCCGGTTAAAGTCACTATTTTGACACCGGGGATGGAC
GAGCAGGGCAATATGAGCGAGGAGGGGATCCCGGCGGCGCTGGTAGCAAAATTC
CTCGACGAACGTGGGATCGTAGTAGAGAAAACCGGCCCTTATAACCTGCTGTTTCT
CTTTAGTATTGGCATCGATAAAACCAAAGCAATGGGATTATTGCGTGGGTTGACGG
AATTCAAACGCTCTTACGATCTCAACCTGCGGATCAAAAATATGCTACCCGATCTCT
ATGCAGAAGATCCCGATTTCTACCGCAATATGCGTATTCAGGATCTGGCACAAGGG
ATCCATAAGCTGATTCGTAAACACGATCTTCCCGGTTTGATGTTGCGGGCATTCGA
TACTTTGCCGGAGATGATCATGACGCCACATCAGGCATGGCAACGACAAATTAAAG
GCGAAGTAGAAACCATTGCGCTGGAACAACTGGTCGGTAGAGTATCGGCAAATAT
GATCCTGCCTTATCCACCGGGCGTACCGCTGTTGATGCCTGGAGAAATGCTGACC
AAAGAGAGCCGCACAGTACTCGATTTTCTACTGATGCTTTGTTCCGTCGGGCAACA
TTACCCCGGTTTTGAAACGGATATTCACGGCGCGAAACAGGACGAAGACGGCGTT
TACCGCGTACGAGTCCTAAAAATGGCGGGATAA
```

REFERENCES

The references, patents and published patent applications listed below, and all references cited in the specification above are hereby incorporated by reference in their entirety, as if fully set forth herein.
1. Wertz et al. "Chimeric nature of two plasmids of *Hafnia alvei* encoding the bacteriocins alveicins A and B." Journal of Bacteriology, (2004) 186: 1598-1605).

What is claimed is:

1. A product, which is one of the following products I) through IV):

I) a first expression plasmid vector comprising:
one or more first polynucleotides encoding a first polypeptide, and
a backbone plasmid capable of autonomous replication in a host cell;
wherein the first expression plasmid vector further comprises:
one or more second polynucleotides independently selected from the group consisting of:
a polynucleotide encoding a polypeptide comprising a lysine decarboxylase polypeptide, a fragment thereof or a mutant thereof, and
a polynucleotide encoding a polypeptide comprising a lysine biosynthesis polypeptide, a fragment thereof or a mutant thereof;

II) a mutant host cell comprising one or more first polynucleotides integrated into a chromosome of a host cell, which further comprises one or more second polynucleotides integrated into a chromosome of the host cell, wherein the second polynucleotide is selected from the group consisting of:
- a polynucleotide encoding a polypeptide comprising a lysine decarboxylase polypeptide, a fragment thereof or a mutant thereof, and
- a polynucleotide encoding a polypeptide comprising a lysine biosynthesis polypeptide, a fragment thereof or a mutant thereof;

III) a transformant comprising one or more the first expression plasmid vectors of the product I) in a host cell, which further comprises one or more second expression plasmid vectors comprising one or more polynucleotides and a backbone plasmid capable of autonomous replication in a host cell; wherein the one or more polynucleotides are independently selected from the group consisting of:
- a polynucleotide encoding a polypeptide comprising a tetracycline efflux pump polypeptide, a fragment thereof or a mutant thereof,
- a polynucleotide encoding a polypeptide comprising a lysine decarboxylase polypeptide, a fragment thereof or a mutant thereof, and
- a polynucleotide encoding a polypeptide comprising a lysine biosynthesis polypeptide, a fragment thereof or a mutant thereof;

wherein the polynucleotide encoding a polypeptide comprising a lysine decarboxylase polypeptide is SEQ ID NO: 41 (cadA), SEQ ID NO: 42 (ldcC), SEQ ID NO: 8 (ldc2), fragments thereof, and mutants thereof, and the polynucleotide encoding a polypeptide comprising a lysine biosynthesis polypeptide is selected from the group consisting of sucA, ppc, aspC, lysC, asd, dapA (dihydrodipicolinate synthase), dapB, dapD, argD, dapE, dapF, lysA, ddh, pntAB, cyoABE, gadAB, ybjE, gdhA, gltA, sucC, gadC, acnB, pflB, thrA, aceA, aceB, gltB, aceE, sdhA, murE, speE, speG, puuA, puuP, ygjG, fragments thereof, and mutants thereof, wherein the mutant of SEQ ID NO: 8 (ldc2) is selected from the group consisting of SEQ ID NO: 10 (ldc2 co-1), SEQ ID NO: 34 (ldc2 co-1 C332G), SEQ ID NO: 35 (ldc2 co-1 A785C), SEQ ID NO: 36 (ldc2 co-1 A795C), SEQ ID NO: 37 (ldc2 co-1 C332G/A785C), SEQ ID NO: 38 (ldc2 co-1 C332G/A795C), SEQ ID NO: 39 (ldc2 co-1 A785C/A795C), and SEQ ID NO: 40 (ldc2 co-1 C332G/A785C/A795C);

IV) a transformant comprising one or more the first expression plasmid vectors of the product I) in a host cell, which further comprises one or more second expression plasmid vectors comprising one or more polynucleotides and a backbone plasmid capable of autonomous replication in a host cell; wherein the one or more polynucleotides are independently selected from the group consisting of:
- a polynucleotide encoding a polypeptide comprising a tetracycline efflux pump polypeptide, a fragment thereof or a mutant thereof,
- a polynucleotide encoding a polypeptide comprising a lysine decarboxylase polypeptide, a fragment thereof or a mutant thereof, and
- a polynucleotide encoding a polypeptide comprising a lysine biosynthesis polypeptide, a fragment thereof or a mutant thereof;

wherein the polypeptide comprising a lysine decarboxylase polypeptide is selected from the group consisting of SEQ ID NO: 6 (CadA), SEQ ID NO: 7 (LdcC), SEQ ID NO: 9 (Ldc2), fragments thereof, and mutants thereof, and the polypeptide comprising a lysine biosynthesis polypeptide is selected from the group consisting of SucA, Ppc, AspC, LysC, Asd, DapA (dihydrodipicolinate synthase), DapB, DapD, ArgD, DapE, DapF, LysA, Ddh, PntAB, CyoABE, GadAB, YbjE, GdhA, GltA, SucC, GadC, AcnB, PflB, ThrA, AceA, AceB, GltB, AceE, SdhA, MurE, SpeE, SpeG, PuuA, PuuP, and Ygj G, fragments thereof, and mutants thereof, wherein the mutant of SEQ ID NO: 9 (Ldc2) is selected from the group consisting of SEQ ID NO: 11 (Ldc2 S111C), SEQ ID NO: 16 (Ldc2 N262T), SEQ ID NO: 17 (Ldc2 K265N), SEQ ID NO: 18 (Ldc2 S111C/N262T), SEQ ID NO: 19 (Ldc2 S111C/K265N), SEQ ID NO: 20 (Ldc2 N262T/K265N), and SEQ ID NO: 21 (Ldc2 S111C/N262T/K265N); wherein, in I) and II), the first polynucleotide encodes a first polypeptide consisting of a mutant of the amino acid sequence SEQ ID NO: 2 (TetA) and fragments thereof, wherein the mutant of TetA or the fragment thereof is selected from the group consisting of amino acid sequences of SEQ ID NO: 32 (TetA aa1-96), TetA aa1-97, TetA aa1-98, TetA aa1-99, TetA aa1-100, TetA aa1-101, TetA aa1-102, TetA aa1-103, TetA aa1-104, TetA aa1-124, TetA aa1-125, TetA aa1-126, TetA aa1-127, TetA aa1-128, TetA aa1-129, TetA aa1-130, TetA aa1-131, TetA aa1-132, TetA aa1-133, TetA aa1-155, TetA aa1-156, TetA aa1-157, TetA aa1-158, TetA aa1-159, TetA aa1-160, TetA aa1-161, TetA aa1-162, TetA aa1-182, TetA aa1-183, TetA aa1-184, SEQ ID NO: 30 (TetA (aa1-185)), TetA aa1-186, TetA aa1-187, TetA aa1-188, TetA aa1-189, TetA aa1-190, TetA aa1-191, TetA aa1-192, TetA aa1-193, TetA aa1-194, and TetA aa1-195, and the host cell is selected from the group consisting of Escherichia, Corynebacterium, and Hafnia.

2. A product of claim 1, which is I) the first expression plasmid vector, wherein
- the polynucleotide encoding a polypeptide comprising a lysine decarboxylase polypeptide is selected from the group consisting of SEQ ID NO: 41 (cadA), SEQ ID NO: 42 (ldcC), SEQ ID NO: 8 (ldc2), fragments thereof, and mutants thereof, and
- the polynucleotide encoding a polypeptide comprising a lysine biosynthesis polypeptide is selected from the group consisting of sucA, ppc, aspC, lysC, asd, dapA (encoding dihydrodipicolinate synthase), dapB, dapD, argD, dapE, dapF, lysA, ddh, pntAB, cyoABE, gadAB, ybjE, gdhA, gltA, sucC, gadC, acnB, pflB, thrA, aceA, aceB, gltB, aceE, sdhA, murE, speE, speG, puuA, puuP, ygjG, fragments thereof, and mutants thereof.

3. A product of claim 2, wherein the mutant of SEQ ID NO: 8 (ldc2) is selected from the group consisting of SEQ ID NO: 10 (ldc2 co-1), SEQ ID NO: 34 (ldc2 co-1 C332G), SEQ ID NO: 35 (ldc2 co-1 A785C), SEQ ID NO: 36 (ldc2 co-1 A795C), SEQ ID NO: 37 (ldc2 co-1 C332G/A785C), SEQ ID NO: 38 (ldc2 co-1 C332G/A795C), SEQ ID NO: 39 (ldc2 co-1 A785C/A795C), and SEQ ID NO: 40 (ldc2 co-1 C332G/A785C/A795C).

4. A product of claim 1, which is I) the first expression plasmid vector, wherein
- the polypeptide comprising a lysine decarboxylase polypeptide is selected from the group consisting of SEQ ID NO: 6 (CadA), SEQ ID NO: 7 (LdcC), SEQ ID NO: 9 (Ldc2), fragments thereof, and mutants thereof, and
- the polypeptide comprising a lysine biosynthesis polypeptide is selected from the group consisting of SucA, Ppc, AspC, LysC, Asd, DapA, DapB, DapD, ArgD, DapE, DapF, LysA, Ddh, PntAB, CyoABE, GadAB, YbjE, GdhA, GltA, SucC, GadC, AcnB, PflB, ThrA, AceA, AceB, GltB, AceE, SdhA, MurE, SpeE, SpeG, PuuA, PuuP, and YgjG, fragments thereof, and mutants thereof.

5. A product of claim 4, wherein the mutant of SEQ ID NO: 9 (Ldc2) is selected from the group consisting of SEQ ID NO: 11 (Ldc2 S111C), SEQ ID NO: 16 (Ldc2 N262T), SEQ ID NO: 17 (Ldc2 K265N), SEQ ID NO: 18 (Ldc2 S111C/N262T), SEQ ID NO: 19 (Ldc2 S111C/K265N), SEQ ID NO: 20 (Ldc2 N262T/K265N), and SEQ ID NO: 21 (Ldc2 S111C/N262T/K265N).

6. A product of claim 1, which is II) the mutant host cell, wherein
the polynucleotide encoding a polypeptide comprising a lysine decarboxylase polypeptide is selected from the group consisting of SEQ ID NO: 41 (cadA), SEQ ID NO: 42 (IdcC), SEQ ID NO: 8 (Idc2), fragments thereof, and mutants thereof, and
the polynucleotide encoding a polypeptide comprising a lysine biosynthesis polypeptide is selected from the group consisting of sucA, ppc, aspC, lysC, asd, dapA, dapB, dapD, argD, dapE, dapF, lysA, ddh, pntAB, cyoABE, gadAB, ybjE, gdhA, gltA, sucC, gadC, acnB, pflB, thrA, aceA, aceB, gltB, aceE, sdhA, murE, speE, speG, puuA, puuP, ygjG, fragments thereof, and mutants thereof.

7. A product of claim 6, wherein the mutant of SEQ ID NO: 8 (Idc2) is selected from the group consisting of SEQ ID NO: 10 (Idc2 co-1), SEQ ID NO: 34 (Idc2 co-1 C332G), SEQ ID NO: 35 (Idc2 co-1 A785C), SEQ ID NO: 36 (Idc2 co-1 A795C), SEQ ID NO: 37 (Idc2 co-1 C332G/A785C), SEQ ID NO: 38 (Idc2 co-1 C332G/A795C), SEQ ID NO: 39 (Idc2 co-1 A785C/A795C), and SEQ ID NO: 40 (Idc2 co-1 C332G/A785C/A795C).

8. A product of claim 1, which is II) the mutant host cell, wherein the polypeptide comprising a lysine decarboxylase polypeptide is selected from the group consisting of SEQ ID NO: 6 (CadA), SEQ ID NO: 7 (LdcC), SEQ ID NO: 9 (Ldc2), fragments thereof, and mutants thereof, and
the polypeptide comprising a lysine biosynthesis polypeptide is selected from the group consisting of SucA, Ppc, AspC, LysC, Asd, DapA (dihydrodipicolinate synthase), DapB, DapD, ArgD, DapE, DapF, LysA, Ddh, PntAB, CyoABE, GadAB, YbjE, GdhA, GltA, SucC, GadC, AcnB, PflB, ThrA, AceA, AceB, GltB, AceE, SdhA, MurE, SpeE, SpeG, PuuA, PuuP, and YgjG, fragments thereof, and mutants thereof.

9. A product of claim 8, wherein the mutant of SEQ ID NO: 9 (Ldc2) is selected from the group consisting of SEQ ID NO: 11 (Ldc2 S111C), SEQ ID NO: 16 (Ldc2 N262T), SEQ ID NO: 17 (Ldc2 K265N), SEQ ID NO: 18 (Ldc2 S111C/N262T), SEQ ID NO: 19 (Ldc2 S111C/K265N), SEQ ID NO: 20 (Ldc2 N262T/K265N), and SEQ ID NO: 21 (Ldc2 S111C/N262T/K265N).

10. A method for producing a lysine comprising:
obtaining the transformant of the product III) or IV) and/or the mutant host cell of the product II) of claim 1;
culturing the transformant and/or mutant host cell under conditions effective for the expression of the lysine; and
harvesting the lysine.

11. A method for producing cadaverine (1,5-pentanediamine) comprising:
1a) cultivating the transformant of the product III) or IV) and/or the mutant host cell of the product II) of claim 1;
1b) producing cadaverine using the culture obtained from step 1a to decarboxylate lysine; and
1c) extracting and purifying cadaverine using the culture obtained from step 1b.

* * * * *